(12) United States Patent
Hatakeyama et al.

(10) Patent No.: US 7,303,852 B2
(45) Date of Patent: Dec. 4, 2007

(54) PHOTOACID GENERATING COMPOUNDS, CHEMICALLY AMPLIFIED POSITIVE RESIST MATERIALS, AND PATTERN FORMING METHOD

(75) Inventors: Jun Hatakeyama, Niigata-ken (JP); Tomohiro Kobayashi, Niigata-ken (JP); Youichi Ohsawa, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 236 days.

(21) Appl. No.: 10/375,773

(22) Filed: Feb. 27, 2003

(65) Prior Publication Data

US 2003/0235779 A1    Dec. 25, 2003

Related U.S. Application Data

(63) Continuation-in-part of application No. 10/331,785, filed on Dec. 27, 2002, now abandoned.

(30) Foreign Application Priority Data

Dec. 27, 2001   (JP) .............................. 2001-397192

(51) Int. Cl.
*G03F 7/00*    (2006.01)
*G03F 7/004*   (2006.01)

(52) U.S. Cl. ................. 430/270.1; 430/280.1; 430/286.1; 430/905; 430/913; 430/914; 430/311

(58) Field of Classification Search ........... 430/270.1, 430/280.1, 286.1, 905, 913, 914, 311
See application file for complete search history.

(56) References Cited

U.S. PATENT DOCUMENTS 4,031,036 A * 6/1977 Koshar ...................... 526/220

(Continued)

FOREIGN PATENT DOCUMENTS

JP          8027102           1/1996

(Continued)

OTHER PUBLICATIONS

Japanese Office Action for corresponding Japanese patent application No. 2002-369145; date of mailing Apr. 20, 2007.

(Continued)

*Primary Examiner*—Amanda C. Walke
(74) *Attorney, Agent, or Firm*—Myers, Bigel, Sibley & Sajovec, P.A.

(57) ABSTRACT

The invention provides a high-resolution resist material comprising an acid generator that has high sensitivity and high resolution with respect to high-energy rays of 300 nm or less, has small line-edge roughness, and is superior in heat stability and in shelf stability, and provides a pattern forming method that uses this resist material. The invention further provides a chemically amplified positive resist material comprising a base resin, an acid generator and a solvent in which the acid generator generates an alkylimidic acid containing a fluorine group, and provides a pattern forming method comprising a step of applying the resist material to the substrate, a step of performing exposure to a high-energy ray of a wavelength of 300 nm or less through a photomask following heat treatment, and a step of performing development by a developing solution following heat treatment.

17 Claims, 2 Drawing Sheets

18nm   25nm   30nm   35nm

40nm   50nm   60nm   70nm

Si base

U.S. PATENT DOCUMENTS

| | | | | |
|---|---|---|---|---|
| 4,387,222 A | * | 6/1983 | Koshar | 544/4 |
| 4,429,093 A | * | 1/1984 | Koshar | 526/205 |
| 5,541,235 A | * | 7/1996 | Busman et al. | 522/25 |
| 5,585,507 A | | 12/1996 | Nakano et al. | 556/7 |
| 5,635,332 A | | 6/1997 | Nakano et al. | 430/270.1 |
| 5,744,537 A | | 4/1998 | Brunsvold et al. | 524/520 |
| 6,004,721 A | * | 12/1999 | Tan et al. | 430/270.1 |
| 6,013,411 A | * | 1/2000 | Aoai et al. | 430/270.1 |
| 6,048,661 A | * | 4/2000 | Nishi et al. | 430/270.1 |
| 6,545,109 B2 | * | 4/2003 | Lamanna et al. | 526/220 |
| 6,803,173 B2 | * | 10/2004 | Uenishi et al. | 430/270.1 |
| 2003/0052310 A1 | * | 3/2003 | Michot et al. | 252/500 |
| 2003/0207201 A1 | * | 11/2003 | Hatakeyama et al. | 430/270.1 |
| 2004/0033366 A1 | * | 2/2004 | Lamanna et al. | 428/421 |
| 2004/0072094 A1 | * | 4/2004 | Shima et al. | 430/270.1 |

FOREIGN PATENT DOCUMENTS

| | | | |
|---|---|---|---|
| JP | | 10319581 | 12/1998 |
| JP | | 2002-268223 A | 9/2002 |
| JP | | 2002-341539 A | 11/2002 |
| JP | | 2003-057816 A | 2/2003 |
| JP | | 2003-140331 A | 5/2003 |
| JP | | 2003-246786 A | 9/2003 |
| JP | | 2004062154 A | * 2/2004 |

OTHER PUBLICATIONS

English translation of Japanese Office Action for corresponding Japanese patent application No. 2002-369145; date of mailing Apr. 20, 2007.

* cited by examiner

PHOTOACID GENERATING COMPOUNDS, CHEMICALLY AMPLIFIED POSITIVE RESIST MATERIALS, AND PATTERN FORMING METHOD

CROSS-REFERENCE TO RELATED APPLICATIONS

The present application is a continuation in part application of U.S. patent application Ser. No. 10/331,785 filed Dec. 27, 2002 now abandoned which claims priority to Japanese Patent Application No. 2001-397192, filed Dec. 27, 2001, the disclosures of which are incorporated herein by reference in their entireties.

BACKGROUND OF THE INVENTION

1. Field of the Invention

This invention relates to an onium salt that generates an alkylimidic acid containing a specific fluorine group, a resist material for exposure to high-energy rays shorter than 300 nm in wavelength characterized by containing the onium salt, and a pattern forming method that uses the resist material.

2. Description of the Related Art

In recent years, integration and operating speeds have been further improved in LSI devices, and, correspondingly, miniaturization of a pattern rule has been sought. As such, far ultraviolet ray lithography and vacuum ultraviolet ray lithography are promising as next-generation microfabrication techniques.

Advanced semiconductors of a 0.15 μm rule are presently manufactured by photolithography using an KrF excimer laser, and, in addition, those of a 0.13 μm rule are about to come under production. Photolithography in which an ArF-excimer laser beam is used as a light source is regarded as a technique indispensable for hyperfine fabrication of not more than 0.13 μm, and it is greatly hoped that photolithography will be achieved.

Especially in photolithography in which the ArF excimer laser beam is used as a light source, a highly sensitive resist material capable of exhibiting sufficient resolution with less exposure is sought in order to prevent a precise, expensive optical material from deteriorating. The most common measure for realizing a highly sensitive resist material is to select highly transparent materials in a wavelength of 193 nm. For example, a poly(meth)acrylic acid and a derivative thereof, a norbornene-maleic anhydride alternating polymer, polynorbornene, and a metathesis polymer by ring-opening polymerization, etc., have been proposed with regard to a base resin, and, due to the fact that the transparency of a resin alone is heightened, a certain degree of success has been obtained. However, with regard to an acid generator, a rise in transparency causes a decrease in acid generation-efficiency, and, as a result, causes a low sensitivity or a lack of heat stability and shelf stability. Therefore, in the present state, a sufficiently practical acid generator has not-yet been obtained.

An alkylsulfonium salt, which is proposed in, for example, Japanese Patent Provisional Publication Nos. 7-25846/1995 (U.S. Pat. Nos. 5,585,507 and 5,635,332), 7-28237/1995 (U.S. Pat. Nos. 5,585,507 and 5,635,332), and 8-27102/1996, is not preferable because the salt has neither sufficient acid generation efficiency nor sufficient heat stability although the salt has very high transparency. An alkylarylsulfonium salt, which is proposed in Japanese Patent Provisional Publication No. 10-319581/1998, etc., is superior in balance between transparency and acid generation efficiency and is high in sensitivity, but lacks both heat stability and shelf stability. An arylsulfonium salt, which has been effective in photolithography using an KrF excimer laser beam, is superior in acid generation efficiency, in heat stability, and in shelf stability, but is extremely low in transparency, so that a pattern after being developed is severely tapered. Although there is a possible measure in which transparency is supplemented by thinning the film of a resist, this measure is not suitable as a pattern forming method because it markedly lowers the etching resistance of the resist film.

These publications chiefly describe a case where the structure on the cation side of the onium salt is changed, and it has been reported that, in resolution and pattern shape, a close relationship exists between the kind of generated acid and the kind of an acid-labile group (i.e., group unstable to an acid). Many reports have been published regarding examinations in which the kind of acid is changed in, for example, a resist of polyhydroxystyrene and a polyhydroxystyrene/(meth)acrylate copolymerization base for KrF lithography. For example, U.S. Pat. No. 5,744,537 discloses that an excellent pattern shape can be obtained when an acid generator that generates a camphorsulfonic acid is added. However, in a polymer for ArF having an alicyclic structure, acid-elimination reactivity is low, and the eliminatin reaction does not advance in the camphorsulfonic acid even if it is the same as polyhydroxystyrene and a polyhydroxystyrene/(meth)acrylate copolymer acid-elimination group. Herein, (meth)acrylate denotes methacrylate and/or acrylate.

On the anion side of the onium salt, a fluorinated alkylsulfonic acid having high acidity is chiefly applied. The fluorinated alkylsulfonic acid includes trifluoromethanesulfonic acid, a nonafluorobutanesulfonic acid and a hexadecafluorooctanesulfonic acid. Additionally, an arylsulfonic acid that has undergone fluorine substitution or fluorine alkyl substitution can be included. In greater detail, examples thereof include a 4-fluorobenzenesulfonic acid, a 3-benzenesulfonic acid, a 2-benzenesulfonic acid, a 2,4-difluorobenzenesulfonic acid, a 2,3-difluorobenzenesulfonic acid, a 3,4-difluorobenzenesulfonic acid, a 2,6-difluorobenzenesulfonic acid, a 3,5-difluorobenzenesulfonic acid, a 2,3,4-trifluorobenzenesulfonic acid, a 3,4,5-trifluorobenzenesulfonic acid, a 2,4,6-trifluorobenzenesulfonic acid, a 2,3,4,5,6 pentafluorobenzenesulfonic acid, a 4-trifluoromethylbenzenesulfonic acid, a 5-trifluoromethylbenzenesulfonic acid, a 6-trifluoromethylbenzenesulfonic acid, and a 4-trifluoromethylnaphthyl-2-sulfonic acid.

On the other hand, line-edge roughness and a dimensional difference (I/G bias) between a sparse pattern and a dense pattern have been to-be-solved matters correspondingly with the advancement of microfabrication. It is conventionally well known that a dimensional difference arises between a dense pattern and a sparse pattern after being developed even if they have the same dimensions on a mask. This problem is critical especially in a dimension exceeding a wavelength. The reason is because they differ in optical strength resulting from a difference in optical interference in the image formation of the dense pattern and the sparse pattern.

For example, FIG. 1 shows a pitch of a repetitive line of 0.18 microns, which is indicated by the horizontal axis, and a length of the line corresponding to the changing pitch, which is indicated by a vertical axis, under an optical condition that the wavelength is 248 nm, NA is 0.6, and σ is 0.75. The size of an optical image is temporarily thinned and becomes thicker as the pitch becomes larger when specifications are formed so that a line length becomes 0.18 microns in a 0.36-micron pitch (0.18-micron line and 0.18-micron space). The result of a resist line length calculated after being developed is also shown. The resist size and the optical-image size are shown by use of simulation software PROLITH2 Ver.6.0, which is sold by KLA-Tencor Corporation (former Finle Technologies Inc.). The resist size is thinned correspondingly with the enlargement of the pitch, and is further thinned correspondingly with an increase in acid diffusion.

The problem of sparseness/denseness dependence in which the size of the sparse pattern becomes thinner than that of the dense pattern has become a growing concern. It can be understood from the aforementioned simulation result that a method for reducing acid diffusion is effective as a method for reducing the sparseness/denseness dependence.

However, disadvantageously, ruggedness or surface roughening will occur because of a standing wave in a sidewall of a resist pattern after being developed, or line-edge roughness will become large if the acid diffusion is excessively reduced. For example, FIG. 2 shows a calculation result of a resist cross-sectional shape of a 0.18 μm-line-and-space pattern obtained when an acid-diffusion distance is changed on an Si base by use of the simulation software PROLITH Ver. 6.0 of KLA-Tencor Corporation.

It is shown that the ruggedness in the sidewall caused by the standing wave becomes prominent in proportion to a decrease in the acid diffusion distance. A similar tendency is also shown with regard to the line-edge roughness observed from above SEM. That is, the line-edge roughness increases in proportion to a reduction in the acid diffusion. A general method to reduce the line roughness is to increase the acid diffusion distance, but it is impossible to further improve sparseness/denseness dependence according to this method.

In FIG. 1, a dimensional difference between a dense pattern with a small pitch and a sparse pattern with a large pitch becomes large in proportion to an increase in the acid diffusion distance. That is, it is shown that the sparseness/denseness dependence becomes great. A reduction in the line-edge roughness and a reduction in the sparseness/denseness dependence stand in a trade-off relationship, and it can be considered that it is difficult for them to coexist easily.

A method for improving a light contrast can be mentioned as a method for improving line-edge roughness. For example, the line-edge roughness is lowered in proportion to an increase in line width if an exposure wavelength is the same. In the case of a repetitive pattern, off-axis illumination (e.g., annular illumination and quadrupole illumination) and a phase-shift mask have smaller line-edge roughness in proportion to an increase in NA of a stepper than normal illumination and a normal Cr mask, respectively, even if the exposure wavelength is the same, and even if the dimensions are the same. There is a correlation between the optical contrast of the line edge of a pattern and the line-edge roughness, and the line-edge roughness is reduced as the optical contrast of the line edge becomes steeper. In the exposure wavelength, shorter-wavelength exposure is expected to have smaller line-edge roughness. However, there is a report that ArF exposure should have a higher optical contrast and smaller line-edge roughness because of its shorter wavelength, although, in practice, KrF exposure is superior to ArF exposure in comparison to the line-edge roughness in KrF exposure and that in ArF exposure (SPIE 3999,264(2001)). This results from a performance difference between the resist material of KrF and that of ArF, and this indicates that line-edge roughness caused especially by the material in ArF exposure is a serious problem. Therefore, there is a demand to produce an acid generator that does not worsen sparseness/denseness dependence while improving line-edge roughness.

SUMMARY OF THE INVENTION

The present invention has been made in consideration of the foregoing circumstances. It is therefore an object of the present invention to provide a new acid generator that has high sensitivity and high resolution with respect to high-energy rays of 300 nm or less, that has small line-edge roughness, and that is superior in heat stability and in shelf stability, and provide a high-resolution resist material that contains this acid generator, and provide a pattern forming method that uses this resist material.

In order to achieve the object, the present inventor has actively conducted investigations. As a result, the present inventors have found that a sulfonium salt or an iodonium salt, which generates an alkylimidic acid containing a fluorine group and, preferably, shown by the following General Formula (1) or (2), has high sensitivity with respect to high-energy rays of 300 nm or less and has sufficient heat stability and shelf stability, and has found that a chemically amplified positive resist material with which this salt is mixed has high resolution and can improve line-edge roughness and sparseness/denseness dependence, so that it can have an excellent effect on precise microfabrication.

That is, the present invention provides a photoacid-generating compound shown by General Formula (1).

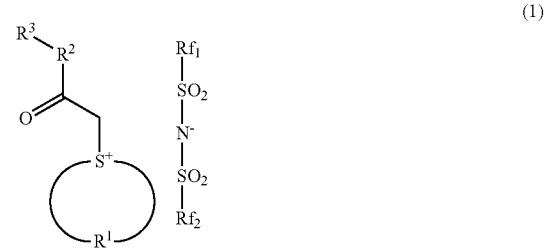

wherein $R^1$ is an alkylene group of 2 to 8 carbon atoms; $R^2$ is a single bond, an oxygen atom, a nitrogen atom or an alkylene group of 1 to 4 carbon atoms; $R^3$ is a straight-chained, branched, or cyclic alkyl group having 1 to 8 carbon atoms, or is an aryl group having 6 to 10 carbon atoms and $R^3$ may be substituted with an alkyl group having 1 to 4 carbon atoms, a fluorinated alkyl group having 1 to 4 carbon atoms, an alkoxy group having 1 to 4 carbon atoms, a fluorinated alkoxy group having 1 to 4 carbon atoms, a nitro group, a cyano group, a fluorine atom, a phenyl group, a substituted phenyl group, an acetyl group, or a benzoyloxy group; either of or both of $Rf_1$ and $Rf_2$ are straight-chained, branched or cyclic alkyl groups, each having 1 to 20 carbon atoms containing at least one fluorine atom, and may comprise a hydroxyl group, a carbonyl group, an ester group, an ether group or an aryl group; when only one of $Rf_1$ and $Rf_2$ is the straight-chained, branched or cyclic alkyl group, having 1 to 20 carbon atoms containing at least one fluorine atom, the other thereof is a straight-chained, branched or cyclic alkyl group, having 1 to 20 carbon atoms, and may comprise a hydroxyl group, a carbonyl group, an ester group, an ether group or an aryl group; and $Rf_1$ and $Rf_2$ may be bonded together and form a ring.

The present invention further provides a chemically amplified positive resist material, which comprises a base resin, an acid generator and a solvent, wherein the acid generator generates an alkylimidic acid containing a fluorine group, and provides a pattern forming method comprising a step of applying the resist material to a substrate, a step of performing exposure to a high-energy ray of a wavelength of 300 nm or less through a photomask after being subjected to heat treatment, and a step of carrying out development by use of a developing solution after being subjected to heat treatment.

The resist material to which the acid generator of the present invention has been added is superior especially in resolution, having a small dimensional difference between a sparse pattern and a dense pattern, and having small line-edge roughness.

DETAILED DESCRIPTION OF THE PREFERRED EMBODIMENTS

Figure 1:
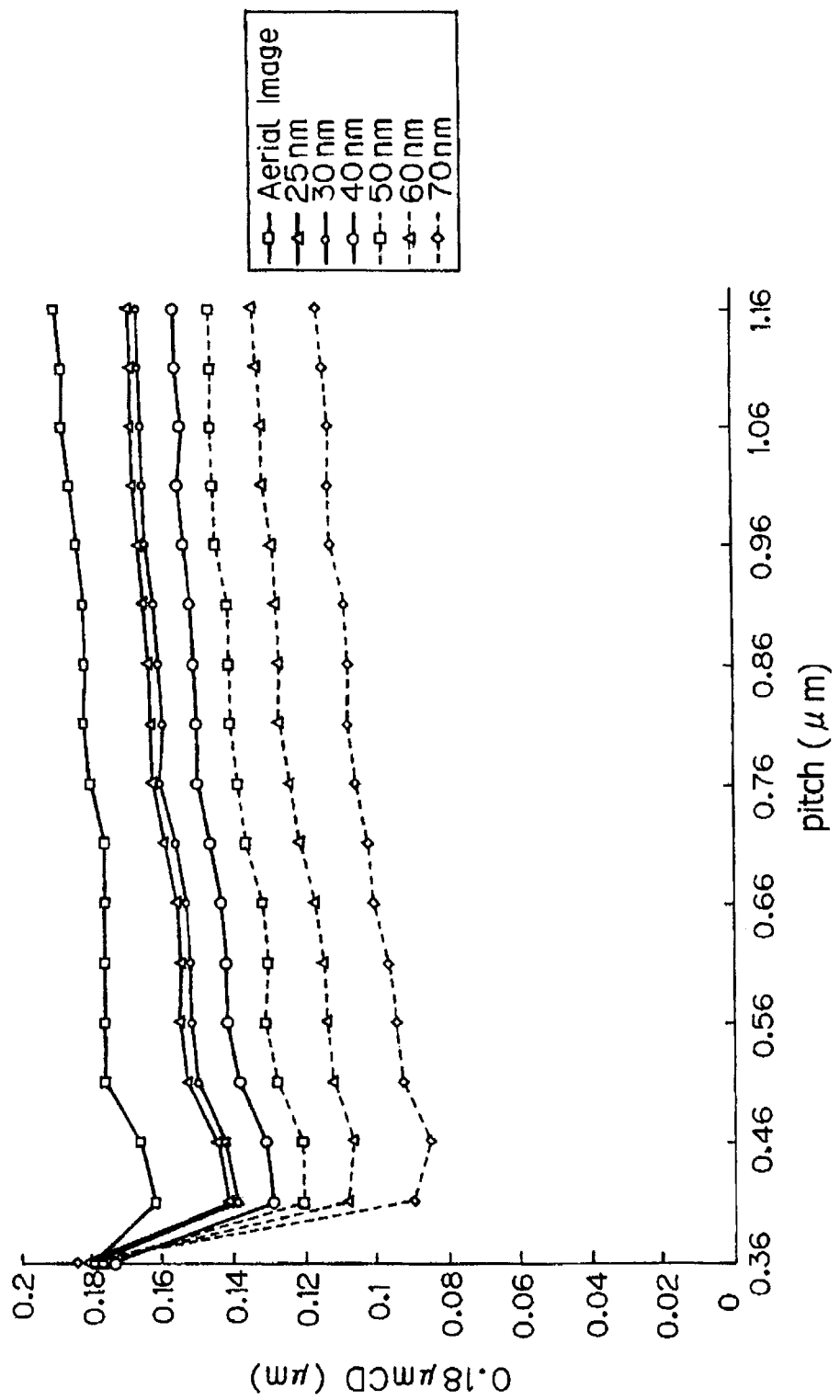
FIG. 1 shows a calculation result of a simulation showing a change in a line length obtained when a line pitch and an acid diffusion distance are changed, in which 25 to 70 nm denotes the acid diffusion distance.
Figure 2:
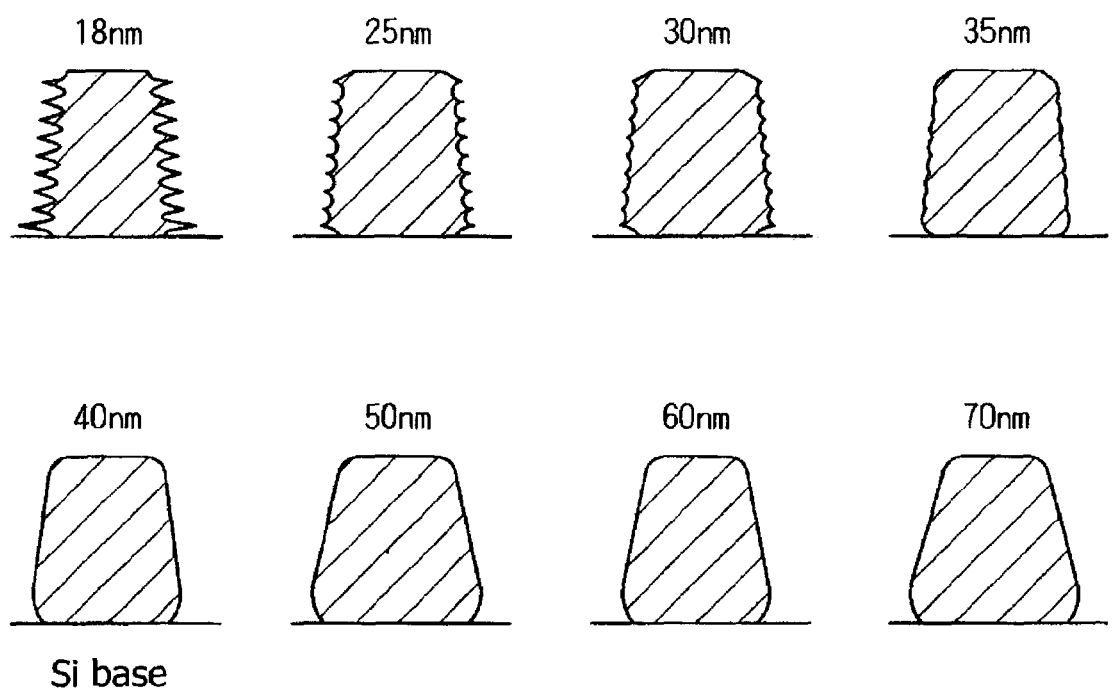
FIG. 2 shows a calculation result of a simulation of a resist cross-sectional shape obtained when the acid diffusion distance is changed to 18 to 70 nm.

The present invention will hereinafter be described in greater detail.

An acid generator used in the present invention generates an alkylimidic acid containing a fluorine group, and, preferably, it is an onium salt shown by General Formula (1) shown above or General Formula (2) shown below.

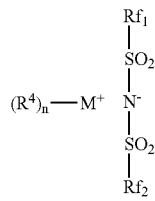

(2)

In General Formula (1), $R^1$ is preferably an alkylene group having 4 or 5 carbon atoms. In General Formula (1), $R^3$ is preferably a phenyl group or a naphthyl group.

In General Formula (1) or (2), either of or both of $Rf_1$ and $Rf_2$ are straight-chained, branched or cyclic alkyl groups, each having 1 to 20 carbon atoms containing at least one fluorine atom, and may comprise a hydroxyl group, a carbonyl group, an ester group, an ether group, or an aryl group When only one of $Rf_1$ and $Rf_2$ is the straight-chained, branched or cyclic alkyl group, having 1 to 20 carbon atoms containing at least one fluorine atom, the other thereof is a straight-chained, branched or cyclic alkyl group, having 1 to 20 carbon atoms, and may comprise a hydroxyl group, a carbonyl group, an ester group, an ether group, or an aryl group. The $Rf_1$ and $Rf_2$ may be bonded together and form a ring. The $R^1$, which may be the same or different, represents a straight-chained, branched or cyclic alkyl group having 1 to 12 carbon atoms which may comprise a carbonyl group, an ester group, an ether group, a thioether group, or a double bond. Alternatively, $R^1$ represents an aryl group having 6 to 12 carbon atoms or an aralkyl group having 7 to 20 carbon atoms. The $M^+$ represents iodonium or sulfonium, and n is 2 or 3.

An anion part in General Formula. (1) or (2) is an alkylimide anion containing a fluorine group, and various combinations can be created by changing the combination of $Rf_1$ and $Rf_2$. Although all of them cannot be shown, one example is as follows.

(1)-1

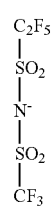

(1)-2

(1)-3

(1)-4

(1)-5

(1)-6

-continued
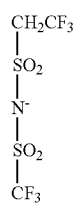
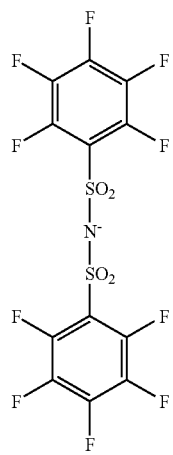
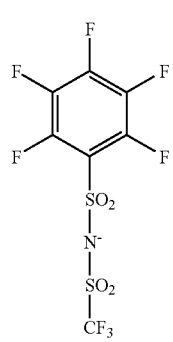
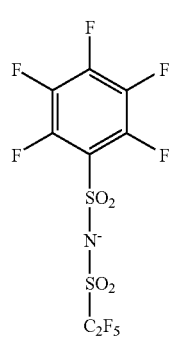
(1)-7
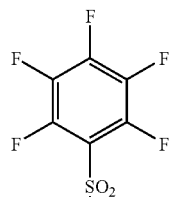
(1)-8
(1)-9
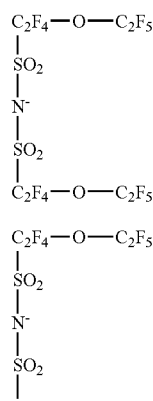
(1)-10
(1)-11
-continued
(1)-12
(1)-13
(1)-14
(1)-15
(1)-16
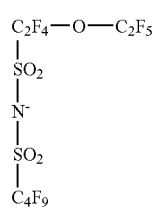
(1)-17
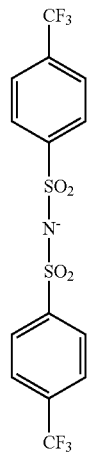

-continued
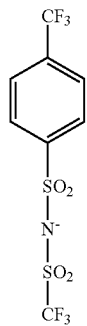 (1)-18
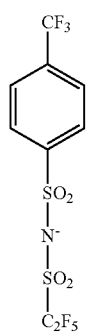 (1)-19
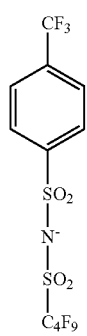 (1)-20
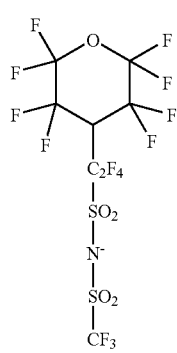 (1)-21
-continued
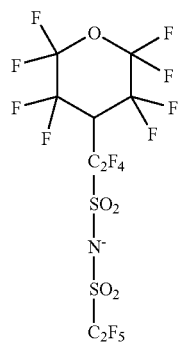 (1)-22
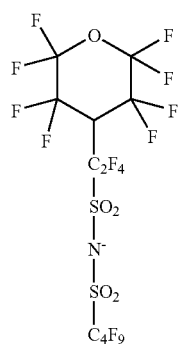 (1)-23
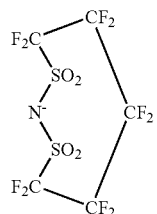 (1)-24
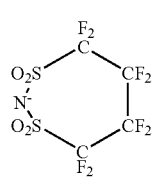 (1)-25
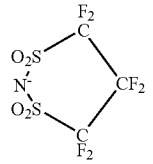 (1)-26
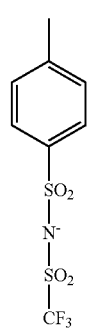 (1)-27

-continued (1)-28
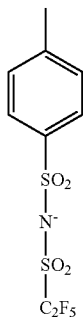

(1)-29
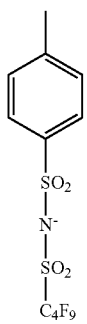

(1)-30
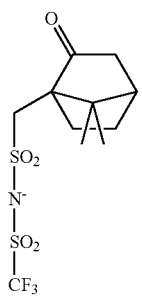

(1)-31
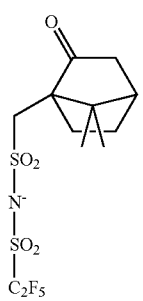

(1)-32
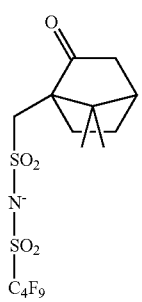

Generally, an acid diffusion distance may be controlled by the control of the molecular weight of a generated acid. For example, an acid generator that generates a sulfonic acid in which the chained length of a perfluoroalkyl group is short is added to lengthen the acid diffusion distance, and, in contrast, an acid generator that generates a sulfonic acid in which the chained length of a perfluoroalkyl group is long is added to shorten the acid diffusion distance. However, in a perfluoroalkylsulfonic acid or a perfluoroarylsulfonic acid that has been conventionally used, the acid diffusion distance is controlled by the length of a single alkyl group or a single aryl group, and therefore it has been difficult to strictly control the acid diffusion distance. However, since an alkylimidic acid containing a fluorine group mentioned in the present invention has two alkyl groups, the two alkyl groups having chain lengths which differ from each other can be variously combined, and the acid diffusion distance can be strictly controlled. Additionally, it has been found that the fluorine-group-containing alkylimidic acid is apt to have a shorter acid diffusion distance than the perfluoroalkylsulfonic acid even if they are the same in alkyl chain length.

The onium-salt compound shown in General Formula (1) includes the following examples.

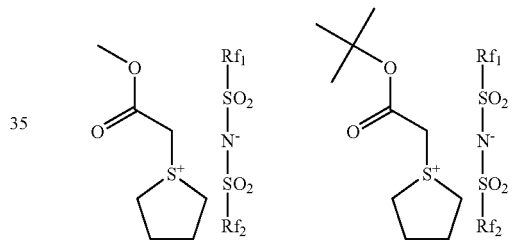

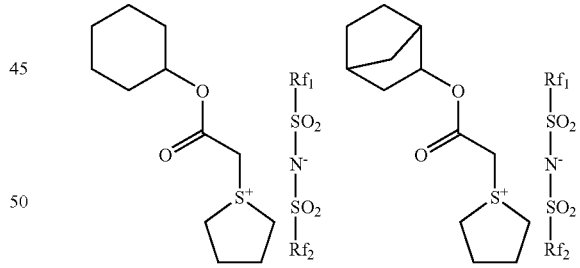

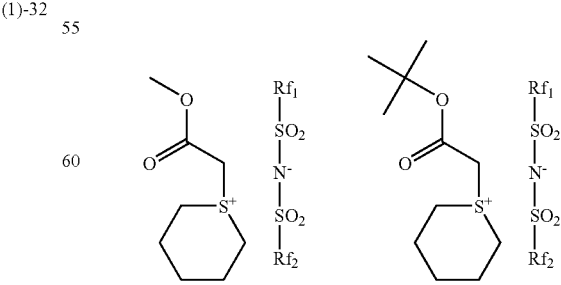

-continued
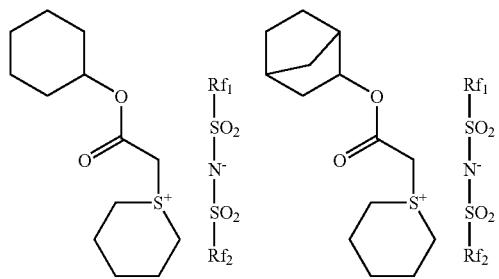
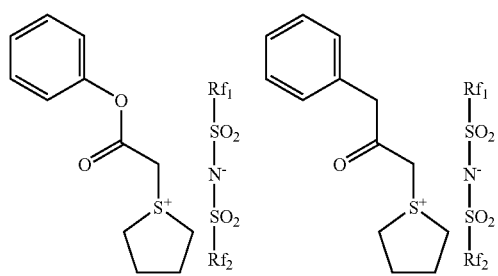
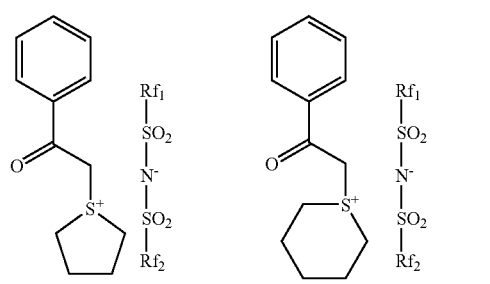
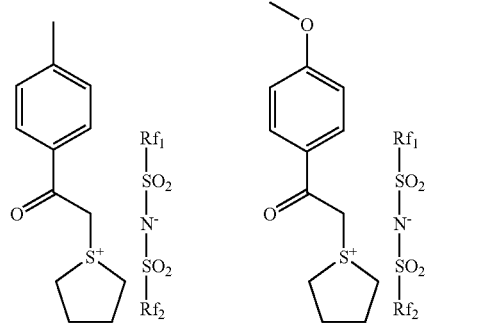
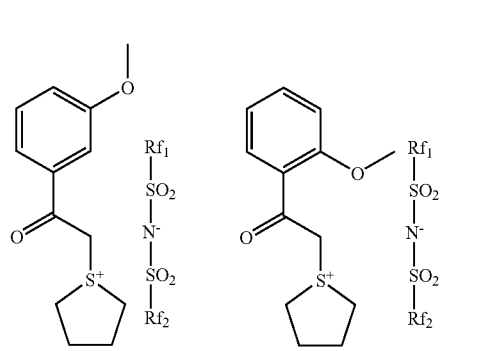
-continued
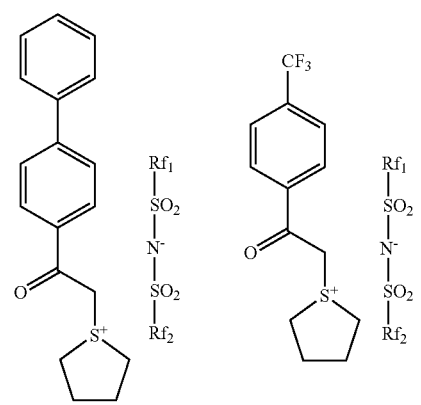
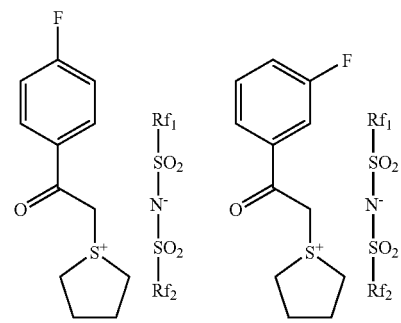
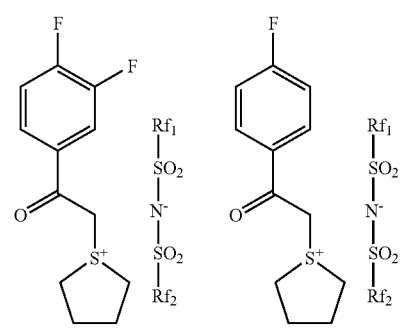
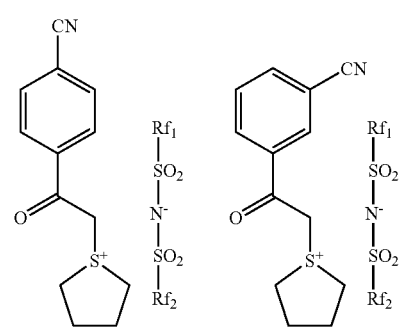

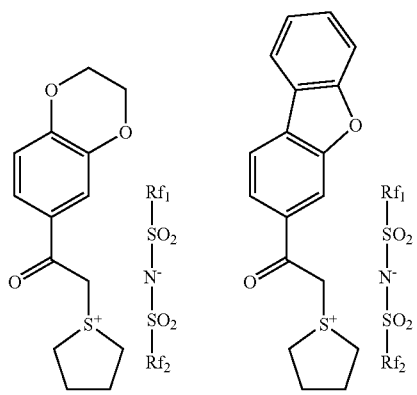
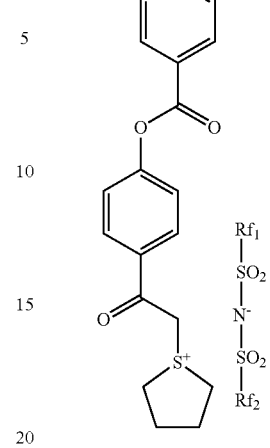
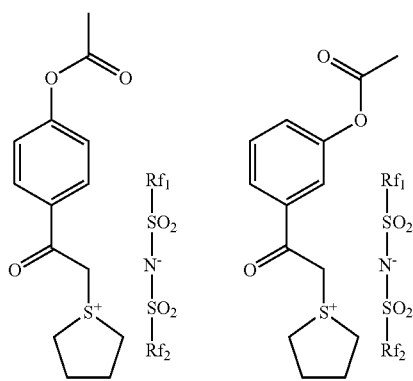
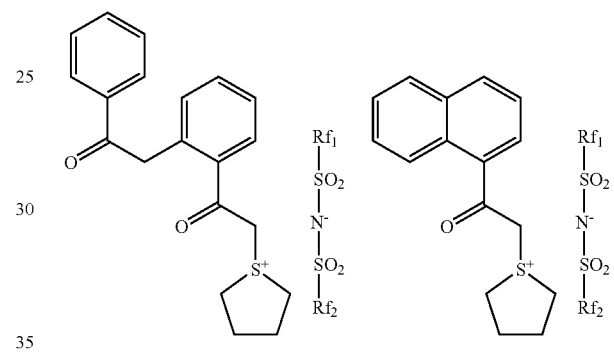
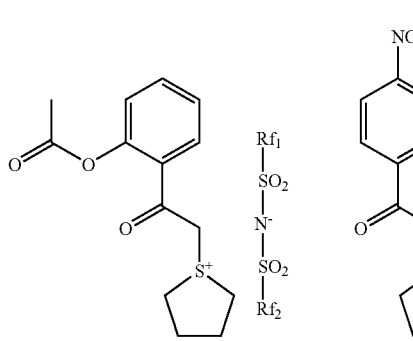
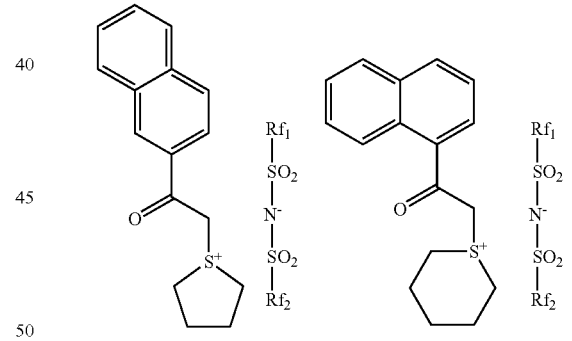
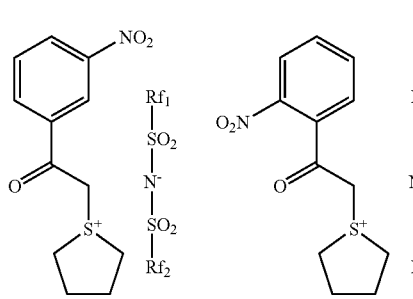
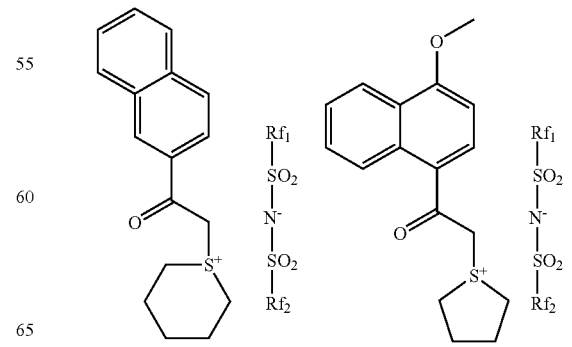

-continued

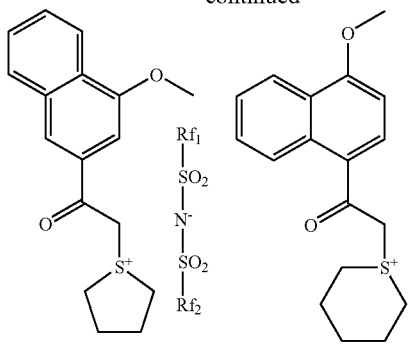

The onium salt of the present invention limits the structure of a generated acid, i.e., limits the anion side, and does not specifically limit the cation side. The M of General Formula (2) includes a sulfur atom and an iodine atom and General Formula (2) can be shown in the form of General Formula (2)-s and General Formula (2)-i. A specific structure is as follows.

[F7]

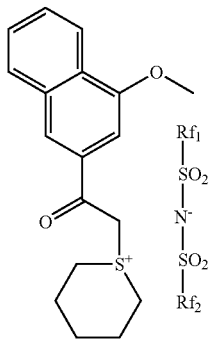

Herein, $R^5$, $R^6$ and $R^7$, which may be same or different, are each independently a straight-chained, branched or cyclic alkyl group having 1 to 20 carbon atoms, an aryl group, or an aralkyl group. A pair of $R^5$ and $R^6$, a pair of $R^6$ and $R^7$, and a pair of —$R^5$ and $R^7$ may be each bonded together to form a ring. $R^8$ and $R^9$, which may be same or different, are each independently an aryl group having 6 to 20 carbon atoms, The $R^8$ and $R^9$ may be bonded together and form a ring.

A specific structure of General Formula (2)-s includes the following.

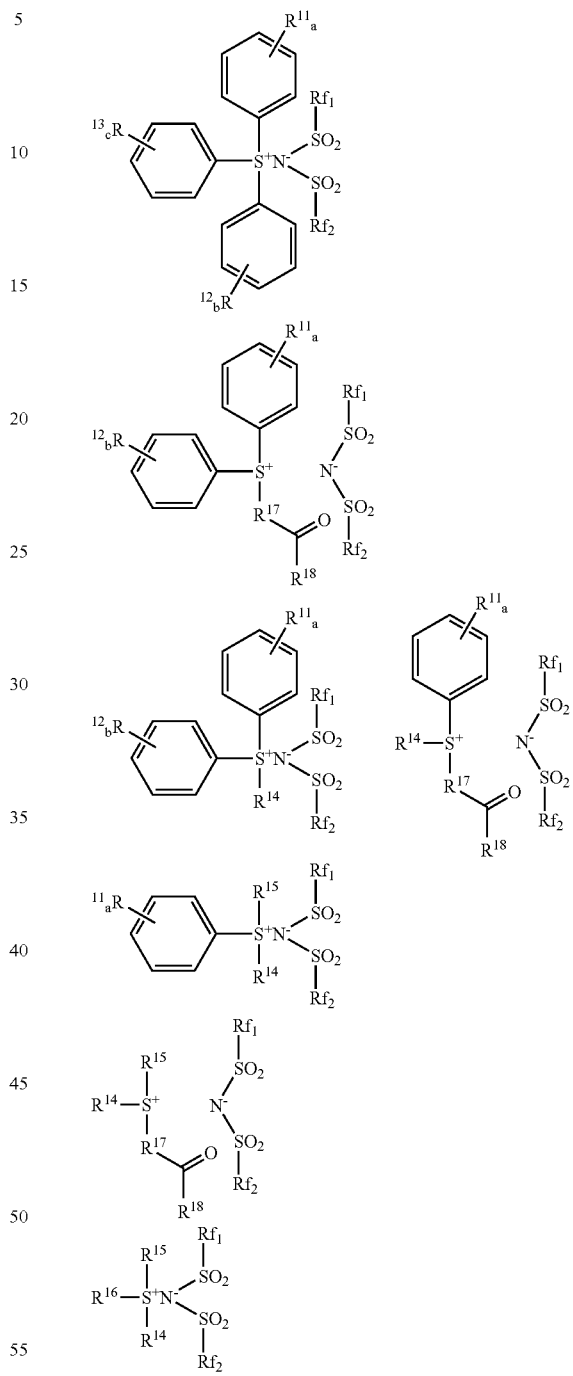

Herein, $R^{11}$, $R^{12}$, and $R^{13}$ are each independently a hydrogen atom, a halogen atom, a straight-chained, branched or cyclic alkyl group having 1 to 20 carbon atoms, a straight-chained, branched or cyclic alkoxy group having 1 to 20 carbon atoms or an aryl group having 6 to 20 carbon atoms, or, alternatively, are each independently a straight-chained, branched or cyclic alkyl group having 1 to 20 carbon atoms and may comprise an ester group, a carbonyl group or a lactone ring. $R^{14}$, $R^{15}$, and $R^{16}$ are each independently a straight-chained, branched or cyclic alkyl group having 1 to 10 carbon atoms, and may comprise a carbonyl group, an ester group or a lactone ring. $R^{17}$ is a methylene group. $R^{18}$ is a straight-chained, branched or cyclic alkyl group having 1 to 10 carbon atoms. $R^{17}$ and $R^{18}$ may be bonded together and form a ring, a, b, and c are each independently an integer selected from 0 to 5.
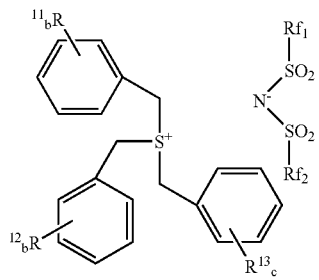
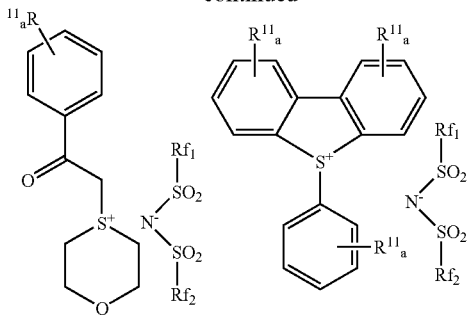
-continued
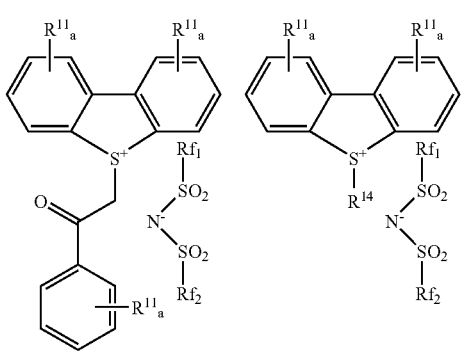
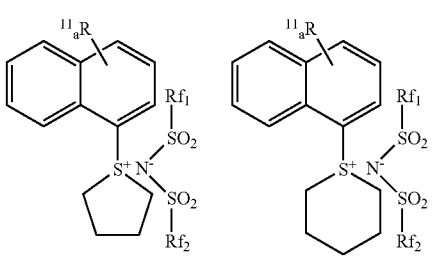
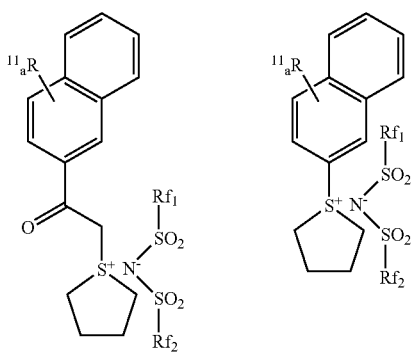
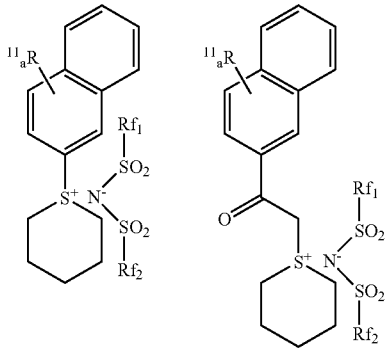

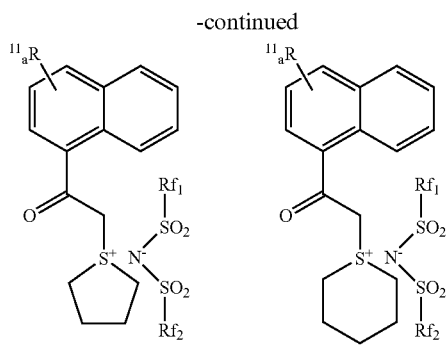
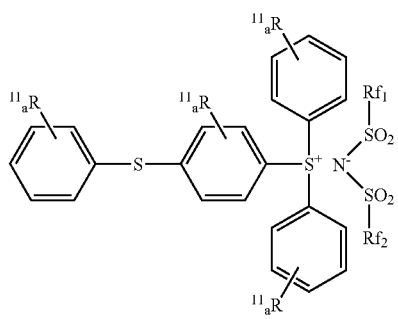
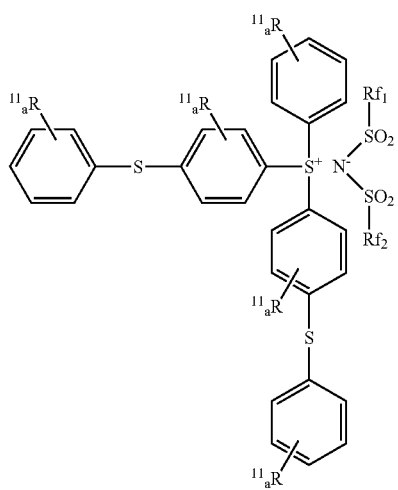

A specific structure of General Formula (2)-i includes the following.

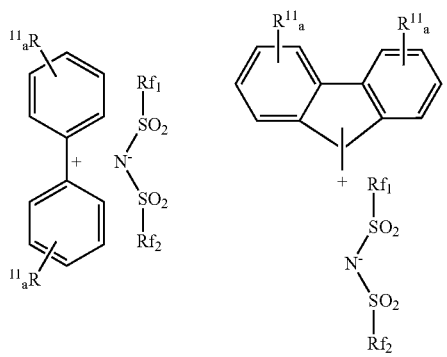
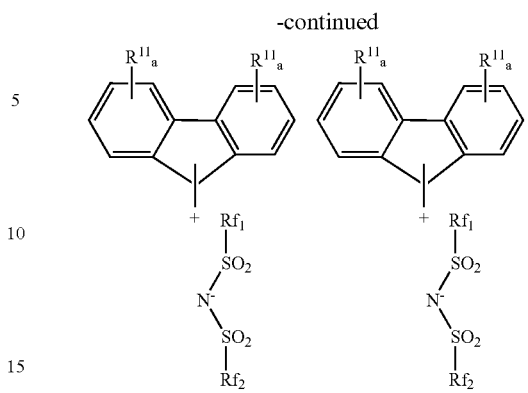

A synthetic method for a sulfonium salt mentioned in General Formula (1) is shown by, for example, a reaction (Step 1) between a thiophene compound and an acetyl bromide compound and an ion-exchange reaction (Step 2). In Step 1, the reaction in nitromethane at room temperature with stirring may end in several hours. The thiophene compound and the acetyl bromide compound may have the same mole amount. An obtained compound 1 may be washed with diethyl ether and water, and may be extracted to an aqueous phase. Thereafter, an imidic acid-containing a fluorine group may be added to the compound 1 in a ratio of equal mole, and dichloromethane or chloroform may be then added thereto. An anion exchange may be then carried out while stirring it at room temperature for several minutes to several tens of minutes, and the organic phase of a final compound may be extracted. The organic phase may be concentrated, then crystallized by diethyl ether for purification, thus obtaining the final compound.

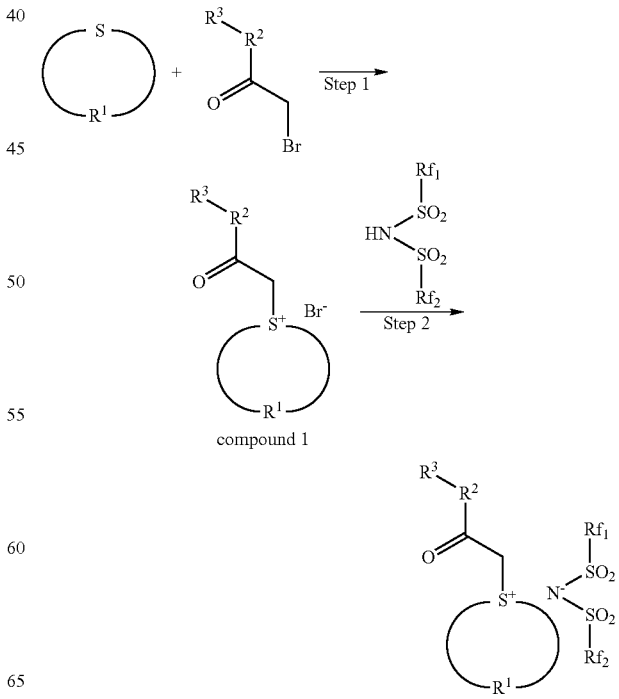

The onium salt in Formula (1) or (2) may be compounded preferably at a rate of 0.1 to 15 parts by weight, specifically 0.5 to 10 parts by weight, per 100 parts by weight of the base resin. A too low compounding ratio thereof may bring about a decrease in sensitivity, and a too high compounding ratio thereof may bring about a decrease in transparency, thereby lowering the resolution of the resist material.

Preferably, the base resin used in the present invention is insoluble or slightly soluble in a developing solution, and becomes soluble in the developing solution depending on an acid. In the state of being insoluble or slightly soluble in the developing solution, the solubility thereof with respect to an aqueous solution of 2.38 wt % TMAH (tetramethylammonium hydroxide) is 0 to 20 Å/second, and, in the state of being soluble in the developing solution, the solubility is 20 to 300 Å/second.

Examples of the base resin used for the chemically amplified positive resist material of the present invention may be one or more polymers selected from a group consisting of polyhydroxystyrene and a derivative of polyhydroxystyrene wherein hydroxyl groups thereof are partially or entirely substituted with a acid-labile group; a poly(meth)acrylic acid and an ester thereof (including a copolymer of acrylic acid and methacrylic acid and an ester of the copolymer); a copolymer of cycloolefin and maleic anhydride; a copolymer of cycloolefin, maleic anhydride and acrylate; a copolymer of cycloolefin, maleic anhydride and methacrylate; a copolymer of cycloolefin, maleic anhydride, acrylate and methacrylate; a copolymer of cycloolefin and maleimide; a copolymer of cycloolefin, maleimide and acrylate; a copolymer of cycloolefin, maleimide and methacrylate; a copolymer of cycloolefin, maleimide, acrylate and methacrylate; polynorbornene; and a metathesis polymer by ring-opening polymerization.

Preferable examples of the base resin used in the present invention are polyhydroxystyrene (PHS), and a copolymer of styrene and hydroxystyrene wherein hydroxyl groups thereof are partially or entirely substituted with an acid-labile group, a copolymer of hydroxystyrene and (meth) acrylate and a copolymer of hydroxystyrene and maleimide-N-carboxylate, which are suitable for a resist for the KrF excimer laser; poly(meth)acrylate, an alternating copolymer of norbornane and maleic anhydride, an alternating copolymer of tetracyclododecene and maleic anhydride, polynorbornenes, and a metathesis polymer by ring-opening polymerization, which are suitable for a resist for the ArF excimer laser. However, the base resin is not limited to these polymers. In a positive resist, generally, the dissolution rate of a non-exposure part may be lowered by substituting the hydroxyl group of a phenol or carboxyl group with an acid-labile group. Various groups can be selected as the acid-labile group in the base polymer. Preferably, they are groups especially of Formulas (AL 10) and (AL 11) shown below, a tertiary alkyl group having 4 to 40 carbon atoms of Formula (AL 12) shown below, a trialkylsilyl group having 1 to 6 carbon atoms, and an oxoalkyl group having 4 to 20 carbon atoms. Herein, the (meth)acrylic acid denotes a methacrylic acid and/or an acrylic acid.

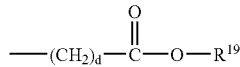

(AL10)

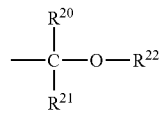

(AL11)

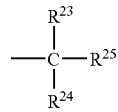

(AL12)

In Formulas (AL 10) and (AL 11), $R^{19}$ and $R^{22}$ are independently each a straight-chained, branched or cyclic alkyl group having 1 to 20 carbon atoms, and may comprise a hetero atom such as oxygen, sulfur, nitrogen and fluorine. $R^{20}$ and $R^{21}$ are each independently a hydrogen atom or a straight-chained, branched or cyclic alkyl group having 1 to 20 carbon atoms, and may comprise a hetero atom such as oxygen, sulfur, nitrogen and fluorine. The d is an integer selected from 0 to 10. A pair of $R^{20}$ and $R^{21}$, a pair of $R^{20}$ and $R^{22}$ and a pair of $R^{21}$ and $R^{22}$ may be each bonded together to form a ring.

Specific examples of compounds shown in Formula (AL 10) include a tert-butoxycarbonyl group, a tert-butoxycarbonylmethyl group, a tert-amyloxycarbonyl group, a tert-amyloxycarbonylmethyl group, a 1-ethoxyethoxycarbonylmethyl group, a 2-tetrahydropyranyloxycarbonylmethyl group, a 2-tetrahydrofuranyloxycarbonylmethyl group, etc. Additionally, substituents of General Formulas (AL 10)-1 to (AL 10)-10 shown below may be included.

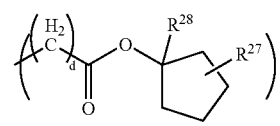

(AL10)-1

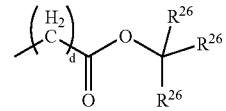

(AL10)-2

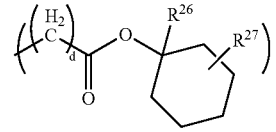

(AL10)-3

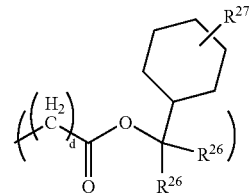

(AL10)-4

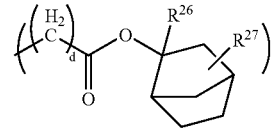

(AL10)-5

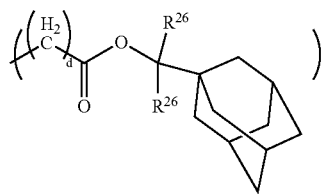 (AL10)-6

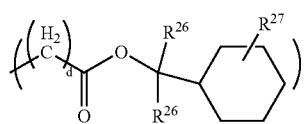 (AL10)-7

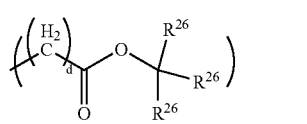 (AL10)-8

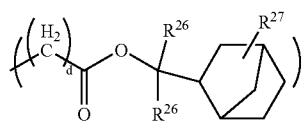 (AL10)-9

In Formulas (AL 10)1 to (AL 10)-10, $R^{26}$, which may be same or different, is independently a straight, branched or cyclic alkyl group having 1 to 8 carbon atoms, or an aryl or aralkyl group having 6 to 20 carbon atoms. $R^{27}$ does not exist or is a straight, branched-chain or cyclic alkyl group having 1 to 20 carbon atoms. $R^{28}$ is an aryl or aralkyl group having 6 to 20 carbon atoms. The d is an integer selected from 0 to 6.

An acetal compound of Formula (AL 11) includes (AL 11)-1 to (AL 11)-23.

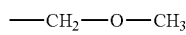 (AL11)-1

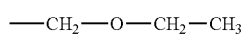 (AL11)-2

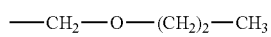 (AL11)-3

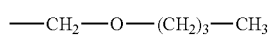 (AL11)-4

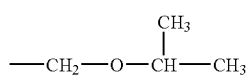 (AL11)-5

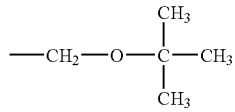 (AL11)-6

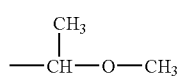 (AL11)-7

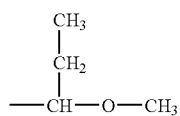 (AL11)-8

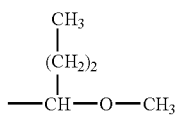 (AL11)-9

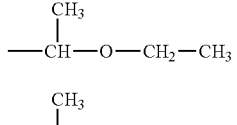 (AL11)-10

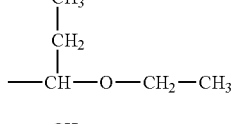 (AL11)-11

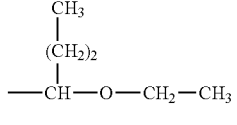 (AL11)-12

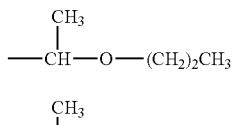 (AL11)-13

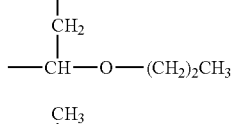 (AL11)-14

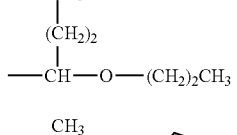 (AL11)-15

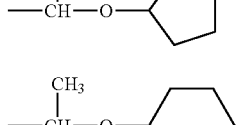 (AL11)-16

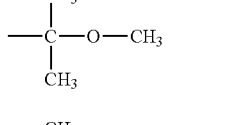 (AL11)-17

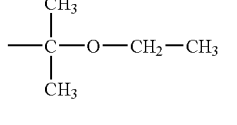 (AL11)-18

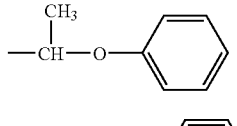 (AL11)-19

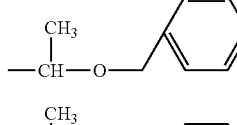 (AL11)-20

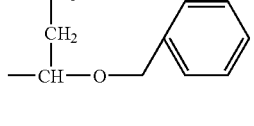 (AL11)-21

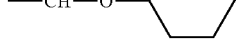

(AL11)-22

(AL11)-23

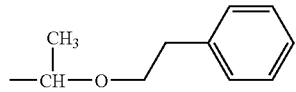

The 1% or more of hydrogen atoms of a hydroxyl group of the base resin may be subjected to intermolecular or intramolecular crosslinking by an acid-labile group of General Formula (AL 11a) or (AL 11b).

(AL11a)
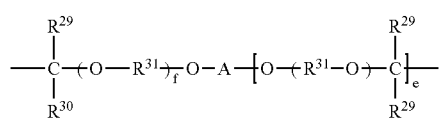

(AL11b)
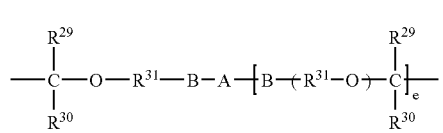

In this Formula, $R^{29}$ and $R^{30}$ are each independently a hydrogen atom or a straight-chained, branched-chained or cyclic alkyl group having 1 to 8 carbon atoms. $R^{29}$ and $R^3$ may be bonded together to form a ring. When the ring is formed, $R^{29}$ and $R^{30}$ each shows a straight-chained or branched alkylene group having 1 to 8 carbon atoms. $R^{31}$ is a straight-chained, branched or cyclic alkylene group having 1 to 10 carbon atoms. The f is an integer selected from 0 to 10. The A represents an aliphatic or alicyclic saturated hydrocarbon group having 1 to 50 (e+1)-valent carbon atoms, an aromatic hydrocarbon group, or a heterocycle group. These groups may have a hetero atom, or a part of the hydrogen atom or atoms bonded to the carbon atom may be substituted with a hydroxyl group, a carboxyl group, a carbonyl group, or a fluorine atom. The B is —CO—O—, —NHCO—O, or NHCONH—. The e is an integer selected from 1 to 7.

Specific examples of cross-link type acetal of General Formulas (AL 11-a) and (AL 11-b) include (AL 11)-24 to (AL 11)-31 below.

(AL11)-24
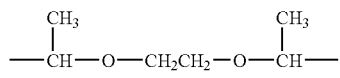

(AL11)-25
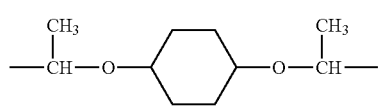

(AL11)-26
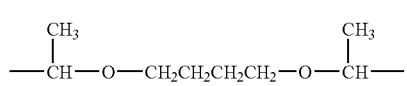

(AL11)-27

(AL11)-28
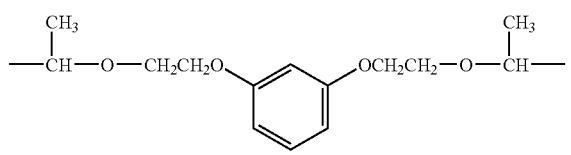

(AL11)-29
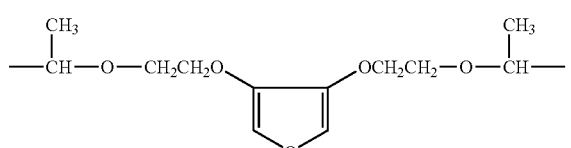

(AL11)-30
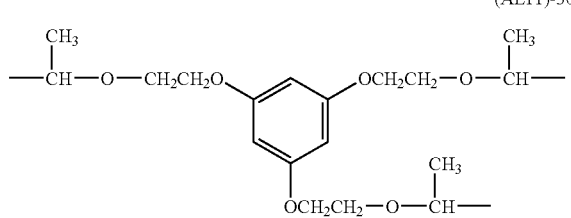

(AL11)-31
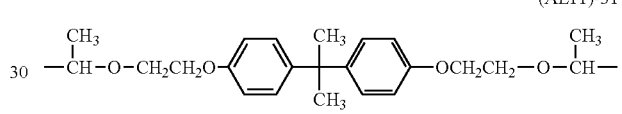

Examples of the tertiary alkyl group of Formula (AL 12) include a tert-butyl group, a triethylcarbyl group, a 1-ethylnorbonyl group, a 1-methylcyclohexyl group, a 1-ethylcyclopentyl group, a 2-(2-methyl)adamanthyl group, 2-(2-ethyl)adamanthyl group, a tert-amyl group and General Formulas (AL 12)1 to (AL 12)-18 shown below.

(AL12)-1
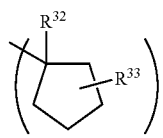

(AL12)-2
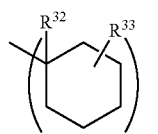

(AL12)-3
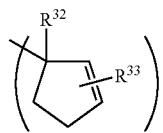

(AL12)-4
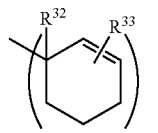

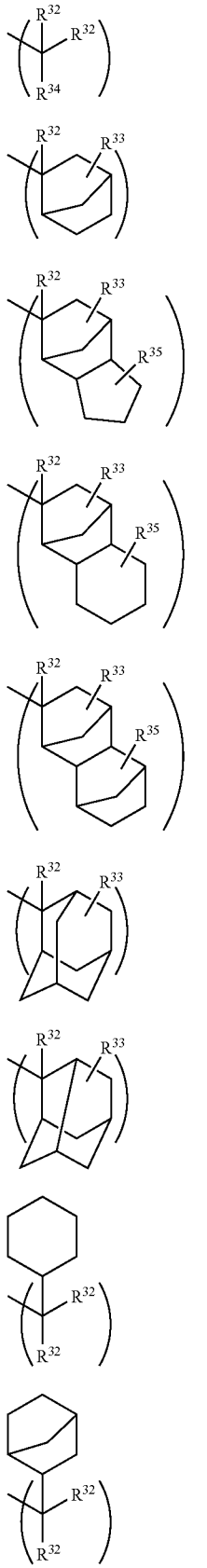

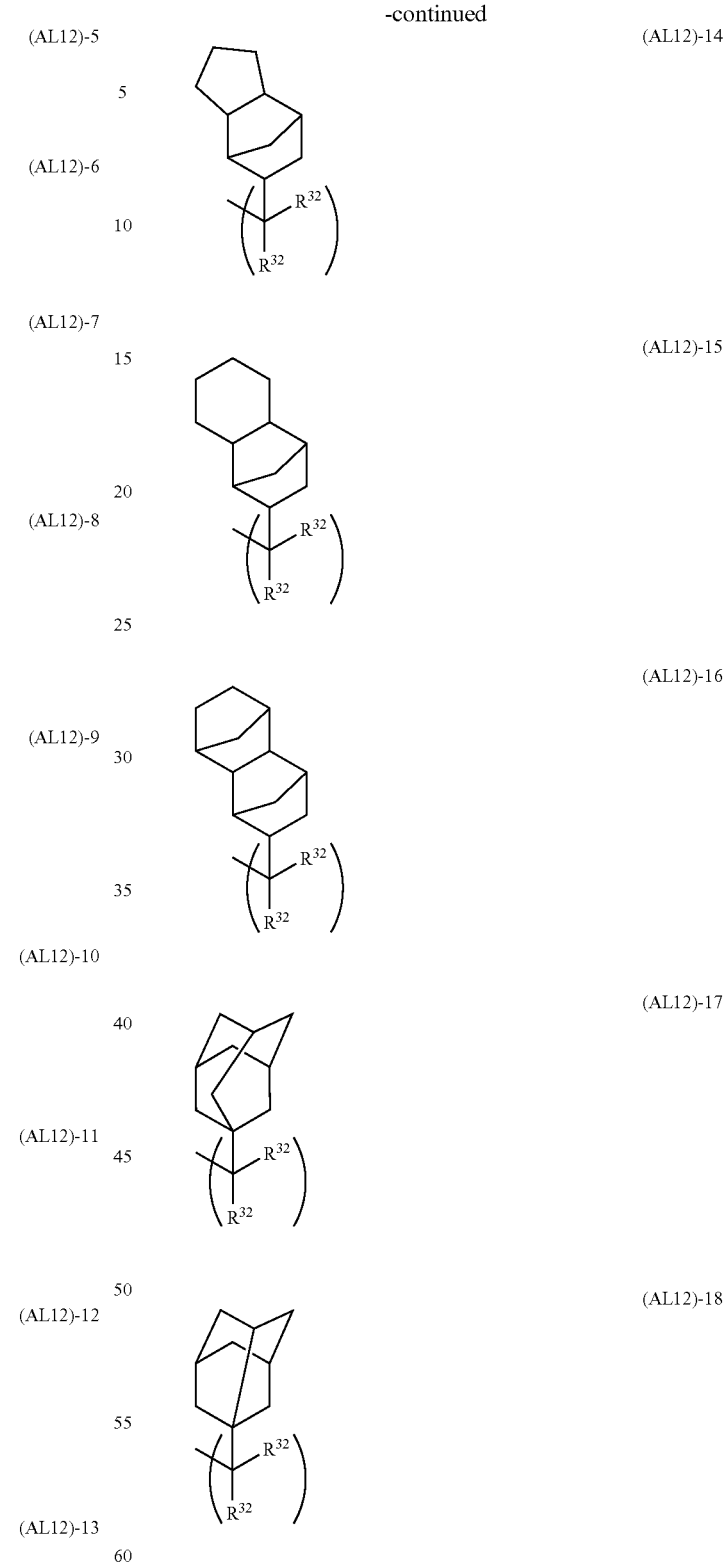

In the above Formula, $R^{32}$, which may be same or different, is independently a straight-chained, branched or cyclic alkyl group having 1 to 8 carbon atoms, or an aryl or aralkyl group having 6 to 20 carbon atoms. $R^{33}$ and $R^{35}$ each does not exist, or is independently a straight-chained, branched or cyclic alkyl group having 1 to 20 carbon atoms. $R^{34}$ is an aryl or aralkyl group having 6 to 20 carbon atoms.

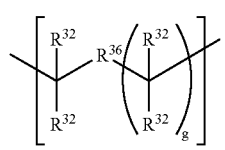
(AL12)-19

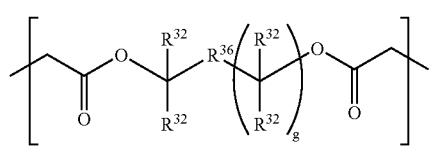
(AL12)-20

Further, as shown in (AL 12)-19 and (AL 12)-20, $R^{36}$, an alkylene or arylene group having valency of two or more, may be comprised, and the polymer may be subjected to intramolecular or intermolecular crosslinking. $R^{32}$ of Formula (12)-19 may be the same as above. $R^{36}$ is a straight-chained branched or cyclic alkylene or arylene group having 1 to 20 carbon atoms, and may comprise a hetero atom such as an oxygen atom, a sulfur atom and a nitrogen atom. The g is an integer selected from 1 to 3.

Further, $R^{32}$, $R^{33}$, $R^{34}$, and $R^{35}$ each may comprise a hetero atom such as oxygen, nitrogen and sulfur. Specific examples thereof can include the following Formulas (13)-1 to (13)-7.

 (13)-1

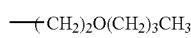 (13)-2

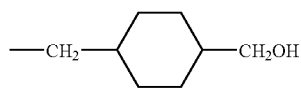 (13)-3

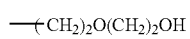 (13)-4

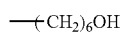 (13)-5

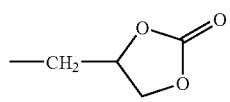 (13)-6

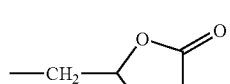 (13)-7

The preferable base resin used in the present invention is a polymeric structure that has a silicon atom. A polymer that has silicon serving as an acid-labile group can be first mentioned as the silicon-containing polymer. A silicon-containing acid-labile group includes a trialkylsilyl group with each alkyl group having 1 to 6 carbon atoms such as a trimethylsilyl group, a triethylsilyl group and a dimethyl-tert-butylsilyl group. Additionally, an acid-labile group containing silicon shown below can be used.

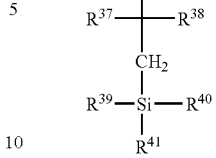
(A-4)

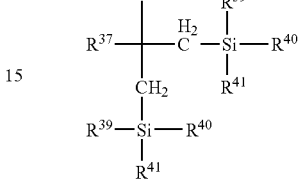
(A-5)

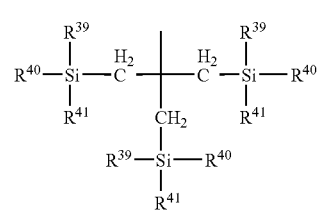
(A-6)

In the above Formula, $R^{37}$ and $R^{38}$ are each independently a hydrogen atom or an alkyl group having 1 to 20 carbon atoms. The $R^{39}$, $R^{40}$ and $R^{41}$, which may be same or different, are each independently an alkyl or haloalkyl group having 1 to 20 carbon atoms, an aryl group having 6 to 20 carbon atoms, a silicon-containing group that is bonded to the silicon atom by a siloxane bond or a silethylene bond, or a trimethylsilyl group. The $R^{37}$ and $R^{38}$ may be bonded together to form a ring. Specific examples of (A-4), (A-5), and (A-6) may include the following.

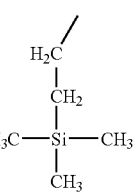
(A-4)-1

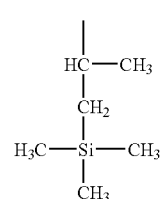
(A-4)-2

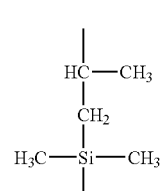
(A-4)-3

-continued
(A-4)-4
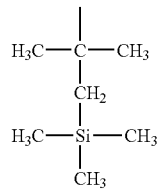
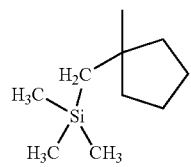
(A-4)-5
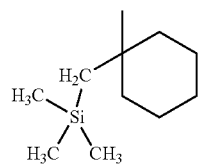
(A-4)-6
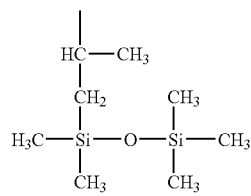
(A-4)-7
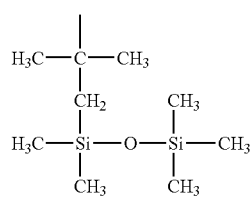
(A-4)-8
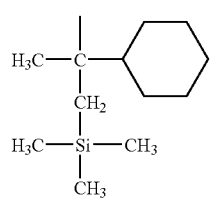
(A-4)-9
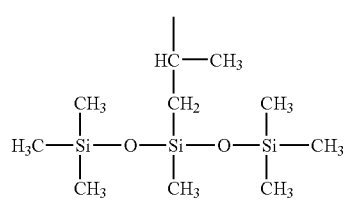
(A-4)-10
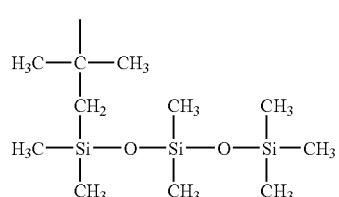
-continued
(A-4)-11
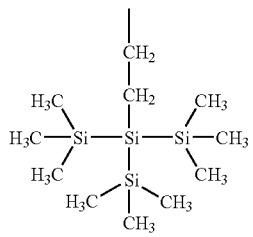
(A-4)-12
(A-4)-13
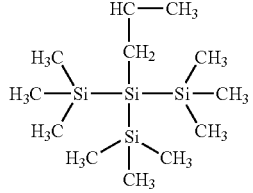
(A-5)-2
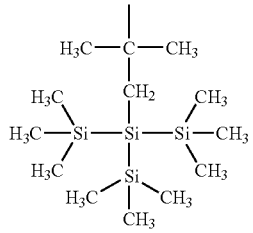
(A-5)-1
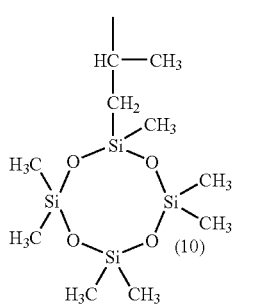
(A-5)-1
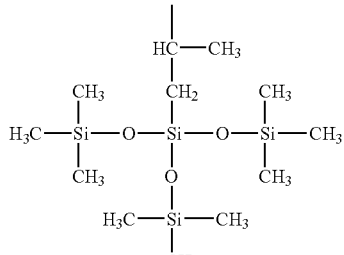
Additionally, a cyclic acid-labile group that contains silicon shown in General Formula (A-7) or (A-8) can be used.

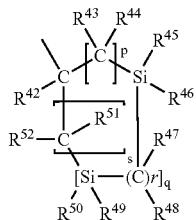

A-7

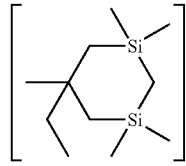

A-8

Herein, $R^{42}$ and $R^{54}$ are each independently a straight-chained, branched or cyclic alkyl group having 1 to 20 carbon atoms. The $R^{43}$, $R^{44}$, $R^{47}$, $R^{48}$, $R^{51}$, $R^{52}$ and $R^{53}$ are each independently a hydrogen atom, or a straight-chained, branched or cyclic alkyl group having 1 to 20 carbon atoms. The $R^{45}$, $R^{46}$, $R^{49}$ and $R^{50}$ are each independently a hydrogen atom, or a straight-chained, branched or cyclic alkyl group having 1 to 20 carbon atoms, or a fluorinated alkyl group having 1 to 20 carbon atoms, or an aryl group having 6 to 20 carbon atoms. The p, q, r, and s are each an integer selected from 0 to 10, and $1 \leq p+q+s \leq 20$. Specific examples of (A-7) and (A-8) include the following.

(A-7)-1

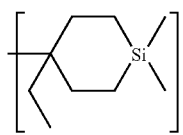

(A-7)-2

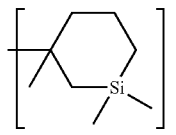

(A-7)-3

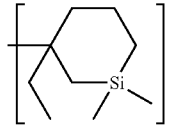

(A-7)-4

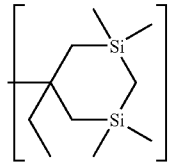

(A-7)-5

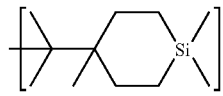

(A-7)-6

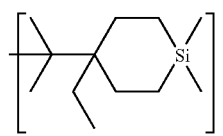

(A-8)-1

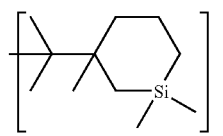

(A-8)-2

(A-8)-3

(A-8)-4

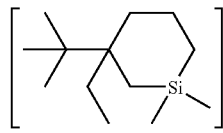

(A-8)-5

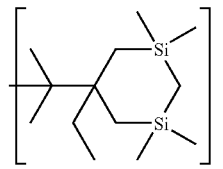

(A-8)-6

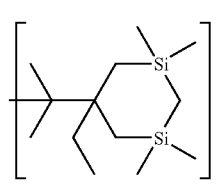

An acid-labile group of a trialkylsilyl group having 1 to 6 carbon atoms includes a trimethylsilyl group, a triethylsilyl group and a dimethyl-tert-butylsilyl group.

Secondly, the silicon-containing polymer used in the present invention may be a repeating unit that contains silicon stable with acid.

The acid-stable silicon-containing repeating unit may include the following.

(9)-1
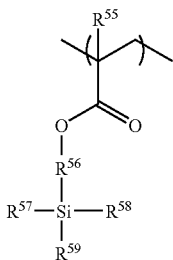

(9)-2
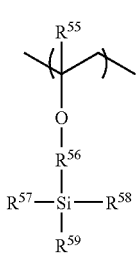

(9)-3
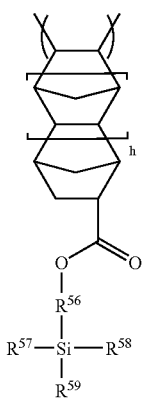

(9)-4
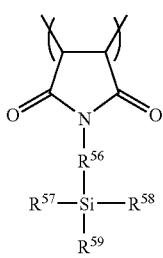

(9)-5
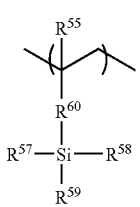

Herein, $R^{55}$ is a hydrogen atom, a methyl group, a fluorine atom for a trifluoromethyl group. The $R^{56}$ is a bivalent hydrocarbon group having 3 to 10 carbon atoms. The $R^{57}$, $R^{58}$ and $R^{59}$, which may be same or different, are each independently a hydrogen atom, an alkyl group having 1 to 10 carbon atoms, an aryl group, an alkyl group that contains a fluorine atom, a hydrocarbon group that contains a silicon atom, or a group that contains a siloxane bond. A pair of $R^{57}$ and $R^{58}$, a pair of $R^{58}$ and $R^{59}$ and a pair of $R^{57}$ and $R^{59}$ may be each bonded together to form a ring. $R^{25}$ is a single bond or an alkylene group having 1 to 4 carbon atoms. The h is 0 or 1.

Specific examples of (9)-5 include the following.

(10)-1
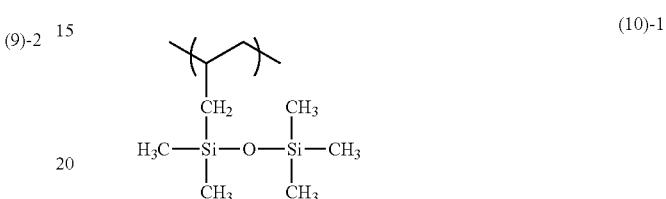

(10)-2
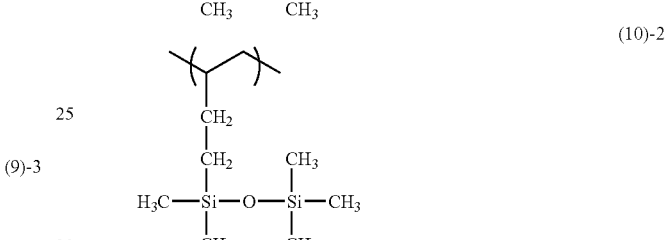

(10)-3
(10)-4
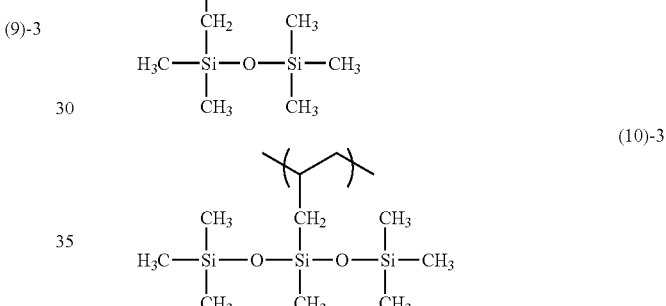

(10)-5
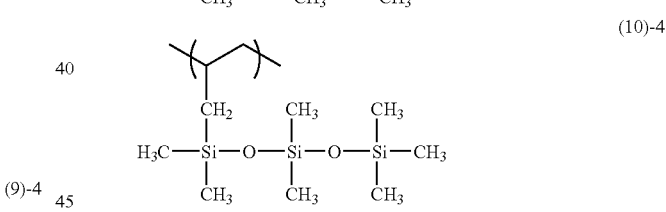

(10)-6
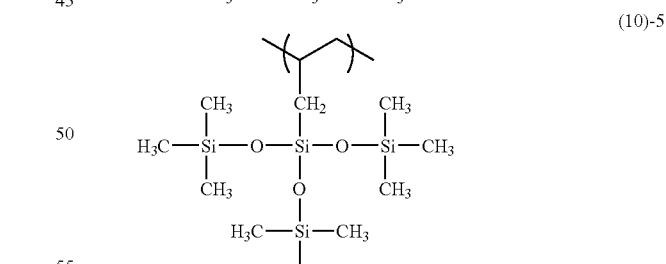

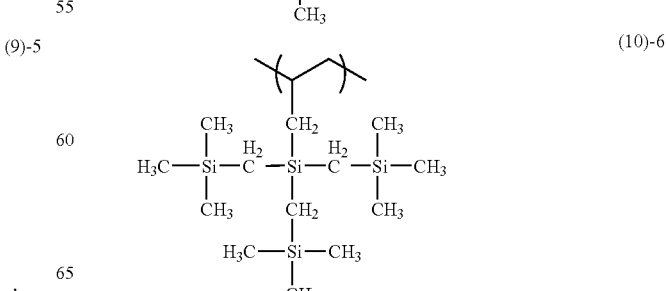

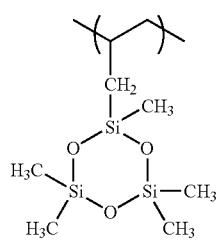
(10)-7
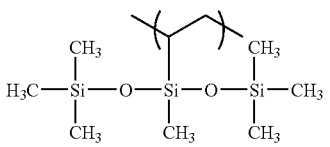
(10)-13
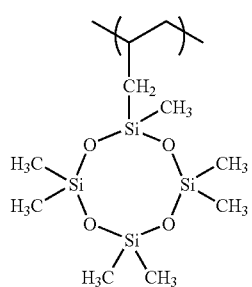
(10)-8
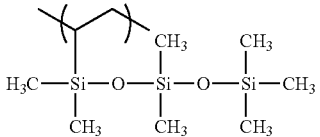
(10)-14
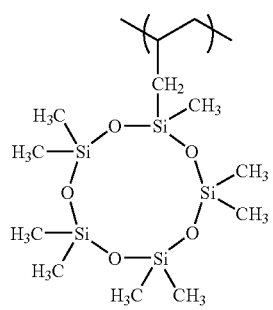
(10)-9
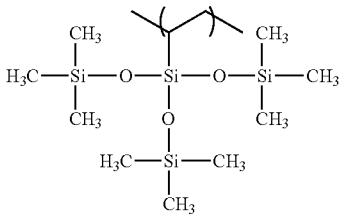
(10)-15
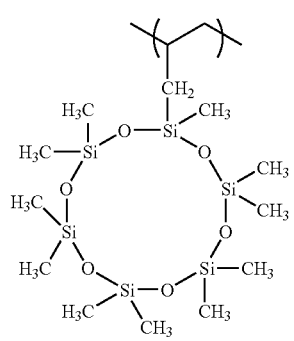
(10)-10
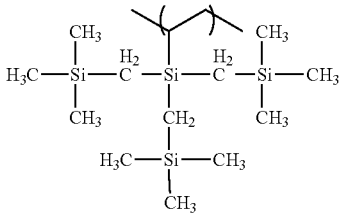
(10)-16
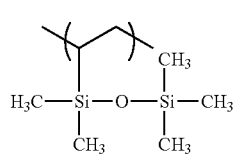
(10)-11
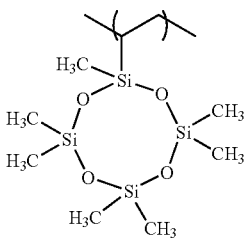
(10)-17
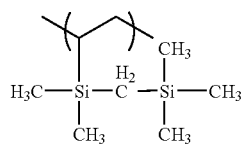
(10)-12
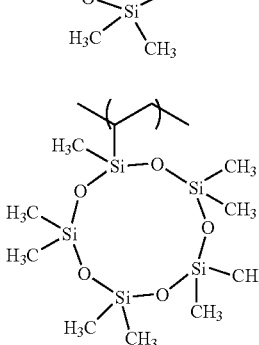
(10)-18
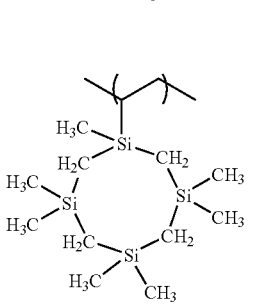
(10)-19

-continued

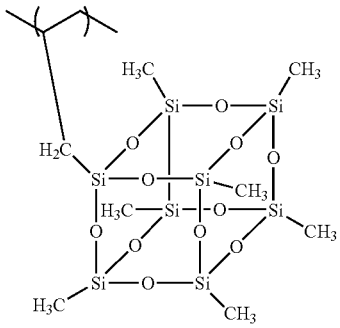
(10)-20

The base resin used in the present invention may be a single kind of polymer or a mixture of two or more kinds of polymers. The performance of a resist material can be adjusted by using a plurality of polymers. A plurality of kinds of polymers that differ in molecular weight and in the degree of dispersive may be used. The molecular weight of polymers used for the base resin can be calculated in terms of polystyrene by use of gas permeation chromatography (GPC). Preferable weight-average molecular weight may be 5,000 to 100,000. If it is below 5,000, inferior film-formation properties or inferior resolution may be aruse, and, if it exceeds 100,000, inferior resolution may be aruse. When a silicon-containing polymer is used as the base resin, the same may apply to the range of preferable weight-average molecular weights thereof.

The resist material of the present invention may comprise an acid generator conventionally proposed, which differs from the sulfonium salt and the iodonium salt of General Formula (1) shown above.

An acid generator which may be added include the following.
i. Onium salts of Formula (P1a-1), (P1a-2), or (P1b) shown below,
ii. Diazomethane derivatives of Formula (P2),
iii. Glyoxime derivatives of Formula (P3),
iv. Bissulfone derivatives of Formula (P4),
v. Sulfonate esters of N-hydroxyimide compounds of Formula (P5),
vi. β-ketosulfonate derivatives,
vii. Disulfone derivatives,
viii. Nitrobenzylsulfonate derivatives, and
ix. Sulfonate derivatives.

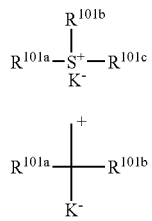
P1a-1

P1a-2

Herein, $R^{101a}$, $R^{101b}$ and $R^{101c}$ each independently represents a straight-chained, branched or cyclic alkyl, alkenyl, oxoalkyl or oxoalkenyl group of 1 to 12 carbon atoms, an aryl group of 6 to 20 carbon atoms, or an aralkyl or aryloxoalkyl group of 7 to 12 carbon atoms, wherein the hydrogen atoms may be partially or entirely substituted with alkoxy or other groups. Also, $R^{101b}$ and $R^{101c}$, taken together, may form a ring. $R^{101b}$ and $R^{101c}$ each are alkylene groups of 1 to 6 carbon atoms when they form a ring. The $K^-$ is a non-nucleophilic counter ion other than (1), (2), and (3).

The $R^{101a}$, $R^{101b}$ and $R^{110c}$ may be the same or different from each other. Exemplary alkyl groups include methyl, ethyl, propyl, isopropyl, n-butyl, sec-butyl, tert-butyl, pentyl, hexyl, heptyl, octyl, cyclopentyl, cyclohexyl, cycloheptyl, cyclopropylmethyl, 4-methylcyclohexyl, cyclohexylmethyl, norbornyl, and adamantyl groups, etc. Exemplary alkenyl groups include vinyl, allyl, propenyl, butenyl, hexenyl, and cyclohexenyl groups, etc. Exemplary oxoalkyl groups include 2-oxocyclopentyl and 2-oxocyclohexyl as well as 2-oxopropyl, 2-cyclopentyl-2-oxoethyl, 2-cyclohexyl-2-oxoethyl, and 2-(4-methylcyclohexyl)-2-oxoethyl groups, etc. Exemplary aryl groups include phenyl and naphthyl; alkoxyphenyl groups such as p-methoxyphenyl, m-methoxyphenyl, o-methoxyphenyl, ethoxyphenyl, p-tert-butoxyphenyl, and m-tert-butoxyphenyl groups; alkylphenyl groups such as 2-methylphenyl, 3-methylphenyl, 4-methylphenyl, ethylphenyl, 4-tert-butylphenyl, 4-butylphenyl, and dimethylphenyl groups; alkylnaphthyl groups such as methylnaphthyl and ethylnaphthyl groups; alkoxynaphthyl groups such as methoxynaphthyl and ethoxynaphthyl groups; dialkylnaphthyl groups such as dimethylnaphthyl and diethylnaphthyl groups; and dialkoxynaphthyl groups such as dimethoxynaphthyl and diethoxynaphthyl groups. Exemplary aralkyl groups include benzyl, phenylethyl, and phenethyl groups. Exemplary aryloxoalkyl groups are 2-aryl-2-oxoethyl groups such as 2-phenyl-2-oxoethyl, 2-(1-naphthyl)-2-oxoethyl, and 2-(2-naphthyl)-2-oxoethyl gorups. Examples of the, non-nucleophilic counter ion represented by $K^-$ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4, and 5-pentafluorobenzene-sulfonate; and alkylsulfonate such as mesylate and butanesulfonate.

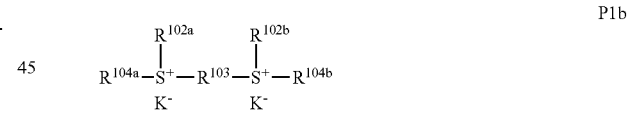
P1b

Herein, $R^{102a}$ and $R^{102b}$ each independently represents a straight-chained, branched or cyclic alkyl group of 1 to 8 carbon atoms. The $R^{103}$ represents a straight-chained, branched or cyclic alkylene group of 1 to 10 carbon atoms. The $R^{104a}$ and $R^{104b}$ each independently represents a 2-oxoalkyl group of 3 to 7 carbon atoms. The $K^-$ is a non-nucleophilic counter ion.

Specific examples of the groups represented by $R^{102a}$ and $R^{102b}$ include methyl, ethyl, propyl, isopropyl, n-butyl, sec-butyl, tert-butyl, pentyl, hexyl, heptyl, octyl, cyclopentyl, cyclohexyl, cyclopropylmethyl, 4-methylcyclohexyl and cyclohexylmethyl groups. Specific examples of the groups represented by $R^{103}$ include methylene, ethylene, propylene, butylene, pentylene, hexylene, heptylene, octylene, nonylene, 1,4-cyclohexylene, 1,2-cyclohexylene, 1,3-cyclopentylene, 1,4-cyclooctylene and 1,4-cyclohexanedimethylene groups. Specific examples of the groups represented by $R^{104a}$ and $R^{104b}$ include 2-oxopropyl, 2-oxocyclopentyl, 2-oxocyclohexyl and 2-oxocycloheptyl groups. Specific examples of the counter ion represented by K⁻ may be the same as exemplified by Formulas (P1a-1) and (P1a-2).

P2

Herein, $R^{105}$ and $R^{106}$ each independently represents a straight-chained, branched or cyclic alkyl or halogenated alkyl group of 1 to 12 carbon atoms, an aryl or halogenated aryl group of 6 to 20 carbon atoms, or an aralkyl groups of 7 to 12 carbon atoms.

Of the groups represented by $R^{105}$ and $R^{106}$ exemplary alkyl groups include methyl, ethyl, propyl, isopropyl, n-butyl, sec-butyl, tert-butyl, pentyl, hexyl, heptyl, octyl, amyl, cyclopentyl, cyclohexyl, cycloheptyl, norbornyl, and adamantyl groups, etc. Exemplary halogenated alkyl groups include trifluoromethyl, 1,1,1-trifluoroethyl, 1,1,1-trichloroethyl, and nonafluorobutyl groups, etc. Exemplary aryl groups include phenyl group; alkoxyphenyl groups such as p-methoxyphenyl, m-methoxyphenyl, o-methoxyphenyl, ethoxyphenyl, p-tert-butoxyphenyl, and m-tert-butoxyphenyl groups, etc.; and alkylphenyl groups such as 2-methylphenyl, 3-methylphenyl, 4-methylphenyl, ethylphenyl, 4-tert-butylphenyl, 4-butylphenyl, and dimethylphenyl groups, etc. Exemplary halogenated aryl groups include fluorophenyl, chlorophenyl, and 1,2,3,4,5-pentafluorophenyl groups, etc. Exemplary aralkyl groups include benzyl and phenethyl groups, etc.

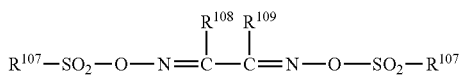

P3

Herein, $R^{107}$, $R^{108}$, and $R^{109}$ each independently represents a straight-chained, branched or cyclic alkyl or halogenated alkyl group of 1 to 12 carbon atoms, an aryl or halogenated aryl group of 6 to 20 carbon atoms, or an aralkyl group of 7 to 12 carbon atoms. $R^{108}$ and $R^{109}$ may be bonded to each other to form a ring. $R^{108}$ and $R^{109}$ each may be a straight-chained or branched alkylene group of 1 to 6 carbon atoms when it forms a ring Specific examples of the alkyl, halogenated alkyl, aryl, halogenated aryl, or aralkyl group represented by $R^{107}$, $R^{108}$ and $R^{109}$ are the same as exemplified for $R^{105}$ and $R^{106}$. Examples of the alkylene groups represented by $R^{108}$ and $R^{109}$ are methylene, ethylene, propylene, butylene, and hexylene groups, etc.

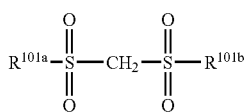

P4

Herein, $R^{101a}$ and $R^{101b}$ are as defined above.

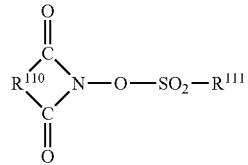

P5

Herein, $R^{110}$ is an arylene group of 6 to 10 carbon atoms, alkylene group of 1 to 6 carbon atoms or alkenylene group of 2 to 6 carbon atoms wherein the hydrogen atoms may be partially or entirely further substituted with a straight-chained or branched alkyl group of 1 to 4 carbon atoms, a straight-chained or branched alkoxy group of 1 to 4 carbon atoms, a nitro group, an acetyl group or a phenyl group. $R^{11}$ is a straight-chained, branched, cyclic or substituted alkyl group of 1 to 8 carbon atoms, a straight-chained, branched, cyclic or substituted alkenyl group of 1 to 8 carbon atoms, a straight-chained, branched, cyclic or substituted alkoxyalkyl group of 1 to 8 carbon atoms, a phenyl group or a naphthyl group, wherein the hydrogen atoms may be partially or entirely further substituted with an alkyl or alkoxy group of 1 to 4 carbon atoms; a phenyl group which may have been substituted with an alkyl group of 1 to 4 carbon atoms, an alkoxy group of 1 to 4 carbon atoms, a nitro group or an acetyl group; a hetero-aromatic group of 3 to 5 carbon atoms; or a chlorine atom or a fluorine atom.

Of the groups represented by $R^{110}$, exemplary arylene groups include 1,2-phenylene and 1,8-naphthylene groups, etc.; exemplary alkylene groups include methylene, 1,2-ethylene, 1,3-propylene, 1,4-butylene, 1-phenyl-1,2-ethylene, and norbornane-2,3-diyl groups, etc.; and exemplary alkenylene groups include 1,2-vinylene, 1-phenyl-1,2-vinylene, and 5-norbornene-2,3-diyl groups, etc. Of the groups represented by $R^{111}$, exemplary alkyl groups are as exemplified for $R^{101a}$, $R^{101b}$ and $R^{101c}$; exemplary alkenyl groups include vinyl, 1-propenyl, allyl, 1-butenyl, 3-butenyl, isoprenyl, 1-pentenyl, 3-pentenyl, 4-pentenyl, dimethylallyl, 1-hexenyl, 3-hexenyl, 5-hexenyl, 1-heptenyl, 3-heptenyl, 6-heptenyl, and 7-octenyl groups, etc.; and exemplary alkoxyalkyl groups include methoxymethyl, ethoxymethyl, propoxymethyl, butoxymethyl, pentyloxymethyl, hexyloxymethyl, heptyloxymethyl, methoxyethyl, ethoxyethyl, propoxyethyl, butoxyethyl, pentyloxyethyl, hexyloxyethyl, methoxypropyl, ethoxypropyl, propoxypropyl, butoxypropyl, methoxybutyl, ethoxybutyl, propoxybutyl, methoxypentyl, ethoxypentyl, methoxyhexyl, and methoxyheptyl groups, etc.

Of the substituents for these groups, the alkyl groups of 1 to 4 carbon atoms include methyl, ethyl, propyl, isopropyl, n-butyl, isobutyl and tert-butyl groups, etc.; the alkoxy groups of 1 to 4 carbon atoms include methoxy, ethoxy, propoxy, isopropoxy, n-butoxy, isobutoxy, and tert-butoxy groups, etc.; the phenyl groups which may have been substituted with an alkyl or alkoxy group of 1 to 4 carbon atoms, a nitro group or an acetyl group include phenyl, tolyl, p-tert-butoxyphenyl, p-acetylphenyl and p-nitrophenyl groups, etc.; and the hetero-aromatic groups of 3 to 5 carbon atoms include pyridyl and furyl groups, etc.

Specifically, examples of onium salts are diphenyliodonium trifluoromethanesulfonate, (p-tert-butoxyphenyl)phenyliodonium trifluoromethanesulfonate, diphenyliodonium p-toluenesulfonate, (p-tert-butoxyphenyl)phenyliodonium p-toluenesulfonate, triphenylsulfonium trifluoromethanesulfonate, (p-tert-butoxyphenyl)diphenylsulfonium trifluoromethanesulfonate, bis(p-tert-butoxyphenyl)phenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, bis(p-tert-butoxyphenyl)phenylsulfonium p-toluenesulfonate, tris(p-tert-butoxyphenyl)sulfonium p-toluenesulfonate, triphenylsulfonium nonafluorobutanesulfonate, triphenylsulfonium butanesulfonate, trimethylsulfonium trifluoromethanesulfonate, trimethylsulfonium p-toluenesulfonate, cyclohexylmethyl(2-oxocyclohexyl)sulfonium trifluoromethanesulfonate, cyclohexylmethyl(2-oxocyclohexyl)sulfonium p-toluenesulfonate, dimethylphenylsulfonium trifluoromethanesulfonate, dimethylphenylsulfonium p-toluenesulfonate, dicyclohexylphenylsulfonium trifluoromethanesulfonate, dicyclohexylphenylsulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocyclohexyl)sulfonium trifluoromethanesulfonate, ethylenebis-[methyl(2-oxocyclopentyl)sulfonium trifluoromethanesulfonate], and 1,2'-naphthylcarbonylmethyltetrahydrothiophenium triflate.

Examples of diazomethane derivatives are bis(benzenesulfonyl)diazomethane, bis(p-toluenesulfonyl)diazomethane, bis(xylenesulfonyl)diazomethane, bis(cyclohexylsulfonyl)diazomethane, bis(cyclopentylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, bis(tert-butylsulfonyl)diazomethane, bis(n-amylsulfonyl)diazomethane, bis(isoamylsulfonyl)diazomethane, bis(sec-amylsulfonyl)diazomethane, bis(tert-amylsulfonyl)diazomethane, 1-cyclohexylsulfonyl-1-(tert-butylsulfonyl)diazomethane, 1-cylohexylsulfonyl-1-(tert-amylsulfonyl)diazomethane, and 1-tert-amylsulfonyl-1-(tert-butylsulfonyl)diazomethane.

Examples of glyoxime derivatives are bis-o-(p-toluenesulfonyl)-α-dimethylglyoxime, bis-o-(p-toluenesulfonyl)-α-diphenylglyoxime, bis-o-(p-toluenesulfonyl)-α-dicyclohexyloxyoxime, bis-o-(p-toluenesulfonyl)-2,3-pentanedioneglyoxime, bis-o-(p-toluenesulfonyl)-2-methyl-3,4-pentanedioneglyoxime, bis-o-(n-butanesulfonyl)-α-dimethylglyoxime, bis-o-(n-butanesulfonyl)-α-diphenylglyoxime, bis-o-(n-butanesulfonyl)-α-dicyclohexylglyoxime, bis-o-(n-butanesulfonyl)-2,3-pentanedioneglyoxime, bis-o-(n-butanesulfonyl)-2-methyl-3,4-pentanedioneglyoxime, bis-o-(methanesulfonyl)-α-dimethylglyoxime, bis-o-(trifluoromethanesulfonyl)-α-dimethylglyoxime, bis-o-(1,1,1-trifluoroethanesulfonyl)-α-dimethylglyoxime, bis-o-(tert-butanesulfonyl)-α-dimethylglyoxime, bis-o-(perfluorooctanesulfonyl)-α-dimethylglyoxime, bis-o-(cyclohexanesulfonyl)-α-dimethylglyoxime, bis-o-(benzenesulfonyl)-α-dimethylglyoxime, bis-o-(p-fluorobenzenesulfonyl)-α-dimethylglyoxime, bis-o-(p-tert-butylbenzenesulfonyl)-α-dimethylglyoxime, bis-o-(xylenesulfonyl)-α-dimethyglyoxime, and bis-o-(camphorsulfonyl)-α-dimethylglyoxime.

Examples of bissulfone derivatives are bisnaphthylsulfonylmethane, bistrifluoromethylsulfonylmethane, bismethylsulfonylmethane, bisethylsulfonylmethane, bispropylsulfonylmethane, bisisopropylsulfonylmethane, bis-p-toluenesulfonylmethane, and bisbenzenesulfonylmethane.

Examples of β-ketosulfone derivatives are 2-cyclohexylcarbonyl-2-(p-toluenesulfonyl)propane and 2-isopropylcarbonyl-2-(p-toluenesulfonyl)propane.

Examples of disulfone derivatives are diphenyl disulfone and dicyclohexyl disulfone.

Examples of nitrobenzyl sulfonate derivatives are 2,6-dinitrobenzyl p-toluenesulfonate and 2,4-dinitrobenzyl p-toluenesulfonate.

Examples of sulfonate derivatives are 1,2,3-tris(methanesulfonyloxy)benzene, 1,2,3-tris(trifluoromethanesulfonyloxy)benzene, and 1,2,3-tris(p-toluenesulfonyloxy)benzene.

Examples of sulfonate derivatives of N-hydroxyimide compounds are N-hydroxysuccinimide methanesulfonate, N-hydroxysuccinimide trifluoromethanesulfonate, N-hydroxysuccinimide ethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide 1-octanesulfonate, N-hydroxysuccinimide p-toluenesulfonate, N-hydroxysuccinimide p-methoxybenzenesulfonate, N-hydroxysuccinimide 2-chloroethanesulfonate, N-hydroxysuccinimide benzenesulfonate, N-hydroxysuccinimide 2,4,6-trimethylbenzenesulfonate, N-hydroxysuccinimide 1-naphthalenesulfonate, N-hydroxysuccinimide 2-naphthalenesulfonate, N-hydroxy-2-phenylsuccinimide methanesulfonate, N-hydroxymaleimide methanesulfonate, N-hydroxymaleimide ethanesulfonate, N-hydroxy-2-phenylmaleimide methanesulfonate, N-hydroxyglutarimide methanesulfonate, N-hydroxyglutarimide benzenesulfonate, N-hydroxyphthalimide methanesulfonate, N-hydroxyphthalimide benzenesulfonate, N--hydroxyphthalimide trifluoromethanesulfonate, N-hydroxyphthalimide p-toluenesulfonate, N-hydroxynaphthalimide methanesulfonate, N-hydroxynaphthalimide benzenesulforiate, N-hydroxy-6-norbornene-2,3-dicarboxyimide methanesulfonate, N-hydroxy-5-norbornene-2,3-dicarboxyimide trifluoromethanesulfonate, and N-hydroxy-5-norbornene-2,3-dicarboxyimide p-toluenesulfonate.

Preferably, use is made of onium salts such as triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate, (p-tert-butoxyphenyl)diphenylsulfonium p-toluenesulfonate, tris(p-tert-butoxyphenyl)sulfonium p-toluenesulfonate, trinaphthylsulfonium trifluoromethanesulfonate, cyclohexylmethyl(2-oxocyclohexyl)sulfonium trifluoromethanesulfonate, (2-norbornyl)methyl(2-oxocylohexyl)sulfonium trifluoromethanesulfonate, and 1,2'-naphthylcarbonylmethyltetrahydrothiophenium triflate; diazomethane derivatives such as bis(benzenesulfonyl)diazomethane, bis(p-toluenesulfonyl)diazomethane, bis(cyclohexylsulfonyl)diazomethane, bis(n-butylsulfonyl)diazomethane, bis(isobutylsulfonyl)diazomethane, bis(sec-butylsulfonyl)diazomethane, bis(n-propylsulfonyl)diazomethane, bis(isopropylsulfonyl)diazomethane, and bis(tert-butylsulfonyl)diazomethane; glyoxime derivatives such as bis-o-(p-toluenesulfonyl)-α-dimethylglyoxime and bis-o-(n-butanesulfonyl)-α-dimethylglyoxime; bissulfone derivatives such as bisnaphthylsulfonylmethane; and sulfonate derivatives of N-hydroxyimide compounds such as N-hydroxysuccinimide methanesulfonate, N-hydroxysuccinimide trifluoromethanesulfonate, N-hydroxysuccinimide 1-propanesulfonate, N-hydroxysuccinimide 2-propanesulfonate, N-hydroxysuccinimide 1-pentanesulfonate, N-hydroxysuccinimide p-toluenesulfonate, N-hydroxynaphthalimide methanesulfonate, and N-hydroxynaphthalimide benzenesulfonate.

The photoacid generator may be used singly or in a combination of two or more thereof. Onium salts are effective for improving rectangularity, while diazomethane derivatives and glyoxime derivatives are effective for reducing standing waves. The combination of an onium salt with a diazomethane or a glyoxile derivative allows for fine adjustment of the profile.

The total amount of the photoacid generator comprising the sulfonium salt of Formula (1) is preferably 0.1 to 15 parts by weight, and especially 0.5 to 8 parts by weight, per 100 parts by weight of the base resin. Less than 0.1 part by weight of the photoacid generator may provide poor sensitivity whereas more than 15 parts by weight of the photoacid generator may lower the transparency and resolution of resist materials.

The organic solvent used in the present invention may be any organic solvent in which the base resin, photoacid generator, and other additives are soluble. Examples of the organic solvent include ketones such as cyclohexanone and methyl-2-n-amylketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate. A solvent may be used singly or in a combination of two or more thereof, but the present invention is not limited to these solvents.

In the present invention, of the above organic solvents, it is preferable to use diethylene glycol dimethyl ether and 1-ethoxy-2-propanol because the photoacid generator serving as one of the resist components is most soluble therein. It is also preferable to use propylene glycol monomethyl ether acetate, which is a safe solvent, or a mixture thereof.

An appropriate amount of the organic solvent used may be 200 to 11,000 parts by weight, especially 400 to 800 parts by weight per 100 parts by weight of the base resin.

A dissolution inhibitor may be added to the resist material of the present invention. Typical dissolution inhibitor is a compound having a weight-average molecular weight within a range of 100 to 1,000, preferably 150 to 800, and containing on the molecule at least two phenolic hydroxyl groups in which 0 to 100 mol %, on average, of the hydrogen atoms of the phenolic hydroxyl groups are substituted with acid-labile groups, and compounds having a similar average molecular weight and containing on the molecule a carboxyl group in which 80 to 100 mol %, on average, of the hydrogen atoms of the carboxyl group are substituted with acid-labile groups.

It is noted that the percent substitution of the hydrogen atom of the phenolic hydroxyl group or carboxyl group with an acid-labile group may be, on average, at least 0 mol %, preferably at least 30 mol %, based on the entire phenolic hydroxyl group or carboxyl group, with the upper limit of percent substitution being 100 mol %, preferably 80 mol %.

Preferable examples of such compounds having two or more phenolic hydroxyl groups or compounds having a carboxyl group include those of Formulas (D1) to (D14) below.

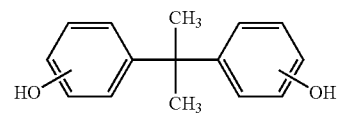
D1

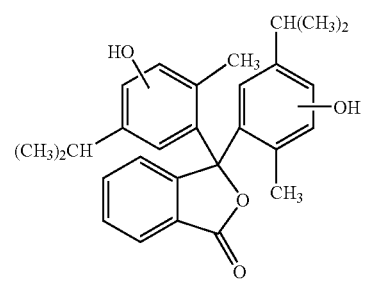
D2

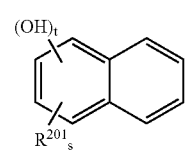
D3

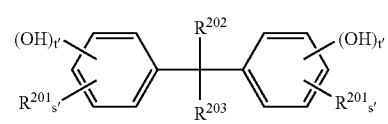
D4

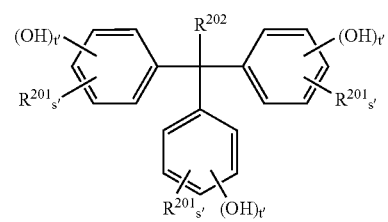
D5

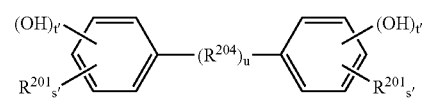
D6

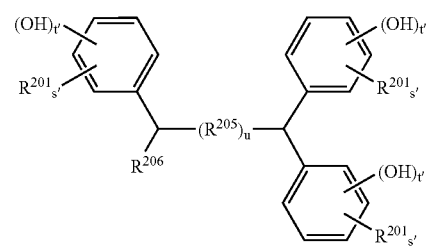
D7

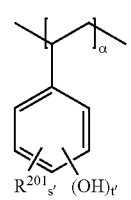
D8

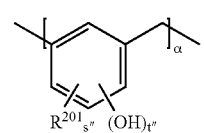
D9

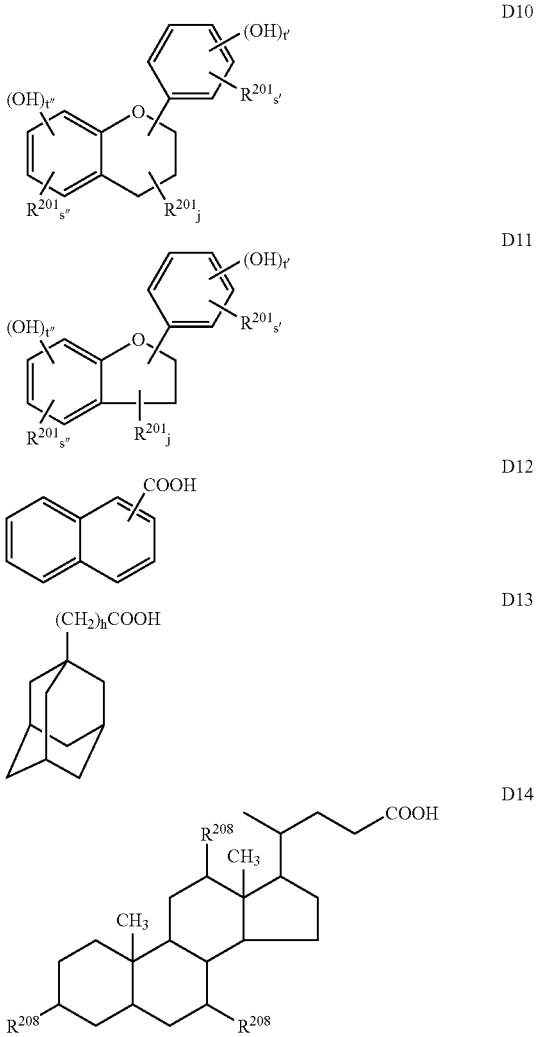

In these Formulas, $R^{201}$ and $R^{202}$ are each independently a hydrogen atom or a straight-chained or branched alkyl or alkenyl group of 1 to 8 carbon atoms. $R^{203}$ is a hydrogen atom, a straight-chained or branched alkyl or alkenyl group of 1 to 8 carbon atoms, or —$(R^{207})_k$COOH (where k=0 or 1). $R^{204}$ is —$(CH_2)_i$— (where i is an integer of 2 to 10), an arylene group of 6 to 10 carbon atoms, a carbonyl group, a sulfonyl group, an oxygen atom, or a sulfur atom. $R^{205}$ is an alkylene group of 1 to 10 carbon atoms, an arylene group of 6 to 10 carbon atoms, a carbonyl group, a sulfonyl group, an oxygen atom or a sulfur atom. $R^{206}$ is hydrogen, a straight-chained or branched alkyl or alkenyl group of 1 to 8 carbon atoms, or a hydroxyl-substitutional phenyl or naphthyl group. $R^{207}$ is a straight-chained or branched alkylene group of 1 to 10 carbon atoms. $R^{208}$ is hydrogen or hydroxyl. The letter j is an integer selected from 0 to 5. The u is 0 or 1. The s, t, s', t', s" and t" are numbers which satisfy s+t=8, s'+t'=5, and s"+t"=4, and are such that each phenyl skeleton has at least one hydroxyl group. The c is a number such that the compounds of Formula (D8) or (D9) may have a molecular weight of 100 to 1,000.)

In the above Formulas, examples of $R^{201}$ and $R^{202}$ include hydrogen, methyl, ethyl, butyl, propyl, ethynyl and cyclohexyl groups. Examples of $R^{203}$ include the same groups as for $R^{201}$ and $R^{202}$, as well as —COOH and —$CH_2$COOH. Examples of $R^{204}$ include ethylene, phenylene, carbonyl, sulfonyl groups, oxygen atom and sulfur atom. Examples of $R^{205}$ include a methylene group as well as the same groups as for $R^{204}$. Examples of $R^{206}$ include a hydrogen atom, methyl, ethyl, butyl, propyl, ethynyl, cyclohexyl groups, and a hydroxyl-substituted phenyl or naphthyl group.

Exemplary acid-labile groups on the dissolution inhibitor include the same acid-labile group that as on the base polymer, which may be the same as or different from that on the base polymer. Two or more different dissolution inhibitors can also be used.

The dissolution inhibitor may be formulated in an amount of 0 to 50 parts by weight, preferably 5 to 50 parts by weight, and more preferably 10 to 30 parts by weight, per 100 parts by weight of the base resin, and may be used singly or as a mixture of two or more thereof. Less than 5 parts by weight of the dissolution inhibitor may fail to yield an improved resolution, whereas use of more than 50 parts by weight may lead to the thinning of the patterned film, and thus a decline in resolution.

The dissolution inhibitor mentioned above may be synthesized by introducing an acid-labile group into a compound having a phenolic hydroxyl or carboxyl group in accordance with an organic chemical method.

The resist material of the invention may comprise a basic compound.

A suitable basic compound used herein is a compound capable of suppressing the rate of diffusion when the acid generated by the photoacid generator diffuses within the resist film. The inclusion of this type of basic compound may hold down the rate of acid diffusion within the resist film, resulting in better resolution. In addition, it may suppress changes in sensitivity after exposure, thus reducing substrate and environment dependence, as well as improving the exposure latitude and the pattern profile and the like.

Examples of the basic compound include primary, secondary, and tertiary aliphatic amines, mixed amines, aromatic amines, heterocyclic amines, carboxyl group-containing nitrogenous compounds, sulfonyl group-containing nitrogenous compounds, hydroxyl group-containing nitrogenous compounds, hydroxyphenyl group-containing nitrogenous compounds, alcoholic nitrogenous compounds, amide derivatives, and imide derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine.

Examples of suitable secondary aliphatic amines include dimethylamine, diethylamine, di-n-propylamine, di1so-propylamine, di-n-butylamine, di1so-butylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine.

Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine.

Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 1-methyl-2-pyridone, 4-pyrrolidinopyridine, 1-methyl-4-phenylpyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable carboxyl group-containing nitrogenous compounds include aminobenzoic acid, indolecarboxylic acid, and amino acid derivatives (e.g. nicotinic acid, alanine, alginine, aspartic acid, glutamic acid, glycine, histidine, isoleucine, glycyl leucine, leucine, methionine, phenylalanine, threonine, lysine, 3-aminopyrazine-2-carboxylic acid, and methoxyalanine).

Examples of suitable sulfonyl group-containing nitrogenous compounds include 3-pyridinesulfonic acid and pyridinium p-toluenesulfonate.

Examples of suitable hydroxyl group-containing nitrogenous compounds, hydroxyphenyl group-containing nitrogenous compounds and alcoholic nitrogenous compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine piperidine ethanol, 1-(2-hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)1sonicotinamide.

Examples of suitable amide derivatives include formamide, N-methylformamide, N,N-dimethylformamide, acetamide, N-methylacetamide, N,N-dimethylacetamide, propionamide, and benzamide.

Suitable imide derivatives include phthalimide, succinimide, and maleimide.

In addition, one or more selected from the basic compound of the following General Formula (B1) may also be comprised.

$$N(X)_m(Y)_{3-m} \quad (B)\text{-}1$$

In the above formula, m=1, 2 or 3. Side chains X may be the same or different, which can be represented by the following General Formulas (X)-1 to (X)-3. Side chains Y, which may be same or different, denote a hydrogen atom, or a straight-chained, branched or cyclic alkyl group of 1 to 20 carbon atoms wherein the alkyl group may comprise an ether group or a hydroxyl group. Additionally, X and X may be bonded together to form a ring.

Herein, $R^{300}$, $R^{302}$, and $R^{305}$ are each independently a straight-chained or branched alkylene group of 1 to 4 carbon atoms, and $R^{301}$ and $R^{304}$ are each independently a hydrogen atom, or a straight-chained, branched or cyclic alkyl group of 1 to 20 carbon atoms, which may comprise a hydroxy group, an ether group, an ester group, and a lactone ring or some of them.

The $R^{303}$ is a single bond, or a straight-chained or branched alkylene group of 1 to 4 carbon atoms. The $R^{306}$ is a straight-chained, branched or cyclic alkyl group of 1 to 20 carbon atoms, which may comprise a hydroxy group, an ether group, an ester group, and a lactone ring or some of them.

(X)-1

(X)-2

(X)-3

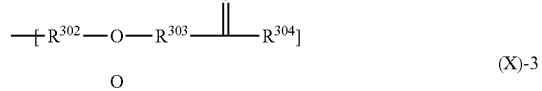

Specific examples of compounds represented by Formula (B)-1 are as follows: tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4,1-aza-15-crown-5,1-aza-18-crown-6, tris(2-formyloxyethyl)amine, tris(2-acetoxyethyl)amine, tris(2-propionyloxyethyl)amine, tris (2-butyryloxyethyl)amine, tris(2-isobutyryloxyethyl)amine, tris(2-valeryloxyethyl)amine, tris (2-pivaloyloxyxyethyl)amine, N,N-bis(2-acetoxyethyl)2-(acetoxyacetoxy)ethylamine, tris(2-methoxycarbonyloxyethyl)amine, tris(2-tertbutoxycarbonyloxyethyl)amine, tris[2-(2-oxopropoxy) ethyl]amine, tris[2-(methoxycarbonylmethyl)oxyethyl] amine, tris[2-(tert-butoxycarbonylmethyloxy)ethyl]amine, tris[2-(cyclohexyloxycarbonylmethyloxy)ethyl]amine, tris (2-methoxycarbonylethyl)amine, tris(2-ethoxycarbonylethyl)amine, N,N-bis(2-hydroxyethyl)2-(methoxycarbonyl) ethylamine, N,N-bis(2-acetoxyethyl)2-(methoxycarbonyl) ethylamine, N,N-bis(2-hydroxyethyl)2-(ethoxycarbonyl) ethylamine, N,N-bis(2-acetoxyethyl)2-(ethoxycarbonyl) ethylamine, N,N-bis(2-hydraoxyethyl)2-(2-methoxyethoxycarbonyl)ethylamine, N,N-bis (2-acetoxyethyl)2-(2-methoxyethoxycarbonyl)ethylamine, N,N-bis(2-hydroxyethyl)2-(2-hydroxyethoxycarbonyl)ethylamine, N,N-bis(2-acetoxyethyl)2-(2-acetoxyethoxycarbonyl)ethylamine, N,N-bis(2-hydroxyethyl)2-[(methoxycarbonyl)methoxycarbonyl]ethylamine, N,N-bis(2-acetoxyethyl)2-[(methoxycarbonyl)methoxycarbonyl] ethylamine, N,N-bis(2-hydroxyethyl)2-(2-oxopropoxycarbonyl)ethylamine, N,N-bis(2-acetoxyethyl) 2-(2-oxopropoxycarbonyl)ethylamine, N,N-bis(2-hydroxyethyl)2-(tetrahydrofurfuryloxycarbonyl) ethylamine, N,N-bis(2-acetoxyethyl)2-(tetrahydrofurfuryloxycarbonyl)ethylamine, N,N-bis(2-hydroxyethyl)2-[(2-oxotetrahydrofuran-3-yl)oxycarbonyl] ethylamine, N,N-bis(2-acetoxyethyl)2-[(2-oxotetrahydrofuran-3-yl)oxycarbonyl]ethylamine, N,N-bis (2-hydroxyethyl)2-(4-hydroxybutoxycarbonyl)ethylamine, N,N-bis(2-formyloxyethyl)2-(4-formyloxybutoxycarbonyl) ethylamine, N,N-bis(2-formyloxyethyl)2-(2-formyloxyethoxycarbonyl)ethylamine, N,N-bis(2-methoxyethyl)2-(methoxycarbonyl)ethylamine, N-(2-hydroxyethyl)bis[2-methoxycarbonyl)ethyl]amine, N-(2-acetoxyethyl)bis[2-(methoxycarbonyl)ethyl]amine, N-(2-hydroxyethyl)bis[2-(ethoxycarbonyl)ethyl]amine, N-(2-acetoxyethyl)bis[2-(ethoxycarbonyl)ethyl]amine, N-(3-hydroxy-1-propyl)bis [2-(methoxycarbonyl)ethyl]amine, N-(3-acetoxy-1-propyl) bis[2-(methoxycarbonyl)ethyl]amine), N-(2-methoxyethyl) bis[2-(methoxycarbonyl)ethyl]amine, N-butylbis [2-(methoxycarbonyl)ethyl]amine, N-butylbis[2-(2-methoxyethoxycarbonyl)ethyl]amine, N-methylbis(2-acetoxyethyl)amine, N-ethylbis(2-acetoxyethyl)amine, N-methylbis(2-pivaloyloxyethyl)amine, N-ethylbis[2-(methoxycarbonyloxy)ethyl]amine, N-ethylbis[2-(tert-butoxycarbonyloxy)ethyl]amine, tris(methoxycarbonylmethyl)amine, tris(ethoxycarbonylmethyl)amine, N-butylbis (methoxycarbonylmethyl)amine, N-hexylbis (methoxycarbonylmethyl)amine, and β-(diethylamino)-δ-valerolactone. However, the present invention is not limited to these compounds.

Further, one or more basic compounds having a cyclic structure of the following Formula (B)-2 can also be added.

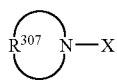
(B)-2

Herein, X is the same as mentioned above, and $R^{307}$ is a straight-chained or branched alkylene group of 2 to 20 carbon atoms, which may comprise at least one of a carbonyl group, an ether group, an ester group, and sulfide.

Specific examples of B-2 include 1-[2-(methoxymethoxy) ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy) methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyl)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino) propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl) propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, and 2-methoxyethyl morpholinoacetate.

Further, a basic compound having a cyano group represented by Formulas (B)-3 to (B)-6 can be added.

(B)-3

(B)-4

(B)-5

(B)-6

Herein, X, $R^{307}$ and m are each the same as mentioned above. The $R^{108}$ and $R^{309}$, which may be same or different, are each independently a straight-chained or branched alkylene group of 1 to 4 carbon atoms, which may be the same or different.

Examples of bases having cyano groups include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-

(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile), diethylaminoacetonitrile, N,N-bis(2-hydroxyethyl)aminoacetonitrille, N,N-bis(2-acetoxyethyl)aminoacetonitrille, N,N-bis(2-formyloxyethyl)aminoacetonitrille, N,N-bis(2-methoxyethyl)aminoacetonitrille, N,N-bis[2-(methoxymethoxy)ethyl]aminoacetonitrille, methyl N-cyanamethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl]aminoacetonitrile, N-(cyanomethyl)-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile), 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis (2-hydroxyethyl)-3-aminopropionate, 2-cyanoethyl N,N-bis(2-(acetoxyethyl))-3-aminopropionate, 2-cyanoethyl N,N-bis(2-formyloxyethyl)-3-aminopropionate, 2-cyanoethyl N,N-bis (2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

The basic compound may be formulated in an amount of 0.001 to 10 parts by weight, and preferably 0.01 to 1 part by weight, per 1 part by weight of the photoacid generator. Less than 0.001 part by weight of the basic compound may fail to achieve the desired effects thereof, while use of more than 10 parts by weight may result in too low a sensitivity and resolution.

The resist material of the present invention may comprise a compound (organic acid) containing a ≡C—COOH group in a molecule.

Exemplary, non-limiting compounds containing a —C—COOH group include one or more compounds selected from Groups I and II below. Comprising this compound may improve the PED stability of the resist and improve edge roughness on nitride film substrates.

[Group I]

Compounds in which the hydrogen atoms on the phenolic hydroxyl group of the compound of General Formulas (A1) to (A10) below have been partially or entirely substituted with $R^{40}$—COOH (wherein $R^{401}$ is a straight-chained or branched alylene group of 1 to 10 carbon atoms), and in which the mole fraction C/(C+D) of phenolic hydroxyl groups (C) to ≡C—COOH groups (D) in the molecule is from 0.1 to 1.0.

[Group II]

Compounds of General Formulas (A11) to (A15) below.

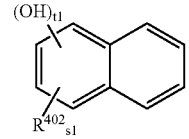

A1

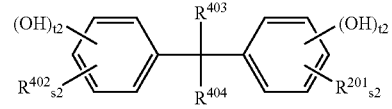

A2

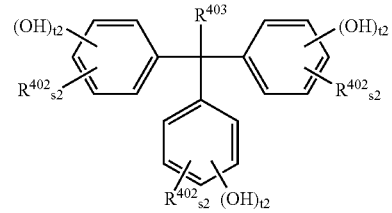

A3

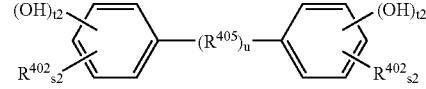

A4

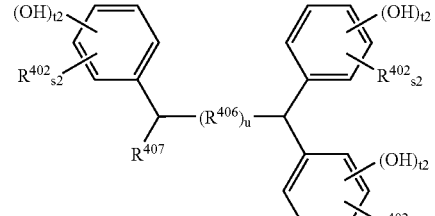

A5

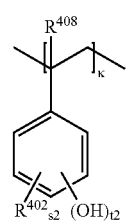

A6

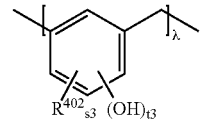

A7

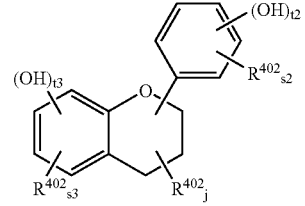

A8

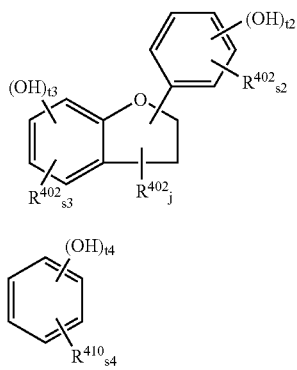
A9

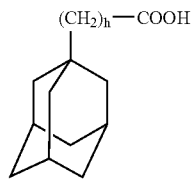
A14

A10

Herein, $R^{408}$ is a hydrogen atom or methyl group. $R^{402}$ and $R^{403}$ are each independently a hydrogen atom or a straight-chained or branched alkyl or alkenyl group of 1 to 8 carbon atoms. $R^{404}$ is a hydrogen atom, a straight-chained or branched alkyl or alkenyl group of 1 to 8 carbon atoms, or a —$(R^{409})_k$—COOR' group (wherein R' is a hydrogen atom or —$R^{409}$—COOH, and k is 0 or 1). $R^{405}$ is —$(CH_2)_i$— (wherein i is an integer from 2 to 10), an arylene group of 6 to 10 carbon atoms, a carbonyl group, a sulfonyl group, an oxygen atom, or a sulfur atom. $R^{406}$ is an alkylene group of 1 to 10 carbon atoms, an arylene group of 6 to 10 carbon atoms, a carbonyl group, a sulfonyl group, an oxygen atom or a sulfur atom. $R^{407}$ is a hydrogen atom, a straight-chained or branched alkyl or alkenyl group of 1 to 8 carbon atoms, or a hydroxyl-substituted phenyl or naphthyl group. $R^{409}$ is a straight-chained or branched alkylene group of 1 to 10 carbon atoms. $R^{410}$ is hydrogen, a straight-chained or branched alkyl or alkenyl group of 1 to 8 carbon atoms, or a —$R^{411}$—COOH group. $R^{411}$ is a straight-chained or branched alkylene group of 1 to 10 carbon atoms. The letter j is an integer from 0 to 5. The u is 0 or 1. The s1, t1, s2, t2, s3, t3, s4 and t4 are numbers which satisfy s1+t1=8, s2+t2=5, s3+t3=4, and s4+t4=6, and are such that each phenyl skeleton has at least one hydroxyl group. κ is a number such that the compound of Formula (A6) may have a weight-average molecular weight of 1,000 to 5,000. λ is a number such that the compound of Formula (A7) may have a weight-average molecular weight of 1,000 to 10,000.

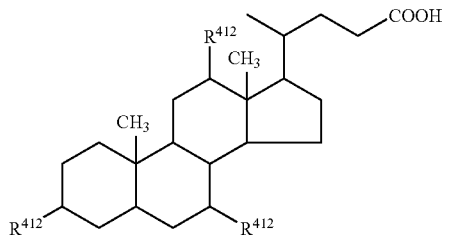
A11

A12

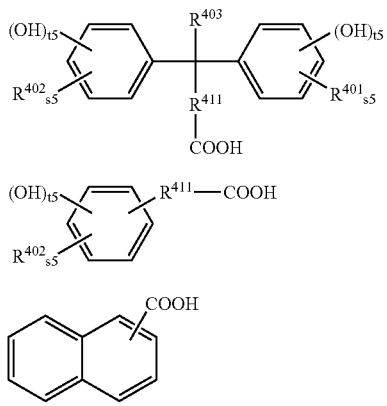
A13

A15

Herein, $R^{402}$, $R^{403}$ and $R^{411}$ are each as defined above. $R^{412}$ is a hydrogen atom or hydroxyl group. The s5 and t5 are numbers which satisfy s5≧0, t5≧0 and s5+t5=5. The h' is 0 or 1.

Compounds shown by the following General Formulas AI-1 to AI-14 and AII-1 to AII-10 can be mentioned as specific examples of this component, but the present invention is not limited to these.

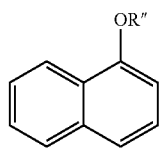
AI-1

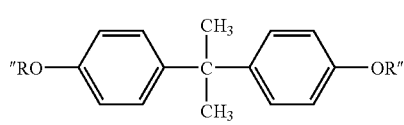
AI-2

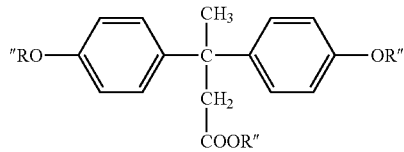
AI-3

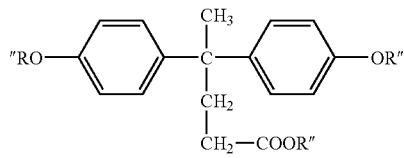
AI-4

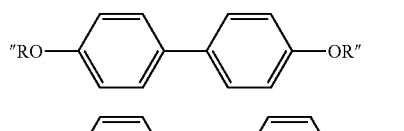
AI-5

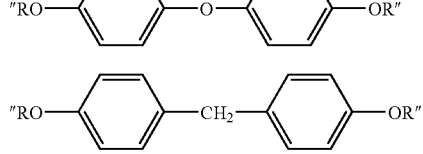
AI-6

AI-7

-continued
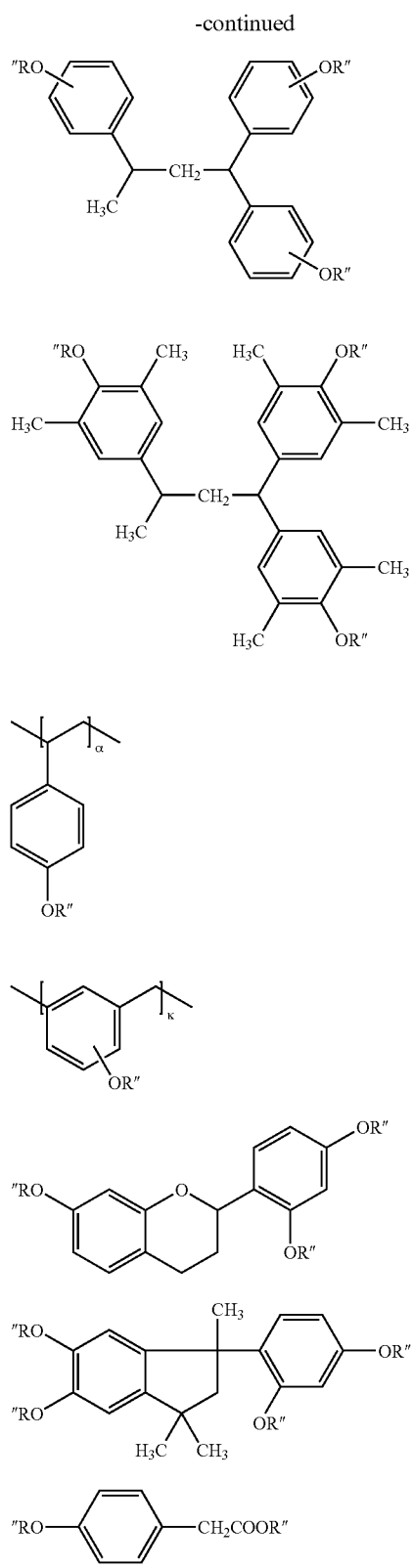
AI-8
AI-9
AI-10
AI-11
AI-12
AI-13
AI-14
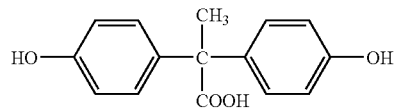 AII-1
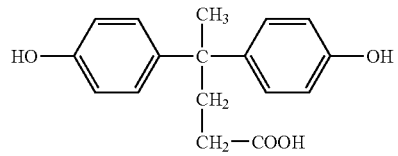 AII-2
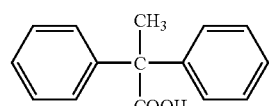 AII-3
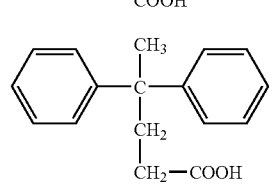 AII-4
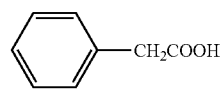 AII-5
 AII-6
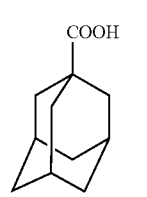 AII-7
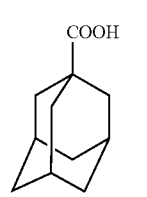 AII-8
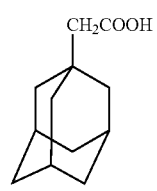 AII-9
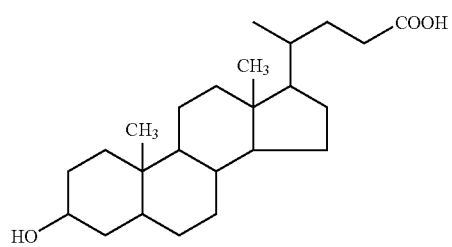 AII-10
In the above Formulas, R″ is a hydrogen atom or a CH$_2$COOH group such that the CH$_2$COOH group accounts for 10 to 100 mol % of R″ in each compound. α and κ are as defined above.

The compound containing a ≡C—COOH group within the molecule may be used singly or as combinations of two or more thereof.

The compound containing a ≡C—COOH group within the molecule may be added in an amount ranging from 0 to 5 parts by weight, preferably 0.1 to 5 parts by weight, more preferably 0.1 to 3 parts by weight, further preferably 0.1 to 2 parts by weight, per 100 parts by weight of the base resin. More than 5 parts by weight of the compound may reduce the resolution of the resist material.

The resist material of the present invention may additionally comprise an acetylene alcohol derivative for the purpose of enhancing the shelf stability.

Preferred acetylene alcohol derivatives are those having the General Formula (S1) or (S2) below.

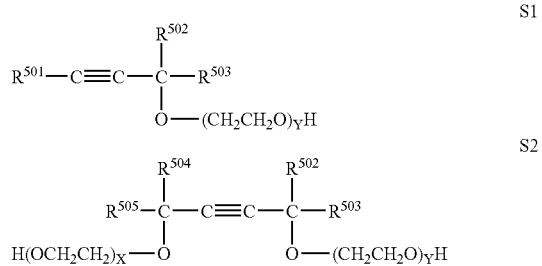

In the above Formulas, $R^{501}$, $R^{502}$, $R^{503}$, $R^{504}$, and $R^{505}$ are each a hydrogen atom or a straight-chained, branched, or cyclic alkyl group of 1 to 8 carbon atoms. X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfinol 61, Surfinol 82, Surfinol 104, Surfinol 104E, Surfinol 104H, Surfinol 104A, Surfinol TG, Surfinol PC, Surfinol 440, Surfinol 465, and Surfinol 485 from Air Products and Chemicals Inc., and Surfinol E1004 from Nisshin Chemical Industry Co., Ltd.

The acetylene alcohol derivative is preferably added in an amount of 0.01 to 2% by weight, and more preferably 0.02 to 1% by weight, per 100% by weight of the resist material. Less than 0.01% by weight may be ineffective for improving coating characteristics and shelf stability, whereas more than 2% by weight would result in a resist having a low resolution.

The resist material of the present invention may comprise, as an optional component, a surfactant which is commonly used for improving the coating characteristics. The optional component may be added in a conventional amount as long as this does not negate the effects of the present invention.

Nonionic surfactants are preferred, examples of which include perfluoroalkylpolyoxyethylene ethanols, fluorinated alkyl esters, perfluoroalkylamine oxides, perfluoroalkyl EO(ethylene oxide)-addition products, and fluorine-containing organosiloxane compounds. Useful surfactants are commercially available under the trade names Florad "FC-430" and "FC-431" from Sumitomo 3M Ltd., Surflon "S-141" and "S-145" from Asahi Glass Co. Ltd., Unidain "DS-401", "DS-403" and "DS-451" from Daikin Industries Ltd., Megafac "F-8151" from Dai Nippon Ink & Chemicals Incorporated, and "X-70-092", and "X-70-093" from Shin-Etsu Chemical Co., Ltd. Preferred surfactants are Florad "FC-430" from Sumitomo 3M Ltd., and "X-70-093" from Shin-Etsu Chemical Co., Ltd.

Pattern formation using the resist material of the present invention may be carried out by a known lithographic technique. For example, the resist material may be applied onto a substrate such as a silicon wafer by spin coating or the like to form a resist film having a thickness of 0.3 to 2.0 μm, which may be then pre-baked on a hot plate at 60 to 180° C. for 1 to 10 minutes, and preferably at 80 to 150° C. for 1 to 5 minutes. Thereafter, a patterning mask having the desired pattern may be placed over the resist film, the film may be then exposed through the mask to an KrF or ArF excimer laser beam in a dose of 1 to 100 mJ/cm$^2$, preferably 5 to 50 mJ/cm$^2$, and may be subjected to a post-exposure bake (PEB) on a hot plate at 60 to 180° C. for 1 to 5 minutes, and preferably at 80 to 150° C. for 1 to 3 minutes. Thereafter, development may be carried out using as the developer an aqueous alkali solution, such as a 0.1 to 5% by weight, preferably 2 to 3% by weight aqueous solution of tetramethylammonium hydroxide (TMAH), this being done by a conventional method such as dipping, puddling or spraying for a period of 0.1 to 3 minutes, and preferably 0.5 to 2 minutes. These steps may result in the formation of the desired pattern on the substrate. The desired pattern may not be obtainable outside the upper and lower limits of the above range.

The present invention will hereinafter be described in detail with reference to Synthetic Examples, Examples, and Comparative Examples, but the present invention is not limited to these examples.

SYNTHETIC EXAMPLE 1

Synthesis of an Aqueous Solution of 2-Oxo-2-phenylethylthiacyclopentaniumbromide The 2-bromoacetophenone of 4.97 g (0.025 moles) was dissolved in nitromethane of 9.5 g. Tetrahydrothiophene of 2.2 g (0.025 moles) was added at room temperature, and was matured as it is for two hours at room temperature. A reaction liquid was hardened by the progression of reactions. Solids were dissolved by adding 70 g of water and 50 g of diethyl ether. A water layer was separated and washed with 50 g of diethyl ether of 50 g so that lipophilic impurities were removed.

An anion exchange with various bisperfluoroalkylsulfoneimides was performed using this aqueous solution.

Synthesis of 2-Oxo-2-phenylethylthiacyclopentaniumbis(perfluoroethylsulfonyl)imide When 9.5 g (0.025 moles) of bis(perfluoroethylsulfonyl)imide was added to the aforementioned aqueous solution of 2-oxo-2-phenylethylthiacyclopentaniumbromide, oily matter was separated therefrom. This oily matter was extracted by 1000 g of dichloromethane. An organic layer was washed with 50 g of water four times, and the organic layer was concentrated by a rotary evaporator, thus obtaining 15 g of oily substance. The 50 g of diethyl ether was added to this oily substance for crystallization. Resultant crystals were subjected to filtration under vacuum, and drying. As a result, 13 g of white crystals was obtained. The yield was 66%.

The obtained sample was subjected to a TOF-MS analysis, which was carried by measurement apparatus Kratos Kompact Probe MALDI-TOFMS at acceleration voltages of 5 kV for both a cation and an anion with mass calibration of $C_{60}$, and straight flight. A cation mass peak of 207.3 and an anion peak of 379.9 were obtained. The mass of the cation coincided with that of 2-oxo-2-phenylethylthiacyclopentanium, and the mass of the anion coincided with that of bis(perfluoroethylsulfonyl)imide.

The analytic results of IR and $^1$H-NMR were as follows.
IR (thin film): ν=3077, 3031, 2975, 2929, 1687, 1598, 1583, 1452, 1430, 1386, 1351, 1332, 1230, 1174, 1141, 1083, 995, 975, 906, 883, 775, 755, 740, 684, 640, 613, 568, 536, and 524 cm$^{-1}$ $^1$H-NMR (300 MHz in CDCl$_3$): δ=7.617-7.666 ppm (Ha, 1H, triplet), 7.424-7.482 ppm (Hb, 2H, triplet), 7.911-7.935 ppm (Hc, 2H, doublet), 5.117 ppm (Hd, 2H, singlet), 3.473-3.720 ppm (He, 4H, multiplet), and 2.256-2.500 (Hf, 4H, multiplet).

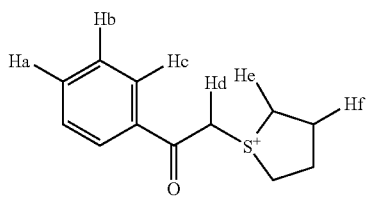

SYNTHETIC EXAMPLE 2

Synthesis of 2-Oxo-2-phenylethylthiacyclopentanium Bis (perfluoro-n-butylsulfonyl)imide When 14.5 g (0.025 moles) of bis(perfluoro-n-butylsulfonyl)imide was added to the aforementioned aqueous solution of 2-oxo-2-phenylethylthiacyclopentaniumbromide, oily matter was separated therefrom. This oily matter was extracted by 150 g of dichloromethane. An organic layer was washed with 80 g of water four times, and the organic layer was concentrated by a rotary evaporator, thus obtaining 18 g of oily substance. The 50 g of diethyl ether was added to this oily substance for crystallization. Resultant crystals were subjected to filtration under vacuum and drying. As a result, 13.5 g of white crystals were obtained. The yield was 68%.

The obtained sample was subjected to a TOF-MS analysis. A cation mass peak of 207.3 and an anion peak of 579.9 were obtained. The mass of the cation coincided with that of 2-oxo-2-phenylethylthiacyclopentanium, and the mass of the anion coincided with that of bis(perfluoro-n-butylsulfonyl)imide.

The analytic results of IR and $^1$H-NMR were as follows.
IR (thin film): ν=3066, 3043, 3023, 2966, 2921, 1685, 1598, 1583, 1452, 1430, 1386, 1359, 1326, 1290, 1257, 1214, 1197, 1153, 1062, 1035, 991, 887, 875, 806, 738, 721, 701, 688, 651, 636, 615, 595, 576, 536, and 512 cm$^{-1}$ $^1$H-NMR (300 MHz in CDCl$_3$): δ=7.617-7.666 ppm (Ha, 1H, triplet), 7.424-7.482 ppm (Hb, 2H, triplet), 7.911-7.935 ppm (Hc, 2H, doublet), 5.117 ppm (Hd, 2H, singlet), 3.473-3.720 ppm (He, 4H, multiplet), and 2.256-2.500 ppm (Hf, 4H, multiplet)

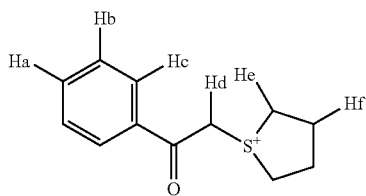

EXAMPLES

An evaluation of sensitivity and resolution were carried out when sulfonium salts and iodonium salts represented by the following Formulas (PAG 1 to PAG 9) were added in resists.

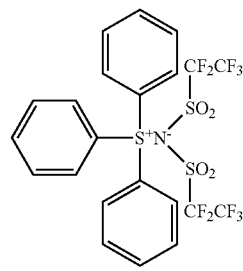
(PAG 1)

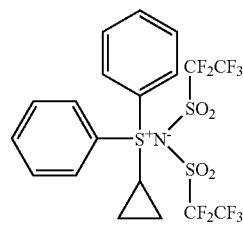
(PAG 2)

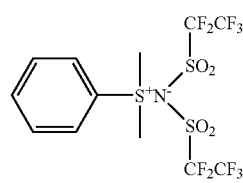
(PAG 3)

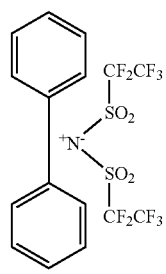
(PAG 4)

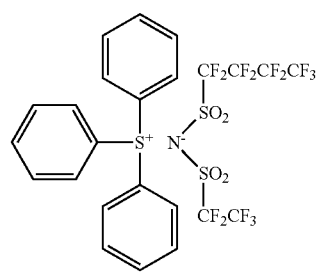
(PAG 5)

-continued
(PAG 6)
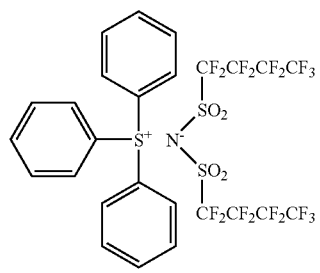
(PAG 7)
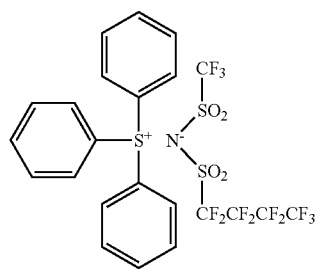
(PAG 8)
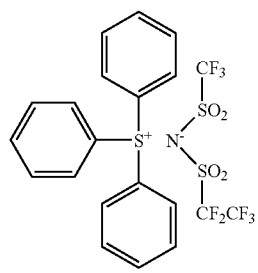
(PAG 9)
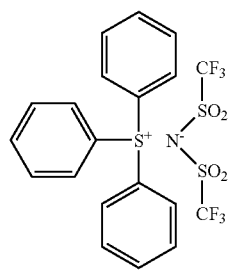
(PAG 10)
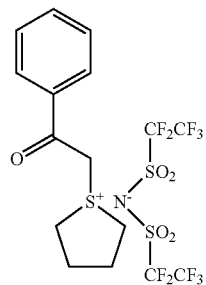
-continued
(PAG 11)
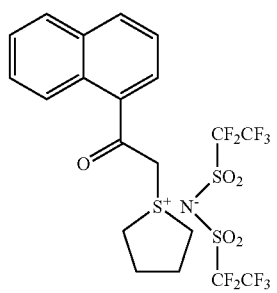
(PAG 12)
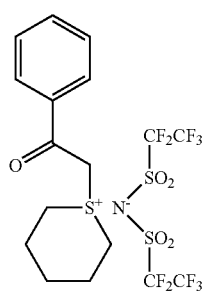
(PAG 13)
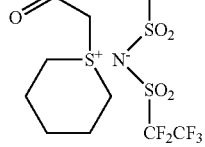
(PAG 14)
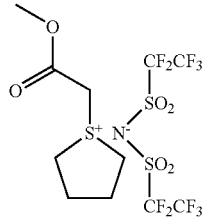
(PAG 15)
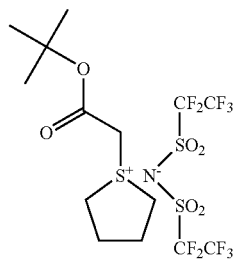

-continued (PAG 16)

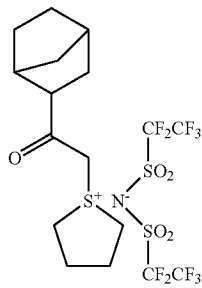

Examples 1 to 40

Evaluation of Resist Resolution

Sulfonium salts and iodonium salts (PAG 1 to PAG 9 represented by the above formulas were used as photoacid generators, while polymers (Polymers 1 to 26) represented by the following formulas were used as the base resin. Dissolution inhibitors (DRR 1 to DRR 4) represented by the following formulas, basic compounds, and compounds (ACC 1 and ACC 2) having the group represented by ≡C—COOH in the molecule defined by a formula as organic acid were dissolved in a solvent that contains 0.01 wt % FC-430 (of Sumitomo 3M Ltd.) according to the formulation shown in the table, and resist materials were blended. Further, each composition was filtered with a Teflon filter of 0.2 μm, and respective resist liquids were prepared.

(Polymer 1)

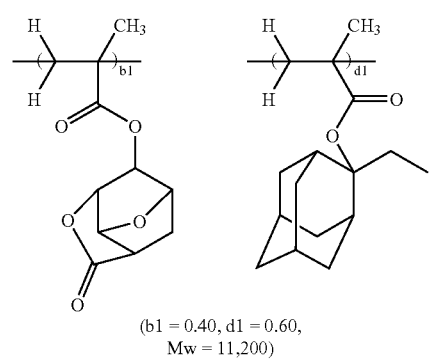

(b1 = 0.40, d1 = 0.60, Mw = 11,200)

(Polymer 2)

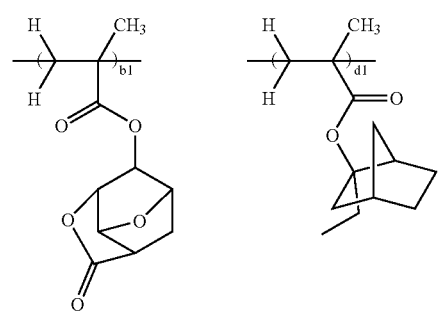

(b1 = 0.50, d1 = 0.50, Mw = 11,800)

-continued (Polymer 3)

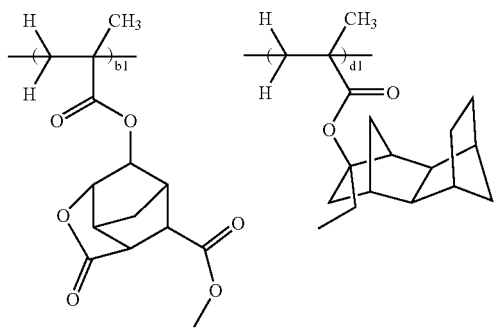

(b1 = 0.50, d1 = 0.50, Mw = 10,900)

(Polymer 4)

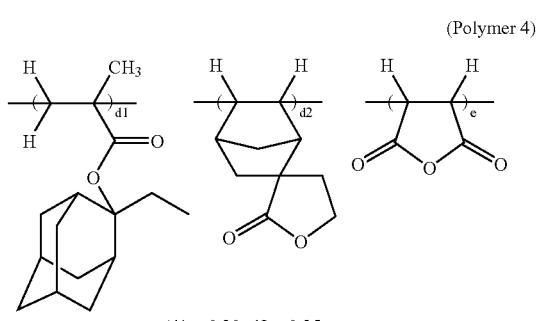

(d1 = 0.30, d2 = 0.35, e = 0.35, Mw = 10,500)

(Polymer 5)

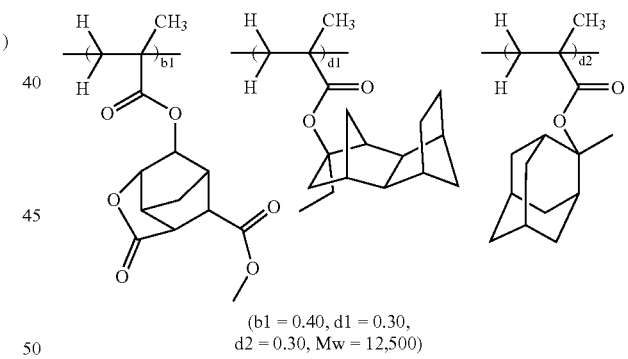

(b1 = 0.40, d1 = 0.30, d2 = 0.30, Mw = 12,500)

(Polymer 6)

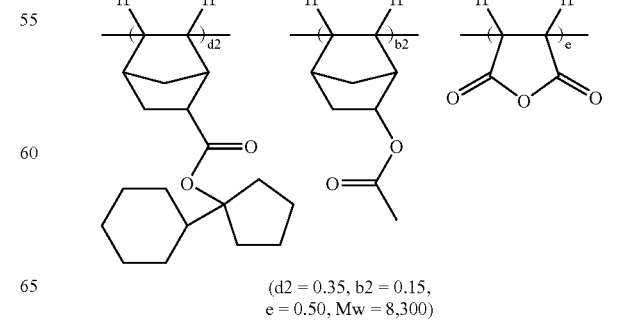

(d2 = 0.35, b2 = 0.15, e = 0.50, Mw = 8,300)

(Polymer 7)
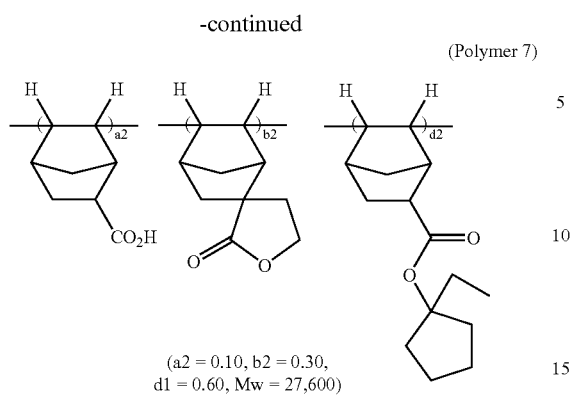
(a2 = 0.10, b2 = 0.30,
d1 = 0.60, Mw = 27,600)
(Polymer 8)
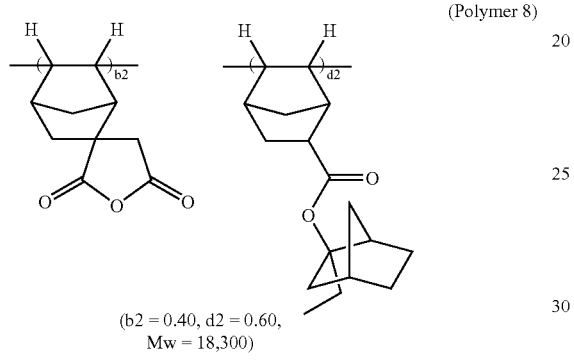
(b2 = 0.40, d2 = 0.60,
Mw = 18,300)
(Polymer 9)
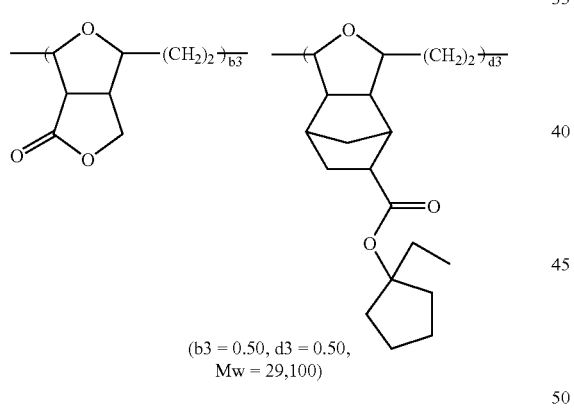
(b3 = 0.50, d3 = 0.50,
Mw = 29,100)
(Polymer 10)
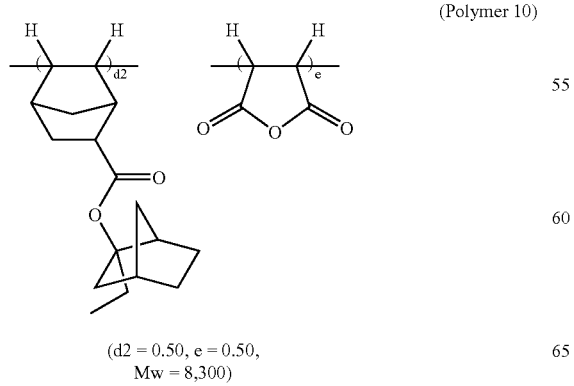
(d2 = 0.50, e = 0.50,
Mw = 8,300)
(Polymer 11)
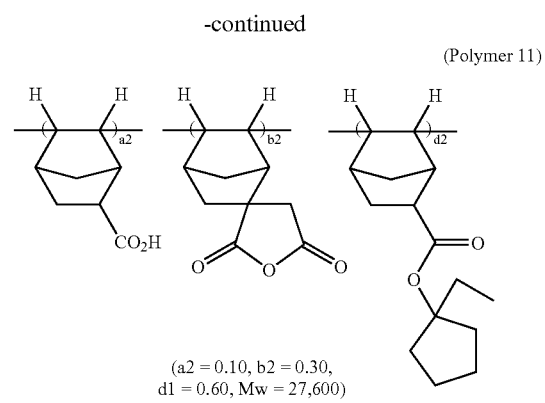
(a2 = 0.10, b2 = 0.30,
d1 = 0.60, Mw = 27,600)
(Polymer 12)
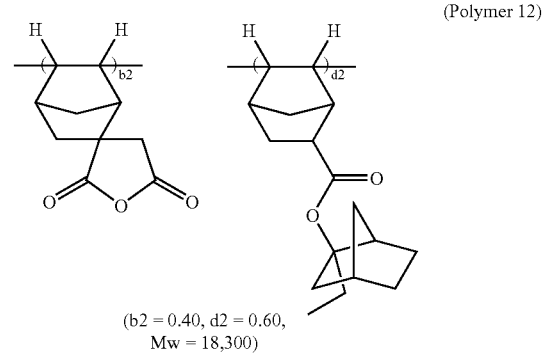
(b2 = 0.40, d2 = 0.60,
Mw = 18,300)
(Polymer 13)
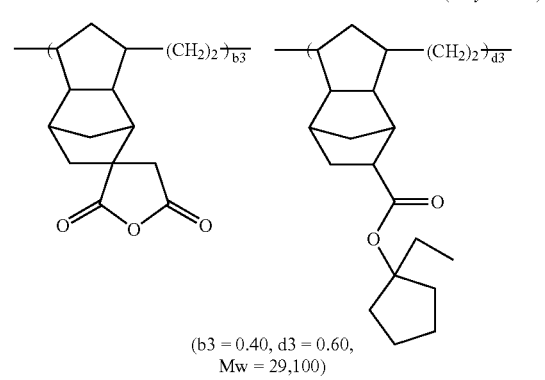
(b3 = 0.40, d3 = 0.60,
Mw = 29,100)
(Polymer 14)
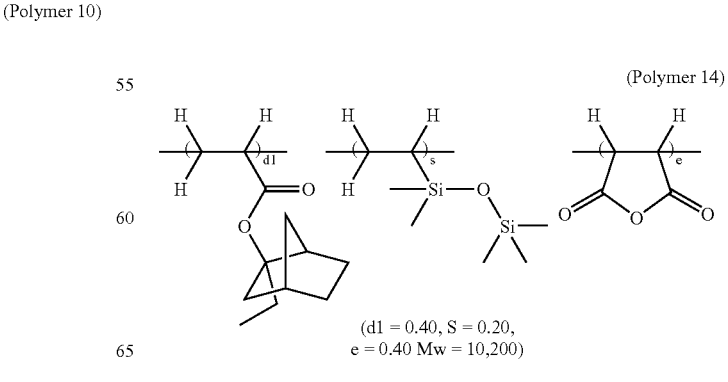
(d1 = 0.40, S = 0.20,
e = 0.40 Mw = 10,200)

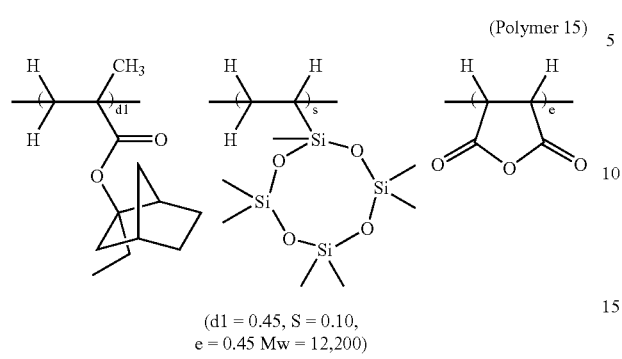
(Polymer 15)
(d1 = 0.45, S = 0.10,
e = 0.45 Mw = 12,200)
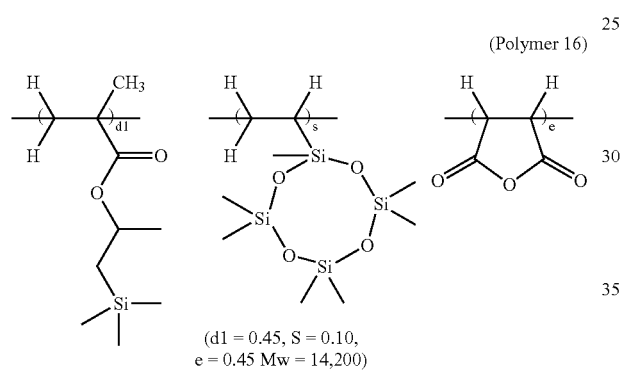
(Polymer 16)
(d1 = 0.45, S = 0.10,
e = 0.45 Mw = 14,200)
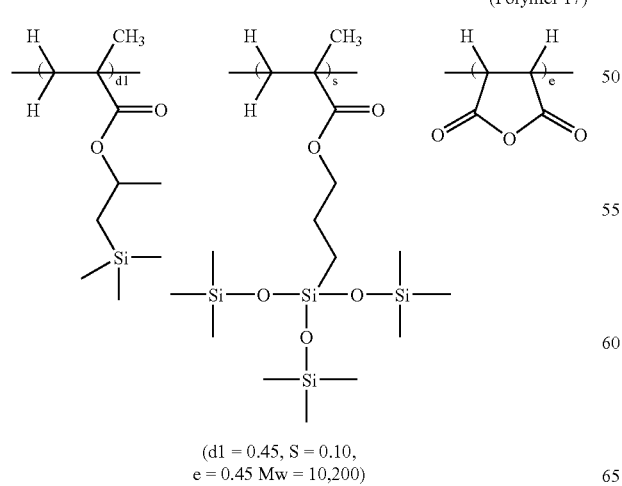
(Polymer 17)
(d1 = 0.45, S = 0.10,
e = 0.45 Mw = 10,200)
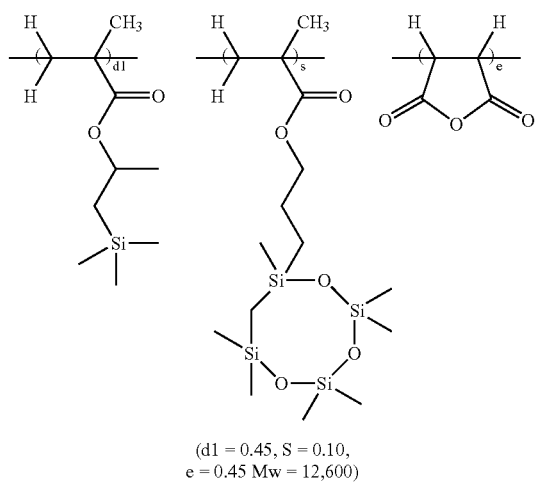
(Polymer 18)
(d1 = 0.45, S = 0.10,
e = 0.45 Mw = 12,600)
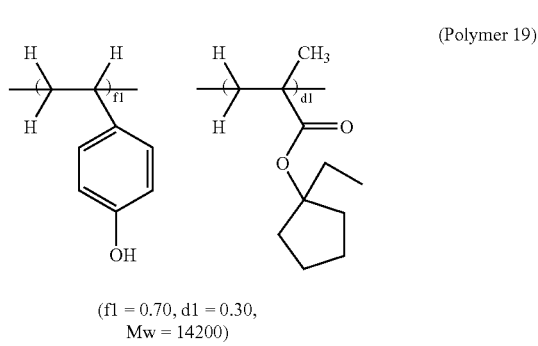
(Polymer 19)
(f1 = 0.70, d1 = 0.30,
Mw = 14200)
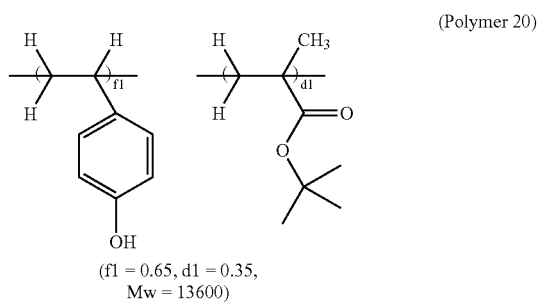
(Polymer 20)
(f1 = 0.65, d1 = 0.35,
Mw = 13600)
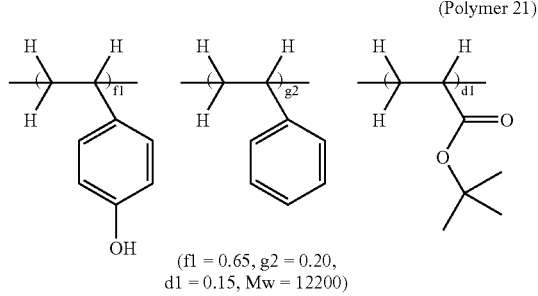
(Polymer 21)
(f1 = 0.65, g2 = 0.20,
d1 = 0.15, Mw = 12200)

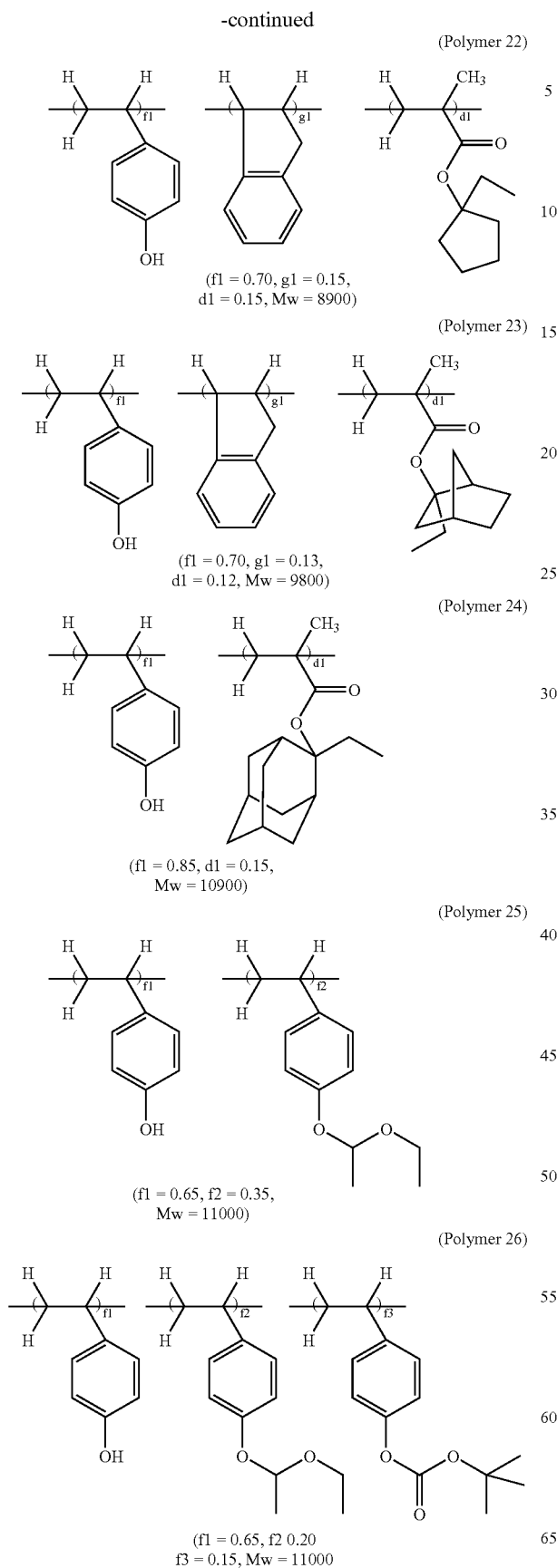
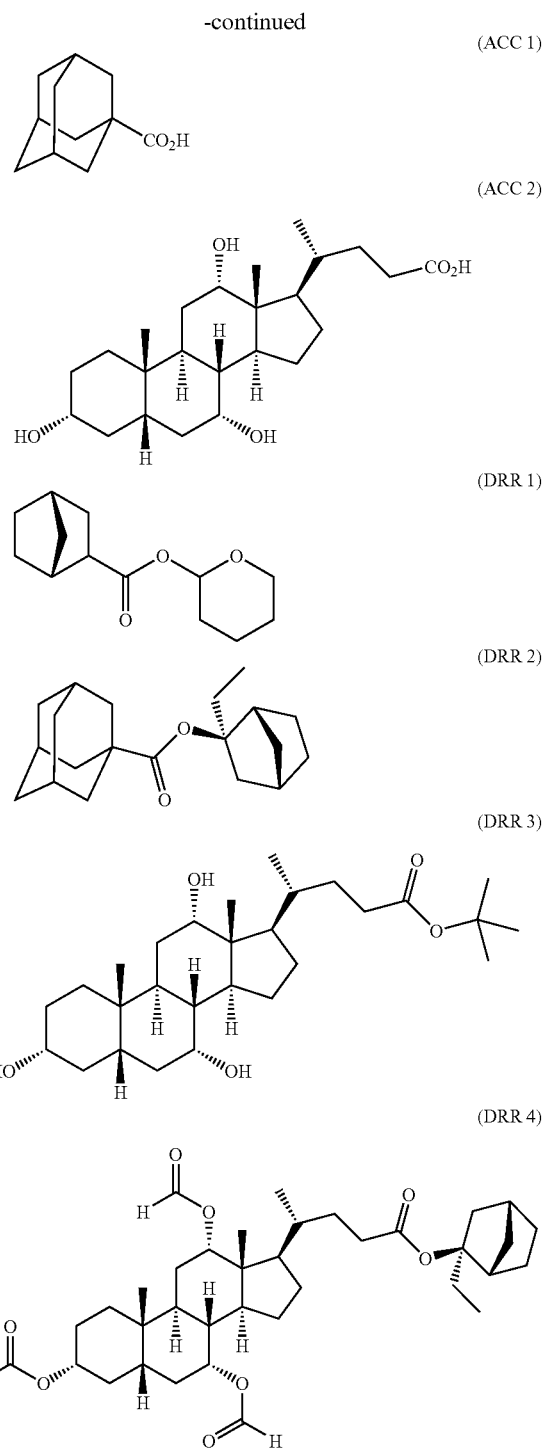

Example of ArF Exposure

Resist materials using Polymers 1 to 18 were subjected to an Arf (wavelength 193 nm) exposure.

An antireflection film solution (AR 19 of Shipley Co.) was applied onto a silicon substrate. Thereafter, the substrate of an antireflection film (thickness of 82 nm) which was formed by baking for 60 seconds at 200° C., and was subjected to the spin coating of a resist solution, and was baked with a hot plate for 60 seconds at 110° C., thereby forming a resist film having a thickness of 300 nm. This was exposed by use of an ArF excimer laser micro-stepper (Nikon Corporation, NA=0.55, σ0.7), was then subjected to baking (PEB) for 90 seconds at 110° C., and was developed with an aqueous solution of 2.38% by weight tetramethylammoniumhydroxide for 30 seconds.

The resist materials were evaluated as follows. On the supposition that the exposure which provides a 1:1 resolution of a 0.20 μm line-and-space pattern is an optimum exposure (Eop, mJ/cm²), the resolution of the resist under evaluation was defined as the minimum line width (μm) of the lines and spaces that separated at this dose. The line width of an isolated line of a 1:10 line-and-space with the same exposure was measured, and a value calculated by subtraction of the line width of the isolated line from the line width of the group line was defined as a dimensional difference (I/G bias) between the sparse pattern and the dense pattern. The ruggedness of the group line was also measured, and was defined as line-edge roughness. The results are shown in Table 1.

Example of KrF Exposure

Resist materials using Polymers 19 to 26 were subjected to a KrF (wavelength 248 nm) exposure.

An antireflection film solution (DUV-30 of Brewer Science Co., Ltd.) was applied onto a silicon substrate. Thereafter, the substrate of an antireflection film (thickness of 55 nm) which was formed by baking for 60 seconds at 200° C. was subjected to the spin coating of a resist solution, and was baked with a hot plate for 60 seconds at 100° C., thereby forming a resist film having a thickness of 400 nm. This was exposed by use of a KrF excimer laser scanner (S203B of Nikon Corporation, NA=0.68, s=0.75), was then subjected to baking (PEB) for 90 seconds at 110° C., and was developed with an aqueous solution of 2.38% by weight tetramethylammoniumhydroxide for 60 seconds.

The resist materials were evaluated as follows. On the supposition that the dose which provides a 1:1 resolution of a 0.18 μm line-and-space pattern is an optimum exposure (Eop, mJ/cm²), the resolution of the resist under evaluation was defined as the minimum line width (μm) of the lines and spaces that separated at this dose. The line width of an isolated line of a 1:10 line-and-space with the same exposure was measured, and a value calculated by subtraction of the line width of the isolated line from the line width of the group line was defined as a dimensional difference (I/G bias) between the sparse pattern and the dense pattern. The ruggedness of the group line was also measured, and was defined as line-edge roughness. The results are shown in Table 2.

The Formulation and test results of the respective resist materials are shown in Table 1. The solvents and basic compounds of Table 1 are as follows.
PGMEA: propyleneglycolmethylether acetate,
CyHO: cyclohexanone,
PG/EL: mixed solvent of 70% PGMEA and 30% ethyl lactate,
TBA: tributylamine,
TEA: triethanolamine,
TMMEA: trismethoxymethoxyethylamine,
TMEMEA: trismethoxyethoxymethoxyethylamine,
AAA: tris(2-acetoxyethyl)amine, and
AACN: N,N-bis(2-acetoxyethyl)-3-aminopropiononitrile

COMPARATIVE EXAMPLE

For comparison purposes, the sulfonium salts (PAG10 to PAG15) of the following Formulas were examined with respect to the sensitivity and resolution of resist materials formulated therewith.

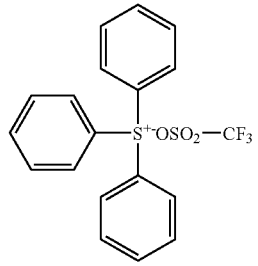

(PAG 10)

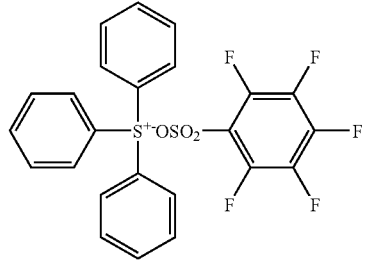

(PAG 11)

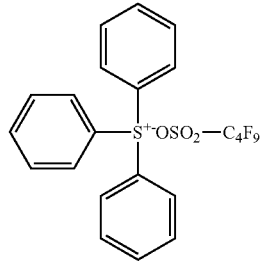

(PAG 12)

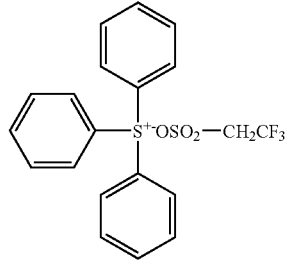

(PAG 13)

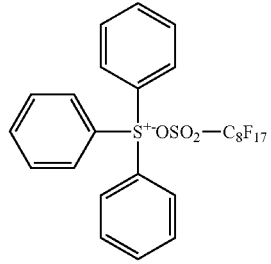

(PAG 14)

(PAG 15)

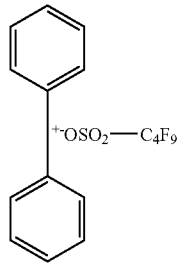

Comparative Examples 1 to 6

Resist materials were prepared according to the formulation of Table 3 by use of the sulfonium salts (PAG10 to PAG15) of the above formulas in the same way as above, and exposure was carried out by use of an ArF micro-stepper in the same way as above. Thereby, an evaluation was made of the sensitivity and resolution.

The formulation and test results of the respective resist materials are shown in Table 3.

From the results of Tables 1, 2, and 3, it was ascertained that the resist materials of the present invention were superior to the conventional ones in sensitivity, resolution, line-edge roughness, and I/G bias.

TABLE 1

| Example | Resin (part by weight) | Photoacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 1 | Polymer 1 (80) | PAG1 (1.5) | | TBA (0.10) | PGMEA (480) | 35.0 | 0.15 | 25 | 5.0 |
| 2 | Polymer 1 (80) | PAG2 (1.5) | | TBA (0.10) | PGMEA (480) | 31.0 | 0.15 | 29 | 6.0 |
| 3 | Polymer 1 (80) | PAG3 (1.5) | | TBA (0.10) | PGMEA (480) | 28.0 | 0.15 | 35 | 6.3 |
| 4 | Polymer 1 (80) | PAG4 (1.5) | | TBA (0.10) | PGMEA (480) | 45.0 | 0.15 | 20 | 7.2 |
| 5 | Polymer 1 (80) | PAG5 (2) | | TBA (0.10) | PGMEA (480) | 42.0 | 0.15 | 19 | 8.2 |
| 6 | Polymer 1 (80) | PAG6 (2) | | TBA (0.10) | PGMEA (480) | 50.0 | 0.16 | 12 | 8.5 |
| 7 | Polymer 1 (80) | PAG7 (2) | | TBA (0.10) | PGMEA (480) | 50.0 | 0.16 | 29 | 8.5 |
| 8 | Polymer 1 (80) | PAG8 (2) | | TBA (0.10) | PGMEA (480) | 50.0 | 0.16 | 35 | 3.6 |
| 9 | Polymer 1 (80) | PAG9 (2) | | TBA (0.10) | PGMEA (480) | 50.0 | 0.16 | 40 | 4.2 |
| 10 | Polymer 1 (80) | PAG10 (4) | | TBA (0.10) | PGMEA (480) | 32.0 | 0.16 | 45 | 3.1 |
| 11 | Polymer 1 (80) | PAG11 (6) | | TBA (0.10) | PGMEA (480) | 65.0 | 0.16 | 42 | 3.0 |
| 12 | Polymer 1 (80) | PAG12 (3) | | TBA (0.10) | PGMEA (480) | 28.0 | 0.16 | 41 | 3.5 |
| 13 | Polymer 1 (80) | PAG13 (7) | | TBA (0.10) | PGMEA (480) | 45.0 | 0.16 | 42 | 3.6 |
| 14 | Polymer 1 (80) | PAG14 (7) | | TBA (0.10) | PGMEA (480) | 35.0 | 0.16 | 45 | 3.3 |
| 15 | Polymer 1 (80) | PAG15 (6) | | TBA (0.10) | PGMEA (480) | 31.0 | 0.16 | 48 | 3.8 |
| 16 | Polymer 1 (80) | PAG16 (6) | | TBA (0.10) | PGMEA (480) | 55.0 | 0.16 | 41 | 3.5 |
| 17 | Polymer 1 (80) | PAG10 (2) PAG1 (2) | | TBA (0.10) | PGMEA (480) | 28.0 | 0.16 | 39 | 3.7 |
| 18 | Polymer 1 (80) | PAG10 (2) PAG12 (1) | | TBA (0.10) | PGMEA (480) | 26.0 | 0.16 | 42 | 3.8 |

TABLE 2

| Example | Resin (part by weight) | Photoacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 19 | Polymer 1 (80) | PAG10 (2) PAG15 (1) | | TBA (0.10) | PGMEA (480) | 42.0 | 0.16 | 32 | 4.2 |

TABLE 2-continued

| Example | Resin (part by weight) | Photacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 20 | Polymer 2 (80) | PAG1 (1.5) | | TBA (0.10) | PGMEA (480) | 22.0 | 0.16 | 33 | 3.6 |
| 21 | Polymer 3 (80) | PAG1 (1.5) | | TBA (0.10) | PGMEA (480) | 15.0 | 0.15 | 38 | 2.2 |
| 22 | Polymer 4 (80) | PAG1 (1.5) | | TBA (0.10) | PGMEA (480) | 25.0 | 0.15 | 13 | 8.8 |
| 23 | Polymer 5 (80) | PAG1 (1.5) | | TBA (0.10) | PGMEA (480) | 39.0 | 0.17 | 19 | 5.6 |
| 24 | Polymer 6 (80) | PAG1 (1.5) | | TBA (0.10) | PGMEA (480) | 29.0 | 0.17 | 30 | 6.3 |
| 25 | Polymer 7 (80) | PAG1 (1.5) | | TBA (0.10) | CyHO (560) | 25.0 | 0.15 | 35 | 5.6 |
| 26 | Polymer 8 (80) | PAG1 (1.5) | | TBA (0.10) | CyHO (560) | 22.0 | 0.15 | 38 | 6.3 |
| 27 | Polymer 9 (80) | PAG1 (1.5) | | TBA (0.10) | CyHO (560) | 22.0 | 0.18 | 42 | 3.2 |
| 28 | Polymer 10 (80) | PAG1 (1.5) | | TBA (0.10) | PGMEA (480) | 19.0 | 0.16 | 30 | 6.6 |
| 29 | Polymer 11 (80) | PAG1 (1.5) | | TBA (0.10) | CyHO (560) | 28.0 | 0.16 | 45 | 5.5 |
| 30 | Polymer 12 (80) | PAG1 (1.5) | | TBA (0.10) | CyHO (560) | 15.0 | 0.18 | 46 | 5.8 |
| 31 | Polymer 13 (80) | PAG1 (1.5) | | TBA (0.10) | CyHO (560) | 19.0 | 0.18 | 48 | 5.5 |
| 32 | Polymer 14 (80) | PAG1 (1.5) | | TBA (0.10) | PGMEA (480) | 29.0 | 0.15 | 22 | 8.8 |
| 33 | Polymer 15 (80) | PAG1 (1.5) | | TBA (0.10) | PGMEA (480) | 32.0 | 0.15 | 12 | 9.8 |
| 34 | Polymer 16 (80) | PAG1 (1.5) | | PBA (0.10) | PGMEA (480) | 26.0 | 0.15 | 20 | 8.8 |
| 35 | Polymer 17 (80) | PAG1 (1.5) | | TBA (0.10) | PGMEA (480) | 29.0 | 0.17 | 25 | 5.6 |
| 36 | Polymer 18 (80) | PAG1 (1.5) | | TBA (0.10) | PGMEA (480) | 25.0 | 0.18 | 28 | 5.1 |

TABLE 3

| Example | Resin (part by weight) | Photacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 55 | Polymer 5 (40) Polymer 8 (40) | PAG1 (1.5) | | TEA (0.10) | CyHO (560) | 31.0 | 0.15 | 35 | 4.4 |
| 56 | Polymer 5 (40) Polymer 9 (40) | PAG1 (1.5) | | TEA (0.10) | CyHO (560) | 28.0 | 0.15 | 33 | 6.6 |
| 57 | Polymer 19 (80) | PAG6 (4.0) | | TEA (0.10) | PGMEA (360) | 35.0 | 0.15 | 25 | 5.0 |
| 58 | Polymer 20 (80) | PAG6 (4.0) | | TMMEA (0.10) | PGMEA (580) | 31.0 | 0.15 | 29 | 6.0 |
| 59 | Polymer 21 (80) | PAG6 (4.0) | | TMMEA (0.10) | PGMEA (560) | 28.0 | 0.15 | 33 | 6.3 |
| 60 | Polymer 22 (80) | PAG6 (4.0) | | TMMEA (0.10) | PGMEA (560) | 45.0 | 0.15 | 21 | 7.2 |
| 61 | Polymer 23 (80) | PAG6 (4.0) | | TMMEA (0.10) | PGMEA (560) | 42.0 | 0.15 | 20 | 8.2 |
| 62 | Polymer 24 (80) | PAG6 (4.0) | | TMMEA (0.10) | PGMEA (560) | 50.0 | 0.16 | 18 | 8.5 |
| 63 | Polymer 25 (80) | PAG6 (4.0) | | TMMEA (0.10) | PGMEA (560) | 33.0 | 0.15 | 22 | 4.8 |
| 64 | Polymer 26 (80) | PAG6 (4.0) | | TMMEA (0.10) | PGMEA (560) | 18.0 | 0.16 | 21 | 3.2 |

TABLE 4

| Example | Resin (part by weight) | Photacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 55 | Polymer 5 (40) Polymer 8 (40) | PAG1 (1.5) | | TEA (0.10) | CyHO (560) | 31.0 | 0.15 | 35 | 4.4 |
| 56 | Polymer 5 (40) Polymer 9 (40) | PAG1 (1.5) | | TEA (0.10) | CyHO (560) | 28.0 | 0.15 | 33 | 6.6 |
| 57 | Polymer 19 (80) | PAG6 (4.0) | | TMMEA (0.10) | PGMEA (560) | 35.0 | 0.15 | 25 | 5.0 |
| 58 | Polymer 20 (80) | PAG6 (4.0) | | TMMEA (0.10) | PGMEA (560) | 31.0 | 0.15 | 29 | 6.0 |
| 59 | Polymer 21 (80) | PAG6 (4.0) | | TMMEA (0.10) | PGMEA (560) | 28.0 | 0.15 | 33 | 6.3 |
| 60 | Polymer 22 (80) | PAG6 (4.0) | | TMMEA (0.10) | PGMEA (560) | 45.0 | 0.15 | 21 | 7.2 |
| 61 | Polymer 23 (80) | PAG6 (4.0) | | TMMEA (0.10) | PGMEA (560) | 42.0 | 0.15 | 20 | 8.2 |
| 62 | Polymer 24 (80) | PAG6 (4.0) | | TMMEA (0.10) | PGMEA (560) | 50.0 | 0.16 | 18 | 8.5 |
| 63 | Polymer 25 (80) | PAG6 (4.0) | | TMMEA (0.10) | PGMEA (560) | 33.0 | 0.15 | 22 | 4.8 |
| 64 | Polymer 26 (80) | PAG6 (4.0) | | TMMEA (0.10) | PGMEA (560) | 18.0 | 0.16 | 21 | 3.2 |

TABLE 5

| Comparative Example | Resin (part by weight) | Photacid generator (part by weight) | Dissolution inhibitor or organic acid (part by weight) | Basic compound (part by weight) | Solvent (part by weight) | Optimum exposure (mj/cm$^2$) | Resolution (μm) | I/G bias (nm) | Line-edge roughness (nm) |
|---|---|---|---|---|---|---|---|---|---|
| 1 | Polymer 1 (80) | PAG10 (1) | | TBA (0.10) | PGMEA (480) | 9.1 | 0.16 | 128 | 5.8 |
| 2 | Polymer 1 (80) | PAG11 (1) | | TBA (0.10) | PGMEA (480) | 9.9 | 0.16 | 145 | 4.9 |
| 3 | Polymer 1 (80) | PAG12 (1) | | TBA (0.10) | PGMEA (480) | 9.0 | 0.16 | 45 | 9.5 |
| 4 | Polymer 1 (80) | PAG13 (1) | | TBA (0.10) | PGMEA (480) | 9.4 | 0.16 | 168 | 4.3 |
| 5 | Polymer 1 (80) | PAG14 (1) | | TBA (0.10) | PGMEA (480) | 8.9 | 0.16 | 22 | 16.9 |
| 6 | Polymer 1 (80) | PAG15 (1) | | TBA (0.10) | PGMEA (480) | 9.2 | 0.16 | 18 | 16.9 |

The invention claimed is:

1. A photoacid generating compound of General Formula (1):

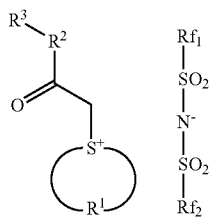

(1)

wherein $R^1$ is an alkylene group of 2 to 8 carbon atoms; and $R^2$ is a single bond, an oxygen atom, a nitrogen atom or an alkylene group of 1 to 4 carbon atoms; $R^3$ is a straight-chained, branched or cyclic alkyl group of 1 to 8 carbon atoms, or an aryl group of 6 to 10 carbon atoms, and may be substituted with an alkyl group of 1 to 4 carbon atoms, a fluorinated alkyl group of 1 to 4 carbon atoms, an alkoxy group of 1 to 4 carbons, a fluorinated alkoxy group of 1 to 4 carbons atoms, a nitro group, a cyano group, a fluorine atom, a phenyl group, a substituted phenyl group, an acetyl group or a benzoyloxy group; either of or both of $Rf_1$ and $Rf_2$ are straight-chained, branched or cyclic alkyl groups, each having 1 to 20 carbon atoms containing at least one fluorine atom, and may comprise a hydroxyl group, a carbonyl group, an ester group, an ether group or an aryl group; when only one of $Rf_1$ and $Rf_2$ is the straight-chained, branched or cyclic alkyl group, having 1 to 20 carbon atoms containing at least one fluorine atom, the other thereof is a straight-chained, branched or cyclic alkyl group, having 1 to 20 carbon atoms, and may comprise a hydroxyl group, a carbonyl group, an ester group, an ether group or an aryl group; and $Rf_1$ and $Rf_2$ may be bonded together and form a ring.

2. The photoacid generating compound according to claim 1 wherein $R^1$ is an alkylene group of 4 or 5 carbon atoms.

3. The photoacid generating compound according to claim 1 wherein $R^3$ is a phenyl group or a naphthyl group.

4. A chemically amplified positive resist material comprising a base resin, an acid generator and a solvent wherein the acid generator generates an alkylimidic acid containing a fluorine group.

5. The chemically amplified positive resist material according to claim 4 wherein said acid generator is an onium salt represented by General Formulas (1) or (2) below:

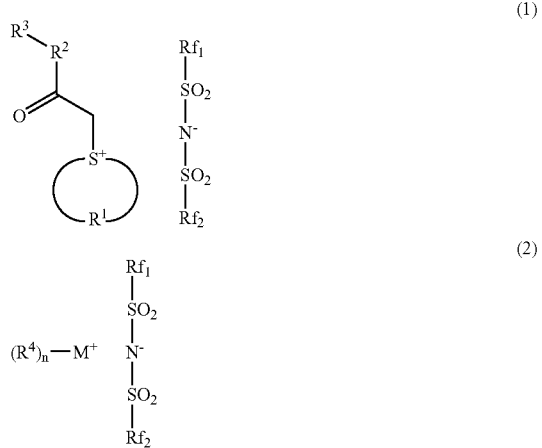

wherein either of or both of $Rf_1$ and $Rf_2$ are straight-chained, branched or cyclic alkyl groups, each having 1 to 20 carbon atoms containing at least one fluorine atom, and may comprise a hydroxyl group, a carbonyl group, an ester group, an ether group or an aryl group; when only one of $Rf_1$ and $Rf_2$ is the straight-chained, branched or cyclic alkyl group, having 1 to 20 carbon atoms containing at least one fluorine atom, the other thereof is a straight-chained, branched or cyclic alkyl group, having 1 to 20 carbon atoms, and may comprise a hydroxyl group, a carbonyl group, an ester group, an ether group or an aryl group; $Rf_1$ and $Rf_2$ may be bonded together to form a ring; $R^1$ is an alkylene group of 2 to 8 carbon atoms; $R^2$ is a single bond, an oxygen atom, a nitrogen atom or an alkylene group of 1 to 4 carbon atoms; $R^3$ is a straight-chained, branched or cyclic alkyl group of 1 to 8 carbon atoms, or an aryl group of 6 to 10 carbon atoms, and may be substituted with an alkyl group of 1 to 4 carbon atoms, a fluorinated alkyl group of 1 to 4 carbon atoms, an alkoxy group of 1 to 4 carbon atoms, a fluorinated alkoxy group of 1 to 4 carbon atoms, a nitro group, a cyano group, a fluorine atom, a phenyl group, a substituted phenyl group, an acetyl group, or a benzoyloxy group; $R^4$, which may be same or different, is independently a straight-chained, branched or cyclic alkyl group of 1 to 12 carbon atoms which may comprise a carbonyl group, an ester group, an ether group, a thioether group or a double bond, or is independently an aryl group of 6 to 12 carbon atoms or an aralkyl group of 7 to 20 carbon atoms; $M^+$ is iodonium or sulfonium; and n is 2 or 3.

6. The chemically amplified positive resist material according to claim 4 wherein said base resin is insoluble or slightly soluble in a developing solution, and becomes soluble therein in present of an acid.

7. The chemically amplified positive resist material according to claim 5 wherein said base resin is insoluble or slightly soluble in a developing solution, and becomes soluble therein in present of an acid.

8. The chemically amplified positive resist material according to claim 4 wherein said base resin is one or more polymers selected from the group consisting of polyhydroxystyrene and a derivative of polyhydroxystyrene wherein hydroxyl groups thereof are partially or entirely substituted with a acid-labile groups; a polyacrylic acid and an an ester thereof; a polymethacrylic acid and an ester thereof; a copolymer of acrylic acid and methacrylic acid and an ester of the copolymer; a copolymer of cycloolefin and maleic anhydride; a copolymer of cycloolefin, maleic anhydride and acrylate; a copolymer of cycloolefin, maleic anhydride and methacrylate; a copolymer of cycloolefin, maleic anhydride, acrylate and methacrylate; a copolymer of cycloolefin and maleimide; a copolymer of cycloolefin, maleimide and acrylate; a copolymer of cycloolefin, maleimide and methacrylate; a copolymer of cycloolefin, maleimide, acrylate and methacrylate; polynorbornene; and a metathesis polymer by ring-opening polymerization.

9. The chemically amplified positive resist material according to claim 5 wherein said base resin is one or more polymers selected from the group consisting of polyhydroxystyrene and a derivative of polyhydroxystyrene wherein hydroxyl groups thereof are partially or entirely substituted with a acid-labile groups; a polyacrylic acid and an an ester thereof; a polymethacrylic acid and an ester thereof; a copolymer of acrylic acid and methacrylic acid and an ester of the copolymer; a copolymer of cycloolefin and maleic anhydride; a copolymer of cycloolefin, maleic anhydride and acrylate; a copolymer of cycloolefin, maleic anhydride and methacrylate; a copolymer of cycloolefin, maleic anhydride, acrylate and methacrylate; a copolymer of cycloolefin and maleimide; a copolymer of cycloolefin, maleimide and acrylate; a copolymer of cycloolefin, maleimide and methacrylate; a copolymer of cycloolefin, maleimide, acrylate and methacrylate; polynorbornene; and a metathesis polymer by ring-opening polymerization.

10. The chemically amplified positive resist material according to claim 4 wherein said base resin has a polymeric structure which contains a silicon atom.

11. The chemically amplified positive resist material according to claim 5 wherein said base resin has a polymeric structure which contains a silicon atom.

12. The chemically amplified positive resist material according to claim 4, further comprising a basic compound.

13. The chemically amplified positive resist material according to claim 5, further comprising a basic compound.

14. The chemically amplified positive resist material according to claim 4, further comprising a dissolution inhibitor.

15. The chemically amplified positive resist material according to claim 5, further comprising a dissolution inhibitor.

16. A pattern forming method comprising a step of applying the resist material according to claim 4 to the substrate, a step of performing exposure to a high-energy ray of a wavelength of 300 nm or less through a photomask following heat treatment, and a step of performing development by a developing solution following heat treatment.

17. A pattern forming method comprising a step of applying the resist material according to claim 5 to the substrate, a step of performing exposure to a high-energy ray of a wavelength of 300 nm or less through a photomask following heat treatment, and a step of performing development by a developing solution following heat treatment.

* * * * *

UNITED STATES PATENT AND TRADEMARK OFFICE
CERTIFICATE OF CORRECTION

PATENT NO.       : 7,303,852 B2
APPLICATION NO.  : 10/375773
DATED            : December 4, 2007
INVENTOR(S)      : Hatakeyama et al.

It is certified that error appears in the above-identified patent and that said Letters Patent is hereby corrected as shown below:

Column 16, Lines 23 to 35: Please correct to appear as follows:

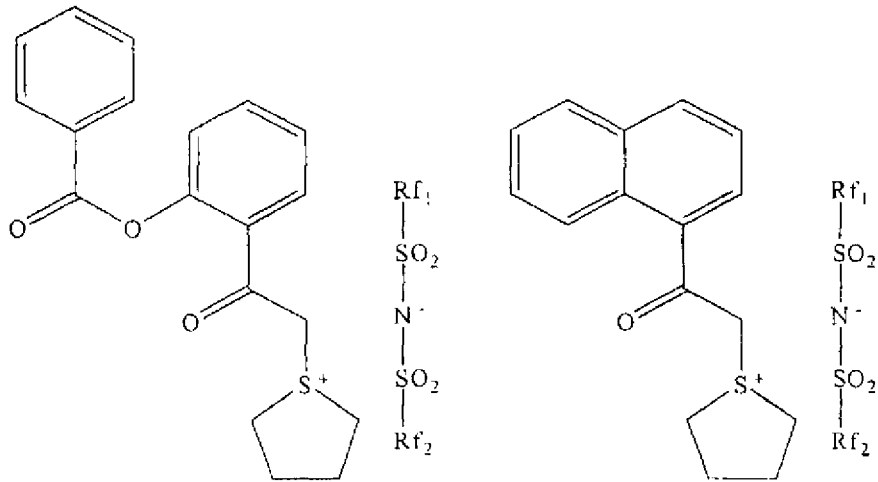

Column 17, Lines 50 to 58: Please correct to appear as follows:

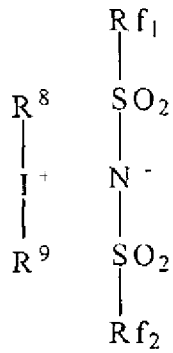

UNITED STATES PATENT AND TRADEMARK OFFICE
CERTIFICATE OF CORRECTION

PATENT NO.        : 7,303,852 B2
APPLICATION NO.   : 10/375773
DATED             : December 4, 2007
INVENTOR(S)       : Hatakeyama et al.

It is certified that error appears in the above-identified patent and that said Letters Patent is hereby corrected as shown below:

Column 19, Lines 10 to 20: Please correct to appear as follows:

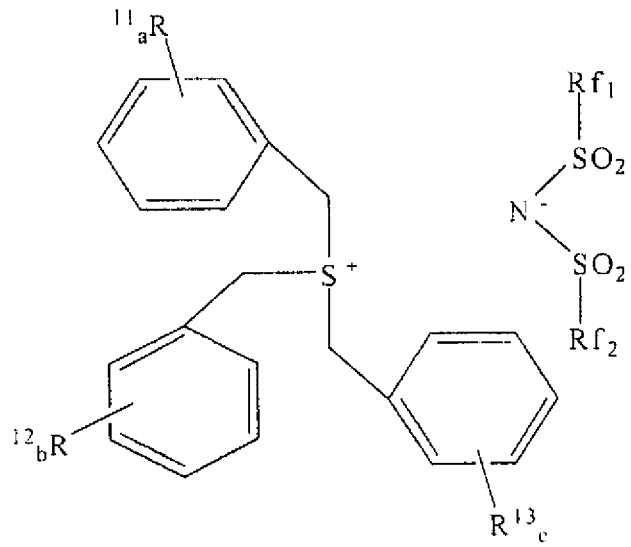

Column 21, Lines 54 to 66: Please correct to appear as follows:

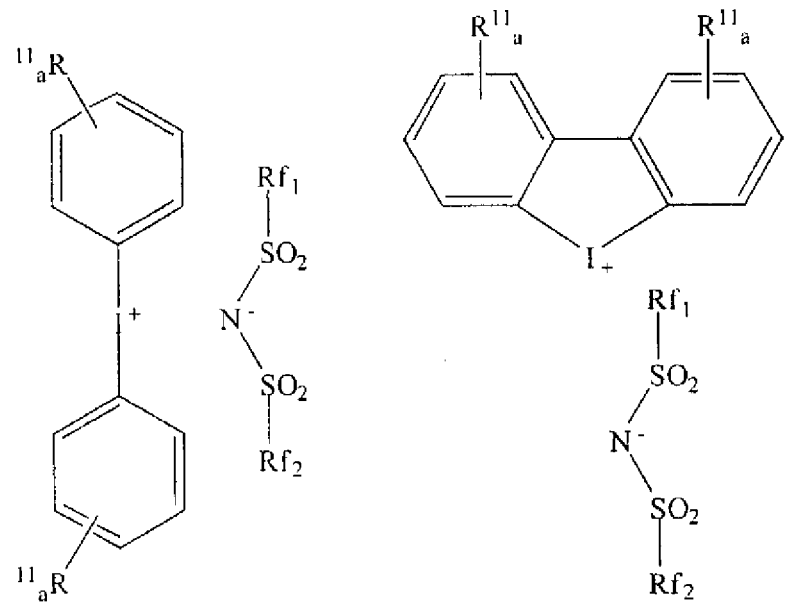

UNITED STATES PATENT AND TRADEMARK OFFICE
CERTIFICATE OF CORRECTION

PATENT NO.         : 7,303,852 B2
APPLICATION NO.   : 10/375773
DATED              : December 4, 2007
INVENTOR(S)        : Hatakeyama et al.

It is certified that error appears in the above-identified patent and that said Letters Patent is hereby corrected as shown below:

Column 22, Lines 2 to 16: Please correct to appear as follows:

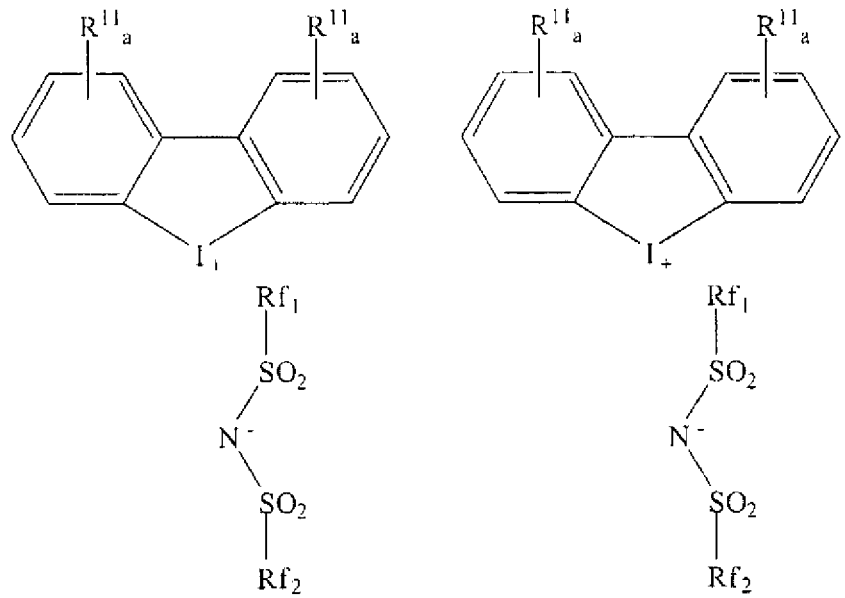

Column 24, Lines 37 to 42: Please correct to appear as follows:

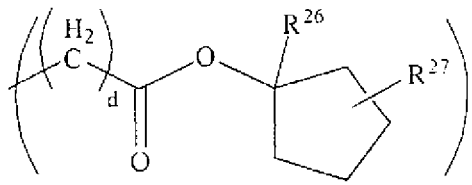

Column 25, Lines 17 to 22: Please correct to appear as follows:

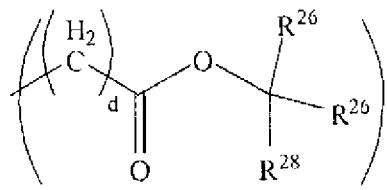

UNITED STATES PATENT AND TRADEMARK OFFICE
CERTIFICATE OF CORRECTION

PATENT NO. : 7,303,852 B2
APPLICATION NO. : 10/375773
DATED : December 4, 2007
INVENTOR(S) : Hatakeyama et al.

It is certified that error appears in the above-identified patent and that said Letters Patent is hereby corrected as shown below:

Column 43, Line 52: Please correct end of paragraph and beginning of new paragraph "forms a ring Specific examples"
To read: --forms a ring.
      Specific examples--

Column 56, Lines 16 to 20: Please correct to appear as follows:

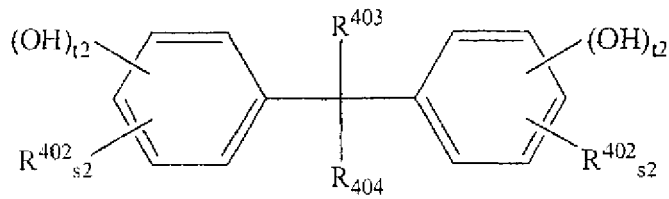

UNITED STATES PATENT AND TRADEMARK OFFICE
CERTIFICATE OF CORRECTION

PATENT NO. : 7,303,852 B2
APPLICATION NO. : 10/375773
DATED : December 4, 2007
INVENTOR(S) : Hatakeyama et al.

It is certified that error appears in the above-identified patent and that said Letters Patent is hereby corrected as shown below:

Column 70, Lines 56 to 64: Please correct to appear as follows:

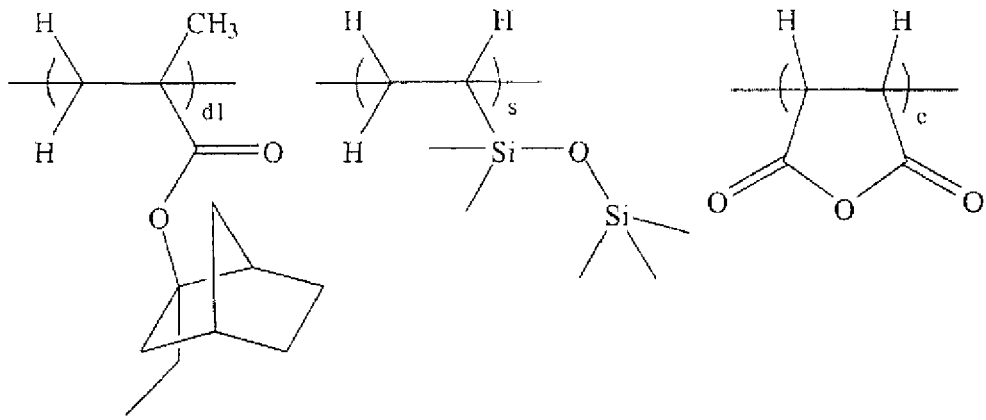

Signed and Sealed this

Twelfth Day of May, 2009

JOHN DOLL
*Acting Director of the United States Patent and Trademark Office*